United States Patent
Ryan et al.

(10) Patent No.: US 10,774,380 B2
(45) Date of Patent: *Sep. 15, 2020

(54) METHODS FOR MULTIPLEX PCR AMPLIFICATION OF TARGET LOCI IN A NUCLEIC ACID SAMPLE

(71) Applicant: Natera, Inc., San Carlos, CA (US)

(72) Inventors: Allison Ryan, Belmont, CA (US); Styrmir Sigurjonsson, San Jose, CA (US); Milena Banjevic, Los Altos Hills, CA (US); George Gemelos, Portland, OR (US); Matthew Hill, Belmont, CA (US); Johan Baner, San Francisco, CA (US); Matthew Rabinowitz, San Francisco, CA (US); Zachary Demko, San Francisco, CA (US)

(73) Assignee: Natera, Inc., San Carlos, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/287,662

(22) Filed: Feb. 27, 2019

(65) Prior Publication Data

US 2019/0194743 A1 Jun. 27, 2019

Related U.S. Application Data

(63) Continuation of application No. 16/012,667, filed on Jun. 19, 2018, which is a continuation of application No. 13/335,043, filed on Dec. 22, 2011, now Pat. No. 10,113,196, which is a continuation-in-part of application No. 13/300,235, filed on Nov. 18, 2011, now Pat. No. 10,017,812, which is a continuation-in-part of application No. 13/110,685, filed on May 18, 2011, now Pat. No. 8,825,412.

(60) Provisional application No. 61/542,508, filed on Oct. 3, 2011, provisional application No. 61/571,248, filed on Jun. 23, 2011, provisional application No. 61/516,996, filed on Apr. 12, 2011, provisional application No. 61/448,547, filed on Mar. 2, 2011, provisional application No. 61/462,972, filed on Feb. 9, 2011, provisional application No. 61/398,159, filed on Jun. 21, 2010, provisional application No. 61/398,850, filed on May 18, 2010.

(51) Int. Cl.
*C12Q 1/6869* (2018.01)
*G16B 10/00* (2019.01)
*C12Q 1/6876* (2018.01)

(52) U.S. Cl.
CPC ......... *C12Q 1/6869* (2013.01); *C12Q 1/6876* (2013.01); *G16B 10/00* (2019.02); *C12Q 2600/156* (2013.01)

(58) Field of Classification Search
None
See application file for complete search history.

(56) References Cited

U.S. PATENT DOCUMENTS

| | | |
|---|---|---|
| 5,635,366 A | 6/1997 | Cooke et al. |
| 5,716,776 A | 2/1998 | Bogart |
| 5,753,467 A | 5/1998 | Jensen et al. |
| 5,824,467 A | 10/1998 | Mascarenhas |
| 5,854,033 A | 12/1998 | Lizardi |
| 5,860,917 A | 1/1999 | Comanor et al. |
| 5,972,602 A | 11/1999 | Hyland et al. |
| 5,994,148 A | 11/1999 | Stewart et al. |
| 6,001,611 A | 12/1999 | Will |
| 6,025,128 A | 2/2000 | Veltri et al. |
| 6,066,454 A | 5/2000 | Lipshutz et al. |
| 6,100,029 A | 8/2000 | Lapidus et al. |
| 6,108,635 A | 8/2000 | Herren et al. |
| 6,124,120 A | 9/2000 | Lizardi |
| 6,143,496 A | 11/2000 | Brown et al. |
| 6,156,504 A | 12/2000 | Gocke et al. |
| 6,180,349 B1 | 1/2001 | Ginzinger |
| 6,235,472 B1 | 2/2001 | Landegren et al. |
| 6,214,558 B1 | 4/2001 | Shuber et al. |
| 6,221,603 B1 | 4/2001 | Mahtani |
| 6,258,540 B1 | 7/2001 | Lo et al. |
| 6,300,077 B1 | 10/2001 | Shuber et al. |
| 6,479,235 B1 | 11/2002 | Schumm et al. |
| 6,440,706 B1 | 12/2002 | Vogelstein et al. |
| 6,489,135 B1 | 12/2002 | Parrott et al. |
| 6,720,140 B1 | 4/2004 | Hartley et al. |

(Continued)

FOREIGN PATENT DOCUMENTS

| CN | 1650032 A | 8/2005 |
|---|---|---|
| CN | 1674028 A | 9/2005 |

(Continued)

OTHER PUBLICATIONS

Wittwer, Carl T., et al. "Real-time multiplex PCR assays." Methods 25.4 (2001): 430-442.*
Ballif, B. C. et al., "Detection of Low-Level Mosaicism by Array CGH in Routine Diagnostic Specimens", American Journal of Medical Genetics Part A, vol. 140A, 2006, 2757-2767.
Birkenkamp-Demtroder, K. et al., "Abstract 3653: Sequencing of plasma cfDNA from patients with locally advanced bladder cancer for surveillance and therapeutic efficacy monitoring", Cancer Research, vol. 78, No. 13 Supplement, Jul. 2019, 1 page.
Burnham, P. et al., "Myriad Applications of Circulating Cell-Free DNA in Precision Organ Transplant Monitoring", Annals of the American Thoracic Society, vol. 14, Supplement 3, Sep. 2017, S237-S241.

(Continued)

*Primary Examiner* — G Steven Vanni

(57) ABSTRACT

Methods for non-invasive prenatal paternity testing are disclosed herein. The method uses genetic measurements made on plasma taken from a pregnant mother, along with genetic measurements of the alleged father, and genetic measurements of the mother, to determine whether or not the alleged father is the biological father of the fetus. This is accomplished by way of an informatics based method that can compare the genetic fingerprint of the fetal DNA found in maternal plasma to the genetic fingerprint of the alleged father.

16 Claims, 9 Drawing Sheets

(56) References Cited

U.S. PATENT DOCUMENTS

| | | |
|---|---|---|
| 6,794,140 B1 | 9/2004 | Goldsborough |
| 6,807,491 B2 | 10/2004 | Pavlovic et al. |
| 6,852,487 B1 | 10/2005 | Barany et al. |
| 6,958,211 B2 | 10/2005 | Vingerhoets et al. |
| 6,964,847 B1 | 11/2005 | Englert |
| 7,035,739 B2 | 4/2006 | Schadt et al. |
| 7,058,517 B1 | 6/2006 | Denton et al. |
| 7,058,616 B1 | 6/2006 | Larder et al. |
| 7,218,764 B2 | 5/2007 | Vaisberg et al. |
| 7,297,485 B2 | 11/2007 | Bornarth et al. |
| 7,332,277 B2 | 2/2008 | Dhallan |
| 7,410,764 B2 | 8/2008 | Gocke et al. |
| 7,414,118 B1 | 8/2008 | Mullah et al. |
| 7,442,506 B2 | 12/2008 | Dhallan |
| 7,459,273 B2 | 12/2008 | Jones et al. |
| 7,645,576 B2 | 1/2010 | Lo et al. |
| 7,700,325 B2 | 5/2010 | Cantor et al. |
| 7,718,367 B2 | 5/2010 | Lo et al. |
| 7,718,370 B2 | 5/2010 | Dhallan |
| 7,727,720 B2 | 6/2010 | Dhallan |
| 7,805,282 B2 | 9/2010 | Casey |
| 7,838,647 B2 | 11/2010 | Hahn et al. |
| 7,888,017 B2 | 8/2011 | Quake |
| 8,008,018 B2 | 9/2011 | Quake et al. |
| 8,024,128 B2 | 9/2011 | Rabinowitz et al. |
| 8,133,719 B2 | 3/2012 | Drmanac et al. |
| 8,137,912 B2 | 5/2012 | Kapur et al. |
| 8,173,370 B2 | 5/2012 | Oeth et al. |
| 8,168,389 B2 | 6/2012 | Shoemaker et al. |
| 8,195,415 B2 | 10/2012 | Fan et al. |
| 8,296,076 B2 | 11/2012 | Fan et al. |
| 8,304,187 B2 | 11/2012 | Fernando |
| 8,318,430 B2 | 11/2012 | Chuu et al. |
| 8,450,063 B2 | 5/2013 | Dube et al. |
| 8,467,976 B2 | 8/2013 | Lo et al. |
| 8,515,679 B2 | 8/2013 | Rabinowitz et al. |
| 8,532,930 B2 | 9/2013 | Rabinowitz et al. |
| 8,682,592 B2 | 3/2014 | Rabinowitz et al. |
| 8,825,412 B2 | 9/2014 | Rabinowitz et al. |
| 9,085,798 B2 | 7/2015 | Chee |
| 9,323,888 B2 | 4/2016 | Rava et al. |
| 9,476,095 B2 | 10/2016 | Vogelstein et al. |
| 9,487,829 B2 | 11/2016 | Vogelstein et al. |
| 9,598,731 B2 | 3/2017 | Talasaz |
| 9,677,118 B2 | 6/2017 | Zimmermann et al. |
| 10,081,839 B2 | 9/2018 | Rabinowitz et al. |
| 10,083,273 B2 | 9/2018 | Rabinowitz et al. |
| 10,308,981 B2 | 6/2019 | Sparks et al. |
| 10,316,362 B2 | 6/2019 | Babiarz et al. |
| 2001/0051341 A1 | 12/2001 | Lo et al. |
| 2001/0053519 A1 | 12/2001 | Fodor et al. |
| 2002/0006622 A1 | 1/2002 | Bradley et al. |
| 2002/0107640 A1 | 8/2002 | Ideker et al. |
| 2003/0009295 A1 | 1/2003 | Markowitz et al. |
| 2003/0065535 A1 | 4/2003 | Karlov et al. |
| 2003/0077586 A1 | 4/2003 | Pavlovic et al. |
| 2003/0101000 A1 | 5/2003 | Bader et al. |
| 2003/0119004 A1 | 6/2003 | Wenz et al. |
| 2003/0211489 A1 | 11/2003 | Shen et al. |
| 2003/0228613 A1 | 12/2003 | Bornarth et al. |
| 2004/0033596 A1 | 2/2004 | Threadgill et al. |
| 2004/0117346 A1 | 6/2004 | Stoffel et al. |
| 2004/0137470 A1 | 7/2004 | Dhallan |
| 2004/0146866 A1 | 7/2004 | Fu |
| 2004/0157243 A1 | 8/2004 | Huang et al. |
| 2004/0197797 A1 | 10/2004 | Inoko et al. |
| 2004/0209299 A1 | 10/2004 | Pinter et al. |
| 2004/0229231 A1 | 11/2004 | Frudakis et al. |
| 2004/0236518 A1 | 11/2004 | Pavlovic et al. |
| 2004/0259100 A1 | 12/2004 | Gunderson et al. |
| 2005/0009069 A1 | 1/2005 | Liu et al. |
| 2005/0049793 A1 | 3/2005 | Paterlini-brechot |
| 2005/0053950 A1 | 3/2005 | Ubani et al. |
| 2005/0079521 A1 | 4/2005 | Beaulieu et al. |
| 2005/0079535 A1 | 4/2005 | Kirchgesser et al. |
| 2005/0123914 A1 | 6/2005 | Katz et al. |
| 2005/0130173 A1 | 6/2005 | Leamon et al. |
| 2005/0142577 A1 | 6/2005 | Jones et al. |
| 2005/0144664 A1 | 6/2005 | Smith et al. |
| 2005/0164241 A1 | 7/2005 | Hahn et al. |
| 2005/0216207 A1 | 9/2005 | Kermani |
| 2005/0221341 A1 | 10/2005 | Shimkets et al. |
| 2005/0227263 A1 | 10/2005 | Green et al. |
| 2005/0250111 A1 | 11/2005 | Xie et al. |
| 2005/0255508 A1 | 11/2005 | Casey et al. |
| 2005/0272073 A1 | 12/2005 | Vaisberg et al. |
| 2006/0019278 A1 | 1/2006 | Lo et al. |
| 2006/0040300 A1 | 2/2006 | Dapprich et al. |
| 2006/0052945 A1 | 3/2006 | Rabinowitz et al. |
| 2006/0057618 A1 | 3/2006 | Piper et al. |
| 2006/0068394 A1 | 3/2006 | Langmore et al. |
| 2006/0088574 A1 | 4/2006 | Manning et al. |
| 2006/0099614 A1 | 5/2006 | Gill et al. |
| 2006/0121452 A1 | 6/2006 | Dhallan |
| 2006/0134662 A1 | 6/2006 | Pratt et al. |
| 2006/0141499 A1 | 6/2006 | Sher et al. |
| 2006/0229823 A1 | 8/2006 | Liu |
| 2006/0210997 A1 | 9/2006 | Myerson et al. |
| 2006/0216738 A1 | 9/2006 | Wada et al. |
| 2006/0281105 A1 | 12/2006 | Li et al. |
| 2007/0020640 A1 | 1/2007 | McCloskey et al. |
| 2007/0027636 A1 | 2/2007 | Rabinowitz |
| 2007/0031857 A1 | 2/2007 | Makarov et al. |
| 2007/0042384 A1 | 2/2007 | Li et al. |
| 2007/0059707 A1 | 3/2007 | Cantor et al. |
| 2007/0122805 A1 | 5/2007 | Cantor et al. |
| 2007/0128624 A1 | 6/2007 | Gormley et al. |
| 2007/0178478 A1 | 8/2007 | Dhallan |
| 2007/0178501 A1 | 8/2007 | Rabinowitz et al. |
| 2007/0184467 A1 | 8/2007 | Rabinowitz et al. |
| 2007/0202525 A1 | 8/2007 | Quake et al. |
| 2007/0202536 A1 | 8/2007 | Yamanishi et al. |
| 2007/0207466 A1 | 9/2007 | Cantor et al. |
| 2007/0212689 A1 | 9/2007 | Bianchi et al. |
| 2007/0243549 A1 | 10/2007 | Bischoff |
| 2007/0259351 A1 | 11/2007 | Chinitz |
| 2008/0020390 A1 | 1/2008 | Mitchell |
| 2008/0026390 A1 | 1/2008 | Stoughton et al. |
| 2008/0038733 A1 | 2/2008 | Bischoff et al. |
| 2008/0070792 A1 | 3/2008 | Stoughton |
| 2008/0071076 A1 | 3/2008 | Hahn et al. |
| 2008/0085836 A1 | 4/2008 | Kearns et al. |
| 2008/0090239 A1 | 4/2008 | Shoemaker et al. |
| 2008/0096766 A1 | 4/2008 | Lee |
| 2008/0102455 A1 | 5/2008 | Poetter |
| 2008/0138809 A1 | 6/2008 | Kapur et al. |
| 2008/0182244 A1 | 7/2008 | Tafas et al. |
| 2008/0193927 A1 | 8/2008 | Mann et al. |
| 2008/0220422 A1 | 9/2008 | Shoemaker et al. |
| 2008/0234142 A1 | 9/2008 | Lietz |
| 2008/0243398 A1 | 10/2008 | Rabinowitz et al. |
| 2008/0305473 A1 | 12/2008 | Chowdary et al. |
| 2009/0023190 A1 | 1/2009 | Lao et al. |
| 2009/0029377 A1 | 1/2009 | Lo et al. |
| 2009/0087847 A1 | 4/2009 | Lo et al. |
| 2009/0098534 A1 | 4/2009 | Weier et al. |
| 2009/0099041 A1 | 4/2009 | Church et al. |
| 2009/0143570 A1 | 6/2009 | Jiang et al. |
| 2009/0176662 A1 | 7/2009 | Rigatti et al. |
| 2009/0221620 A1 | 9/2009 | Luke et al. |
| 2009/0228299 A1 | 9/2009 | Kangarloo et al. |
| 2009/0317817 A1 | 12/2009 | Oeth et al. |
| 2010/0035232 A1 | 2/2010 | Ecker et al. |
| 2010/0112575 A1 | 5/2010 | Fan et al. |
| 2010/0112590 A1 | 5/2010 | Lo et al. |
| 2010/0120038 A1 | 5/2010 | Mir et al. |
| 2010/0124751 A1 | 5/2010 | Quake et al. |
| 2010/0129874 A1 | 5/2010 | Mitra et al. |
| 2010/0138165 A1 | 6/2010 | Fan et al. |
| 2010/0171954 A1 | 7/2010 | Quake et al. |
| 2010/0184069 A1 | 7/2010 | Fernando et al. |
| 2010/0184152 A1 | 7/2010 | Sandler |
| 2010/0196892 A1 | 8/2010 | Quake et al. |
| 2010/0203538 A1 | 8/2010 | Dube et al. |

(56) References Cited

U.S. PATENT DOCUMENTS

| | | |
|---|---|---|
| 2010/0216153 A1 | 8/2010 | Lapidus et al. |
| 2010/0248231 A1 | 9/2010 | Wei et al. |
| 2010/0255492 A1 | 10/2010 | Quake et al. |
| 2010/0256013 A1 | 10/2010 | Quake et al. |
| 2010/0273678 A1 | 10/2010 | Alexandre et al. |
| 2010/0285537 A1 | 11/2010 | Zimmermann |
| 2010/0291572 A1 | 11/2010 | Stoughton et al. |
| 2010/0291635 A1 | 11/2010 | Peleg |
| 2010/0323352 A1 | 12/2010 | Lo et al. |
| 2011/0033862 A1 | 2/2011 | Rabinowitz et al. |
| 2011/0039724 A1 | 2/2011 | Lo et al. |
| 2011/0071031 A1 | 3/2011 | Khripin et al. |
| 2011/0086769 A1 | 4/2011 | Oliphant et al. |
| 2011/0092763 A1 | 4/2011 | Rabinowitz et al. |
| 2011/0105353 A1 | 5/2011 | Lo et al. |
| 2011/0151442 A1 | 6/2011 | Fan et al. |
| 2011/0159499 A1 | 6/2011 | Hindson et al. |
| 2011/0160078 A1 | 6/2011 | Fodor et al. |
| 2011/0178719 A1 | 7/2011 | Rabinowitz et al. |
| 2011/0201507 A1 | 8/2011 | Rava et al. |
| 2011/0224087 A1 | 9/2011 | Quake et al. |
| 2011/0246083 A1 | 10/2011 | Fan et al. |
| 2011/0251149 A1 | 10/2011 | Perrine et al. |
| 2011/0288780 A1 | 11/2011 | Rabinowitz et al. |
| 2011/0300608 A1 | 12/2011 | Ryan et al. |
| 2011/0301854 A1 | 12/2011 | Curry et al. |
| 2011/0318734 A1 | 12/2011 | Lo et al. |
| 2012/0003635 A1 | 1/2012 | Lo et al. |
| 2012/0010085 A1 | 1/2012 | Rava et al. |
| 2012/0034603 A1 | 2/2012 | Oliphant et al. |
| 2012/0034685 A1 | 2/2012 | Sparks et al. |
| 2012/0108460 A1 | 5/2012 | Quake et al. |
| 2012/0122701 A1 | 5/2012 | Ryan et al. |
| 2012/0165203 A1 | 6/2012 | Quake et al. |
| 2012/0185176 A1 | 7/2012 | Rabinowitz et al. |
| 2012/0190020 A1 | 7/2012 | Oliphant et al. |
| 2012/0190021 A1 | 7/2012 | Oliphant et al. |
| 2012/0191358 A1 | 7/2012 | Oliphant et al. |
| 2012/0196754 A1 | 8/2012 | Quake et al. |
| 2012/0214678 A1 | 8/2012 | Rava et al. |
| 2012/0264121 A1 | 10/2012 | Rava et al. |
| 2012/0270212 A1 | 10/2012 | Rabinowitz et al. |
| 2012/0295810 A1 | 11/2012 | Quake et al. |
| 2012/0295819 A1 | 11/2012 | Leamon et al. |
| 2013/0017549 A1 | 1/2013 | Hong |
| 2013/0024127 A1 | 1/2013 | Stuelpnagel |
| 2013/0034546 A1 | 2/2013 | Rava et al. |
| 2013/0060483 A1 | 3/2013 | Struble et al. |
| 2013/0069869 A1 | 3/2013 | Akao et al. |
| 2013/0090250 A1 | 4/2013 | Sparks et al. |
| 2013/0116130 A1 | 5/2013 | Fu et al. |
| 2013/0123120 A1 | 5/2013 | Zimmermann et al. |
| 2013/0130923 A1 | 5/2013 | Ehrich et al. |
| 2013/0178373 A1 | 7/2013 | Rabinowitz et al. |
| 2013/0190653 A1 | 7/2013 | Alvarez Ramos |
| 2013/0196862 A1 | 8/2013 | Rabinowitz et al. |
| 2013/0210644 A1 | 8/2013 | Stoughton et al. |
| 2013/0225422 A1 | 8/2013 | Rabinowitz et al. |
| 2013/0252824 A1 | 9/2013 | Rabinowitz |
| 2013/0253369 A1 | 9/2013 | Rabinowitz et al. |
| 2013/0261004 A1 | 10/2013 | Ryan et al. |
| 2013/0274116 A1 | 10/2013 | Rabinowitz et al. |
| 2013/0303461 A1 | 11/2013 | Iafrate et al. |
| 2013/0323731 A1 | 12/2013 | Lo et al. |
| 2013/0325360 A1 | 12/2013 | Deciu et al. |
| 2014/0032128 A1 | 1/2014 | Rabinowitz et al. |
| 2014/0038830 A1 | 2/2014 | Srinivasan et al. |
| 2014/0051585 A1 | 2/2014 | Prosen et al. |
| 2014/0065621 A1 | 3/2014 | Mhatre et al. |
| 2014/0087385 A1 | 3/2014 | Rabinowitz et al. |
| 2014/0094373 A1 | 4/2014 | Zimmermann et al. |
| 2014/0100126 A1 | 4/2014 | Rabinowitz |
| 2014/0100134 A1 | 4/2014 | Rabinowitz et al. |
| 2014/0141981 A1 | 5/2014 | Zimmermann et al. |
| 2014/0154682 A1 | 6/2014 | Rabinowitz et al. |
| 2014/0155274 A1 | 6/2014 | Xie et al. |
| 2014/0162269 A1 | 6/2014 | Rabinowitz |
| 2014/0193816 A1 | 7/2014 | Rabinowitz et al. |
| 2014/0206552 A1 | 7/2014 | Rabinowitz et al. |
| 2014/0227705 A1 | 8/2014 | Vogelstein et al. |
| 2014/0256558 A1 | 9/2014 | Varley et al. |
| 2014/0256569 A1 | 9/2014 | Rabinowitz et al. |
| 2014/0272956 A1 | 9/2014 | Huang et al. |
| 2014/0287934 A1 | 9/2014 | Szelinger et al. |
| 2014/0296081 A1 | 10/2014 | Diehn et al. |
| 2014/0329245 A1 | 11/2014 | Spier et al. |
| 2014/0336060 A1 | 11/2014 | Rabinowitz |
| 2015/0051087 A1 | 2/2015 | Rabinowitz et al. |
| 2015/0064695 A1 | 3/2015 | Katz et al. |
| 2015/0087535 A1 | 3/2015 | Patel |
| 2015/0147815 A1 | 5/2015 | Babiarz et al. |
| 2015/0197786 A1 | 7/2015 | Osborne et al. |
| 2015/0232938 A1 | 8/2015 | Mhatre |
| 2015/0265995 A1 | 9/2015 | Head et al. |
| 2016/0145682 A1 | 5/2016 | Woodward et al. |
| 2016/0186253 A1 | 6/2016 | Talasaz et al. |
| 2016/0201124 A1 | 7/2016 | Donahue et al. |
| 2016/0257993 A1 | 9/2016 | Fu et al. |
| 2016/0289740 A1 | 10/2016 | Fu et al. |
| 2016/0289753 A1 | 10/2016 | Osborne et al. |
| 2016/0312276 A1 | 10/2016 | Fu et al. |
| 2016/0319345 A1 | 11/2016 | Gnerre et al. |
| 2016/0369333 A1 | 12/2016 | Babiarz et al. |
| 2017/0121716 A1 | 5/2017 | Rodi et al. |
| 2017/0342477 A1 | 11/2017 | Jensen et al. |
| 2018/0127744 A1 | 5/2018 | Hu et al. |
| 2018/0148777 A1 | 5/2018 | Kirkizlar et al. |
| 2018/0155775 A1 | 6/2018 | Zimmermann et al. |
| 2018/0155776 A1 | 6/2018 | Zimmermann et al. |
| 2018/0155779 A1 | 6/2018 | Zimmermann et al. |
| 2018/0155785 A1 | 6/2018 | Rabinowitz et al. |
| 2018/0155786 A1 | 6/2018 | Rabinowitz et al. |
| 2018/0155792 A1 | 6/2018 | Rabinowitz et al. |
| 2018/0171409 A1 | 6/2018 | Rabinowitz et al. |
| 2018/0171420 A1 | 6/2018 | Babiarz et al. |
| 2018/0173845 A1 | 6/2018 | Sigurjonsson et al. |
| 2018/0173846 A1 | 6/2018 | Sigurjonsson et al. |
| 2018/0201995 A1 | 7/2018 | Rabinowitz et al. |
| 2018/0237841 A1 | 8/2018 | Stray et al. |
| 2018/0298439 A1 | 10/2018 | Ryan et al. |
| 2018/0300448 A1 | 10/2018 | Rabinowitz et al. |
| 2019/0010543 A1 | 1/2019 | Babiarz et al. |
| 2019/0106737 A1 | 4/2019 | Underhill |
| 2019/0106751 A1 | 4/2019 | Zimmermann et al. |
| 2019/0185913 A1 | 6/2019 | Zimmermann et al. |
| 2019/0185936 A1 | 6/2019 | Babiarz et al. |
| 2019/0194758 A1 | 6/2019 | Babiarz et al. |
| 2019/0194759 A1 | 6/2019 | Babiarz et al. |
| 2019/0203290 A1 | 7/2019 | Rabinowitz et al. |
| 2019/0203294 A1 | 7/2019 | Babiarz et al. |
| 2019/0211391 A1 | 7/2019 | Rabinowitz et al. |
| 2019/0211392 A1 | 7/2019 | Rabinowitz et al. |
| 2019/0211393 A1 | 7/2019 | Rabinowitz et al. |
| 2019/0211399 A1 | 7/2019 | Rabinowitz et al. |
| 2019/0211402 A1 | 7/2019 | Babiarz et al. |
| 2019/0211406 A1 | 7/2019 | Babiarz et al. |
| 2019/0249241 A1 | 8/2019 | Rabinowitz et al. |
| 2019/0256894 A1 | 8/2019 | Zimmermann et al. |
| 2019/0256906 A1 | 8/2019 | Rabinowitz et al. |
| 2019/0256907 A1 | 8/2019 | Ryan et al. |
| 2019/0256908 A1 | 8/2019 | Rabinowitz et al. |
| 2019/0256909 A1 | 8/2019 | Rabinowitz et al. |
| 2019/0256912 A1 | 8/2019 | Rabinowitz et al. |
| 2019/0256916 A1 | 8/2019 | Babiarz et al. |
| 2019/0256917 A1 | 8/2019 | Babiarz et al. |
| 2019/0256919 A1 | 8/2019 | Babiarz et al. |
| 2019/0256931 A1 | 8/2019 | Babiarz et al. |
| 2019/0264277 A1 | 8/2019 | Rabinowitz et al. |
| 2019/0264280 A1 | 8/2019 | Rabinowitz et al. |
| 2019/0264288 A1 | 8/2019 | Rabinowitz et al. |
| 2019/0271043 A1 | 9/2019 | Babiarz et al. |
| 2019/0276888 A1 | 9/2019 | Rabinowitz et al. |
| 2019/0284623 A1 | 9/2019 | Rabinowitz et al. |
| 2019/0300950 A1 | 10/2019 | Rabinowitz et al. |

(56) References Cited

U.S. PATENT DOCUMENTS

| | | | |
|---|---|---|---|
| 2019/0309358 | A1 | 10/2019 | Rabinowitz et al. |
| 2019/0309359 | A1 | 10/2019 | Zimmermann et al. |
| 2019/0309365 | A1 | 10/2019 | Babiarz et al. |
| 2019/0316177 | A1 | 10/2019 | Zimmermann et al. |
| 2019/0316184 | A1 | 10/2019 | Zimmermann et al. |
| 2019/0316200 | A1 | 10/2019 | Rabinowitz et al. |
| 2019/0323076 | A1 | 10/2019 | Rabinowitz et al. |
| 2019/0360036 | A1 | 11/2019 | Rabinowitz et al. |
| 2020/0024653 | A1 | 1/2020 | Bethke |

FOREIGN PATENT DOCUMENTS

| | | | |
|---|---|---|---|
| CN | 101675169 | A | 3/2010 |
| EP | 0270017 | A2 | 6/1988 |
| EP | 1524321 | A1 | 4/2005 |
| EP | 1524321 | B1 | 7/2009 |
| EP | 2163622 | A1 | 3/2010 |
| EP | 2128169 | A1 | 12/2010 |
| EP | 2902500 | A1 | 8/2015 |
| EP | 3285193 | A1 | 2/2018 |
| GB | 2488358 | | 8/2012 |
| JP | 2965699 | | 8/1999 |
| JP | 2002-530121 | A | 9/2002 |
| JP | 2004502466 | A | 1/2004 |
| JP | 2004533243 | A | 11/2004 |
| JP | 2005514956 | A | 5/2005 |
| JP | 2005160470 | A | 6/2005 |
| JP | 2006-254912 | A | 9/2006 |
| JP | 2011/516069 | A | 5/2011 |
| RU | 2290078 | C1 | 12/2006 |
| WO | 179851 | A1 | 10/2001 |
| WO | 200190419 | A2 | 11/2001 |
| WO | 2002004672 | A2 | 1/2002 |
| WO | 2002055985 | A2 | 7/2002 |
| WO | 2002076377 | | 10/2002 |
| WO | 02/090505 | A2 | 11/2002 |
| WO | 2003031646 | A1 | 4/2003 |
| WO | 3050532 | A1 | 6/2003 |
| WO | 2003062441 | A1 | 7/2003 |
| WO | 0190419 | A9 | 11/2003 |
| WO | 3102595 | A1 | 12/2003 |
| WO | 3106623 | A2 | 12/2003 |
| WO | 2004087863 | A2 | 10/2004 |
| WO | 2005021793 | A1 | 3/2005 |
| WO | 2005035725 | A2 | 4/2005 |
| WO | 2005100401 | A2 | 10/2005 |
| WO | 2005123779 | A2 | 12/2005 |
| WO | 2007057647 | A1 | 5/2007 |
| WO | 2007062164 | A3 | 5/2007 |
| WO | 2007070482 | A2 | 6/2007 |
| WO | 2007/117256 | A1 | 10/2007 |
| WO | 2007132167 | A2 | 11/2007 |
| WO | 2007/147076 | A2 | 12/2007 |
| WO | 2007147074 | A2 | 12/2007 |
| WO | 2008024473 | A2 | 2/2008 |
| WO | 2008048931 | A1 | 4/2008 |
| WO | 2008051928 | A2 | 5/2008 |
| WO | 2008059578 | A1 | 5/2008 |
| WO | 2008081451 | A2 | 7/2008 |
| WO | 2008115497 | A2 | 9/2008 |
| WO | 2008135837 | A2 | 11/2008 |
| WO | 2008157264 | A2 | 12/2008 |
| WO | 2009009769 | A2 | 1/2009 |
| WO | 2009013492 | A1 | 1/2009 |
| WO | 2009013496 | A1 | 1/2009 |
| WO | 2009019215 | A1 | 2/2009 |
| WO | 2009019455 | A2 | 2/2009 |
| WO | 2009/036525 | A2 | 3/2009 |
| WO | 2009030100 | A1 | 3/2009 |
| WO | 2009032779 | A2 | 3/2009 |
| WO | 2009032781 | A2 | 3/2009 |
| WO | 2009033178 | A1 | 3/2009 |
| WO | 2009091934 | A1 | 7/2009 |
| WO | 2009092035 | A2 | 7/2009 |
| WO | 2009105531 | A1 | 8/2009 |
| WO | 2009146335 | A1 | 12/2009 |
| WO | 2010017214 | A1 | 2/2010 |
| WO | 2010/033652 | A1 | 3/2010 |
| WO | 2010075459 | | 7/2010 |
| WO | 2011041485 | A1 | 4/2011 |
| WO | 2011/057061 | A1 | 5/2011 |
| WO | 2011057094 | | 5/2011 |
| WO | 2011/090556 | A1 | 7/2011 |
| WO | 2011087760 | | 7/2011 |
| WO | 2011146632 | A1 | 11/2011 |
| WO | 2012/019200 | A2 | 2/2012 |
| WO | 2012/028746 | A1 | 3/2012 |
| WO | 201283250 | | 6/2012 |
| WO | 2012088456 | A2 | 6/2012 |
| WO | 20120071621 | | 6/2012 |
| WO | 2012108920 | A1 | 8/2012 |
| WO | 2012/142531 | A2 | 10/2012 |
| WO | 2007/149791 | A2 | 12/2012 |
| WO | 2013030577 | | 3/2013 |
| WO | 2013/045432 | A1 | 4/2013 |
| WO | 2013/049892 | A1 | 4/2013 |
| WO | 2013052557 | A2 | 4/2013 |
| WO | 2013/086464 | A1 | 6/2013 |
| WO | 20130130848 | | 9/2013 |
| WO | 2013/159035 | A2 | 10/2013 |
| WO | 2013/169339 | A1 | 11/2013 |
| WO | 2013/177220 | A1 | 11/2013 |
| WO | 2013/181651 | A1 | 12/2013 |
| WO | 2014/004726 | A1 | 1/2014 |
| WO | 2014/014497 | A1 | 1/2014 |
| WO | 20140018080 | | 1/2014 |
| WO | 2014/035986 | A1 | 3/2014 |
| WO | 2014/122288 | A1 | 8/2014 |
| WO | 2014/149134 | A2 | 9/2014 |
| WO | 2014/151117 | A1 | 9/2014 |
| WO | 2015/100427 | A1 | 7/2015 |
| WO | 2015/148494 | A1 | 10/2015 |
| WO | 2015/164432 | A1 | 10/2015 |
| WO | 2016/009059 | A1 | 1/2016 |
| WO | 2016/065295 | A1 | 4/2016 |
| WO | 2016/077313 | A1 | 5/2016 |
| WO | 2016/138080 | A1 | 9/2016 |
| WO | 2016/193490 | A1 | 12/2016 |
| WO | 2017/058784 | A1 | 4/2017 |
| WO | 2017/181146 | A1 | 10/2017 |
| WO | 2017/181202 | A2 | 10/2017 |
| WO | 2017205540 | A1 | 11/2017 |
| WO | 2018/083467 | A1 | 5/2018 |
| WO | 2018/106798 | A1 | 6/2018 |
| WO | 2018/156418 | A1 | 8/2018 |
| WO | 2019/140298 | A1 | 7/2019 |
| WO | 2019/161244 | A1 | 8/2019 |
| WO | 2019/200228 | A1 | 10/2019 |
| WO | 2019/241349 | A1 | 12/2019 |
| WO | 2020/010255 | A1 | 1/2020 |
| WO | 2020/018522 | A1 | 1/2020 |

OTHER PUBLICATIONS

Cheung, S. W. et al., "Rapid Publication: Microarray-Based CGH Detects Chromosomal Mosaicism Not Revealed by Conventional Cytogenetics", American Journal of Medical Genetics Part A, vol. 143A, 2007, 1679-1686.

Conlin, L. K. et al., "Mechanisms of mosaicism, chimerism and uniparental disomy identified by single nucleotide polymorphism array analysis", Human Molecular Genetics, vol. 19, No. 7, Jan. 6, 2010, 1263-1275.

Coombes, R. C. , "Abstract P4-01-02: Early detection of residual breast cancer through a robust, scalable and personalized analysis of circulating tumour DNA (ctDNA) antedates overt metastatic recurrence", Cancer Research, vol. 79, No. 4 Supplement, Feb. 15, 2019.

Deng, S. et al., "TNER: A Novel Background Error Suppression Method for Mutation Detection in Circulating Tumor DNA", bioRxiv, http://dx.doi.org/10.1101/214379, Nov. 5, 2017, 12 pgs.

Donaghue, C. et al., "Detection of mosaicism for primary trisomies in prenatal samples by QF-PCR and karyotype analysis", Prenatal Diagnosis, vol. 25, 2005, 65-72.

(56) References Cited

OTHER PUBLICATIONS

Forshew, T. et al., "Supplementary Materials for Noninvasive Identification and Monitoring of Cancer Mutations by Targeted Deep Sequencing of Plasma DNA", Sci. Transl. Med, vol. 4, May 30, 2012, 20 pgs.

Han, S-W et al., "Predictive and Prognostic Impact of Epidermal Growth Factor Receptor Mutation in Non-Small-Cell Lung Cancer Patients Treated With Gefitinib", Journal of Clinical Oncology, vol. 23, No. 11, Apr. 10, 2005, 2493-2501.

Kunishima, S. et al., "First description of somatic mosaicism in MYH9 disorders", British Journal of Haematology, vol. 128, 2005, 360-365.

Lo, Y-M D. , "Non-invasive prenatal diagnosis using fetal cells in maternal blood", J. Clin. Pathol., vol. 47, 1994, 1060-1065.

Magbanua, M. J. et al., "Abstract PD2-01: Personalized serial circulating tumor DNA (ctDNA) analysis in high-risk early stage breast cancer patients to monitor and predict response to neoadjuvant therapy and outcome in the I-SPY 2 Trial", Cancer Research, vol. 79, No. 4 Supplement, Feb. 15, 2019.

Mardis, E. R. , "The impact of next-generation sequencing technology on genetics", Trends in Genetics, vol. 24, No. 3, Feb. 11, 2008, 133-141.

McDonald, B. R. et al., "Abstract P4-01-21: Multiplexed targeted digital sequencing of circulating tumor DNA to detect minimal residual disease in early and locally advanced breast cancer", Cancer Research, vol. 79, No. 4 Supplement, Feb. 15, 2019.

Mertes, F. et al., "Targeted enrichment of genomic DNA regions for next-generation sequencing", Briefings in Functional Genomics, vol. 10, No. 6, Nov. 26, 2011, 374-386.

Newman, A. M. et al., "Integrated digital error suppression for improved detection of circulating tumor DNA", Nature Biotechnology, vol. 34, No. 5, May 2016, 547-555.

Nguyen-Dumont, T. , "A high-plex PCR approach for massively parallel sequencing", BioTechniques, vol. 55, No. 2, Aug. 2013, 69-74.

Papadopoulou, E. et al., "Cell-Free DNA and RNA in Plasma as a New Molecular Marker for Prostate Cancer", Oncology Research, vol. 14, 2004, 439-445.

Poirier, K. et al., "Maternal mosaicism for mutations in the ARX gene in a family with X linked mental retardation", Human Genetics, vol. 118, Aug. 3, 2005, 45-48.

Poon, L. L. et al., "Differential DNA Methylation between Fetus and Mother as a Strategy for Detecting Fetal DNA in Maternal Plasma", Clinical Chemistry, vol. 48, No. 1, 2002, 35-41.

Saker, A. et al., "Genetic characterisation of circulating fetal cells allows non-invasive prenatal diagnosis of cystic fibrosis", Prenatal Diagnosis, vol. 26, Jul. 11, 2006, 906-916.

Sigdel, T. et al., "Plasma Donor-Derived Cell-Free DNA Quantification by massively multiplex PCR Distinguishes Kidney Transplant Acute Rejection", Transplantation, vol. 102, No. 7S, Jul. 2018, S178-S179.

Sigdel, T. K. et al., "Optimizing Detection of Kidney Transplant Injury by Assessment of Donor-Derived Cell-Free DNA via Massively Multiplex PCR", Journal of Clinical Medicine, vol. 8, No. 19, Dec. 23, 2018, 17 pages.

Wikipedia, "Buffy coat", Retrieved from "https://en.wikipedia.org.Jw/index.php?title=Buffy_coat&oldid=900992886", Jun. 9, 2019, 2 pgs.

Alberts, B. et al., "Chapter 20: Germ Cells and Fertilization", Molecular Biology of the Cell, Fourth Edition, 2002, 1127-1156.

Alberts, B. et al., "Chapter 4: DNA and Chromosomes", Molecular Biology of the Cell, Fourth Edition, 2002, 191-234.

Antonarakis, S. E. et al., "Chromosome 21 and Down Syndrome: From Genomics to Pathophysiology", Nature Reviews Genetics, vol. 5, Oct. 2004, 725-738.

Beroud, C. et al., "Prenatal diagnosis of spinal muscular atrophy by genetic analysis of circulating fetal cells", The Lancet, vol. 361, Mar. 22, 2003, 1013-1014.

Bianchi, D. W. , "Circulating Fetal DNA: Its Origin and Diagnostic Potential—A Review", Placenta, vol. 25, Supplemental A, May 2004, S93-S101.

Bianchi, D. W. , "Review: Fetal Cells in the Maternal Circulation: Feasibility for Prenatal Diagnosis", British Journal of Haematology, vol. 105, 1999, 574-583.

Butt, A. N. et al., "Overview of Circulating Nucleic Acids in Plasma/Serum: Update on Potential Prognostic and Diagnostic Value in Diseases Excluding Fetal Medicine and Oncology", Ann. N.Y. Acad. Sci., vol. 1137, 2008, 236-242.

Dietmaier, W. et al., "Multiple Mutation Analyses in Single Tumor Cells with Improved Whole Genome Amplification", American Journal of Pathology, vol. 154, No. 1, Jan. 1999, 83-95.

Everitt, B. S. , "Medical Statistics From A to Z", 2003, 3 pages.

Hartwell, L. H. et al., "Chapter 11: The Direct Detection of Genotype Distinguishes Individual Genomes", Genetics: From Genes to Genomes, Second Edition, 2004, 371-414.

Hartwell, L. H. et al., "Chapter 13: Chromosomal Rearrangements and Changes in Chromosome Number Reshape Eukaryotic Genomes", Genetics: From Genes to Genomes, Second Edition, 2004, 441-486.

Hattori, M. et al., "The DNA sequence of human chromosome 21", Nature, vol. 405, May 18, 2000, 311-319.

Illumina, , "Petition for Inter Partes Review of U.S. Pat. No. 8,682,592", Jun. 13, 2019, 91 pages.

Illumina, Inc., , "Declaration of David Peters, Ph.D. In Support of Petition for Inter Partes Review of U.S. Pat. No. 8,682,592", Jun. 13, 2019, 136 pages.

*Illumina, Inc. V. Natera, Inc.* "Order Re: Claim Construction", Jan. 30, 2019, 16 pgs.

Kamat, A. A. et al., "Quantification of total plasma cell-free DNA in ovarian cancer using real-time PCR", Ann N Y Acad Sci., vol. 1075, Sep. 2006, 230-234.

Lui, Y. Y. et al., "Predominant Hematopoietic Origin of Cell-Free DNA in Plasma and Serum after Sex-Mismatched Bone Marrow Transplantation", Clinical Chemistry, vol. 48, vol. 3, 2002, 421-427.

Munne, S. et al., "Improved implantation after preimplantation genetic diagnosis of aneuploidy", Reproductive BioMedicine Online, vol. 7., No. 1., May 15, 2003, 91-97.

Natera, Inc., , "Declaration of Sandra L. Haberny", May 16, 2019, 3 pages.

Natera, Inc., , "Exhibits A-H to Haberny Declaration", May 16, 2019, 192 pages.

Natera, Inc., , "Motion to Dismiss", May 16, 2019, 2 pages.

Natera, Inc., , "Natera Inc.'s First Amended Answer, Affirmative Defenses and Counterclaims", Aug. 16, 2018, 28 pages.

Natera, Inc. "Natera, Inc.'s Supplemental Objections and Response to Plaintiff Illumina, Inc.'s Interrogatory No. 8", Mar. 20, 2019, 29 pages.

Natera, Inc., , "Opening Brief in Support of Motion to Dismiss", May 16, 2019, 26 pages.

Ng, S. B. et al., "Individualised multiplexed circulating tumour DNA assays for monitoring of tumour presence in patients after colorectal cancer surgery", Scientific Reports, vol. 7, No. 40737, Jan. 19, 2017, 11 pages.

Pastinen, T. et al., "Minisequencing: A Specific Tool for DNA Analysis and Diagnostics on Oligonucleotide Arrays", Genome Research, vol. 7, 1997, 606-614.

Peters, D. , "List of Materials Considered by David Peters, Ph.D.", Jun. 13, 2019, 2 pages.

Reinert, T. et al., "Analysis of circulating tumour DNA to monitor disease burden following colorectal cancer surgery", Gut, vol. 65, 2016, 625-634.

Riva, F. , "Patient-Specific Circulating Tumor DNA Detection during Neoadjuvant Chemotherapy in Triple-Negative Breast Cancer", Clinical Chemistry, vol. 63, No. 3, 2017, 691-699.

Sham, P. et al., "DNA Pooling: A Tool for Large-Scale Association Studies", Nature Reviews Genetics, vol. 3, Nov. 2002, 862-871.

Snyder, T. M. et al., "Universal noninvasive detection of solid organ transplant rejection", PNAS, vol. 108, No. 15, Apr. 12, 2011, 6229-6234.

The International Hapmap Consort, , "The International HapMap Project", Nature, vol. 426, Dec. 18, 2003, 789-796.

(56) References Cited

OTHER PUBLICATIONS

Tiersch, T. R. et al., "Reference Standards for Flow Cytometry and Application in Comparative Studies of Nuclear DNA Content", Cytometry, vol. 10, Mar. 21, 1989, 706-710.
Wang, D. G. et al., "Large-Scale Identification, Mapping, and Genotyping of Single-Nucleotide Polymorphisms in the Human Genome", Science, vol. 280, May 15, 1998, 1077-1082.
Weiss, C. A., "Chapter 8: Confidence Intervals for One Population Mean", Introductory Statistics, Sixth Edition, 2002, 340-381.
Wong, K. K. et al., "Allelic imbalance analysis by high-density single nucleotide polymorphic allele (SNP) array with whole genome amplified DNA", Nucleic Acids Research, vol. 32, No. 9, May 17, 2004, 8 pages.
Zhang, L. et al., "Whole genome amplification from a single cell: Implications for genetic analysis", Proc Nat'l. Acad. Sci. USA, vol. 89, Jul. 1992, 5847-5851.
"Blast of AAAAAAAAATTTAAAAAAAAATTT(http://blast.ncbi.nlm.nih.gov/Blast.cgi, downloaded May 4, 2015)".
"Db SNP rs2056688 (http://www.ncbi.nlm.nih.gov/projects/SNP/snp_ref.cgi?rs=2056688, downloaded May 4, 2015".
"Declaration by Dr. Zimmerman of Oct. 30, 2014 filed in U.S. Appl. No. 14/044,434".
"European Application No. 014198110, European Search Report dated Apr. 28, 2015, 3 pages."
"Finishing the Euchromatic Sequence of the Human Genome", Nature vol. 431,(Oct. 21, 2004),931-945.
"FixedMedium, dictionary definition, Academic Press Dictionary of Science andTechnology", Retrieved from the Internet: <URL:www.credoreference.com/entry/apdst/fixed_medium>, 1996, 1 pg.
"GeneticsHome Reference", http://ghr.nlm.nih.gov/handbook/genomicresearch/snp, Feb. 28, 2014, 1-2.
"Ion Ampli Seq Comprehensive Cancer Panel, product brochure, Life TechnologiesCorporation. Retrieved from the Internet", <URL:https://tools.lifetechnologies.com/content/sfs/brochures/Ion_CompCancerPanel_Flyer.pdf>, 2012, 2 pgs.
"Merriam-Webster.com (http://www.merriam-webster.com/dictionary/universal, downloaded Jul. 23, 2014)".
"Multiplexing with RainDrop Digital PCR", RainDance Technologies, Application Note, 2013, 1-2.
"NucleicAcids, Linkers and Primers: Random Primers", New England BioLabs 1998/99Catalog, 1998, 121 and 284.
"Primer3, information sheet, Sourceforge.net. [retrieved on Nov. 12, 2012]. Retrieved from the Internet: <URL: http://primer3.sourceforge.net/>", 2009, 1 pg.
"www.fatsecret.com" (printed from internet Nov. 1, 2014).
PRNewswire (Research Suggests Daily Consumption of Orange Juice Can Reduce Blood Pressure and May Provide Beneficial Effects to Blood Vessel Function: New Study Identified Health Benefits in Orange Juice, Dec. 8, 2010).
The Bump (Panorama Test, attached, Jul. 1, 2013).
What to Expect (Weird Harmony results, attached, May 1, 2015).
Wikipedia (attached, available at https://en.wikipedia.org/wiki/Stimulant, accessed Mar. 14, 2016).
"Guideline related to genetic examination", Societies Related to Genetic Medicine, Japanese Society for Genetic Counseling, Japanese Society for Gene Diagnosis and Therapy, Japan Society of Obstetrics and Gynecology, 2003, 2-15.
"How Many Carbs in a Potato?, [Online]", Retrieved from the Internet: <http://www.newhealthguide.org/How-Many-Carbs-In-A-Potato.html>, Nov. 1, 2014, 3 pages.
"Random variable", In the Penguin Dictionary of Mathematics. Retrieved from http://www.credoreference.com/entry/penguinmath/random _variable, 2008, 1 page.
Abbosh, C. et al., "Phylogenetic ctDNA analysis depicts early-stage lung cancer evolution", Nature, vol. 545, May 25, 2017, 446-451.
Abidi, S. et al., "Leveraging XML-based electronic medical records to extract experiential clinical knowledge: An automated approach to generate cases for medical case-based reasoning systems", International Journal of Medical Informatics, 68(1-3), 2002, 187-203.

Agarwal, Ashwin. et al., "Commercial Landscape of Noninvasive Prenatal Testing in the United States", Prenatal Diagnosis,33, 2013, 521-531.
Alaeddini, R. et al., "Forensic implications of genetic analyses from degraded DNA—A review", Forensic Science International: Genetics, vol. 4, 2010, 148-157.
Alkan, Can et al., "Personalized Copy Number and Segmental Duplication Maps Using Next-Generation Sequencing", Nature Genetics, 41, 10, 2009, 1061-1068.
Allaire, F R., "Mate selection by selection index theory", Theoretical Applied Genetics, 57(6), 1980, 267-272.
Allawi, Hatim T. et al., "Thermodynamics of internal C•T Mismatches in DNA", Nucleic Acids Research, 26 (11), 1998, 2694-2701.
Anker, P. et al., "Detection of circulating tumour DNA in the blood (plasma/serum) of cancer patients", Cancer and Metastasis Reviews, vol. 18, 1999, 65-73.
Aoki, Yasuhiro , "Statistical and Probabilistic Bases of Forensic DNA Testing", The Journal of the Iwate Medical Association, 2002, vol. 54, p. 81-94.
Ashoor, G. et al., "Fetal fraction in maternal plasma cell-free DNA at 11-13 weeks' gestation: relation to maternal and fetal characteristics", Ultrasound in Obstetrics and Gynecology, vol. 41, 2013, 26-32.
Ashoor, Ghalia et al., "Chromosome-Selective Sequencing of Maternal Plasma Cell-Free DNA for First-Trimester Detection of Trisomy 21 and Trisomy 18", American Journal of Obstetrics & Gynecology, 206, 2012, 322.e1-322.e5.
Ashoor, Ghalia et al., "Fetal Fraction in Maternal Plasma Cell-Free DNA at 11-13 Weeks' Gestation: Effect of Maternal and Fetal Factors", Fetal Diagnosis Therapy, 2012, 1-7.
Bada, Michael A. et al., "Computational Modeling of Structural Experimental Data", Methods in Enzymology,317, 2000, 470-491.
Beaumont, Mark A et al., "The Bayesian Revolution in Genetics", Nature Reviews Genetics, 5, 2004, 251-261.
Beer, Alan E. et al., "The Biological Basis of Passage of Fetal Cellular Material into the Maternal Circulation", Annals New York Academy of Sciences, 731, 1994, 21-35.
Beerenwinkel, et al., "Methods for Optimizing Antiviral Combination Therapies", Bioinformatics, 19(1), 2003, i16-i25.
Beerenwinkel, N. et al., "Geno2pheno: estimating phenotypic drug resistance from HIV-1 genotypes", Nucleic Acids Research, 31(13), 2003, 3850-3855.
Benn, P. et al., "Non-Invasive Prenatal Testing for Aneuploidy: Current Status and Future Prospects", Ultrasound Obstet Gynecol, 42, 2013, 15-33.
Benn, P et al., "Non-Invasive prenatal Diagnosis for Down Syndrome: the Paradigm Will Shift, but Slowly", Ultrasound Obstet. Gynecol., 39, 2012, 127-130.
Bentley, David R et al., "Accurate Whole Human Genome Sequencing Using Reversible Terminator Chemistry", Nature, 456, 6, 2008, 53-59.
Bermudez, M. et al., "Single-cell sequencing and mini-sequencing for preimplantation genetic diagnosis", Prenatal Diagnosis, 23, 2003, 669-677.
Bevinetto, Gina , Bevinetto (5 Foods All Pregnant Women Need, American Baby, available at http://www.parents.com/pregnancy/mybody/nutrition/5greatpregnancyfoods/, Apr. 15, 2008).
Bianchi, D W. et al., "Fetal gender and aneuploidy detection using fetal cells maternal blood: analysis of NIFTY I data", Prenat Diagn 2002; 22, 2002, 609-615.
Bianchi, D. W. et al., "Genome-Wide Fetal Aneuploidy Detection by Maternal Plasma DNA Sequencing", Obstetrics & Gynecology, vol. 119, No. 5, May 2012, 890-901.
Birch, Lyndsey et al., "Accurate and Robust Quantification of Circulating Fetal and Total DNA in Maternal Plasma from 5 to 41 Weeks of Gestation", Clinical Chemistry, 51(2), 2005, 312-320.
Bisignano, et al., "PGD and Aneuploidy Screening for 24 Chromosomes: Advantages and Disadvantages of Competing Platforms", Reproductive BioMedicine Online, 23, 2011, 677-685.
Bodenreider, O. , "The Unified Medical Language System (UMLS): Integrating Biomedical Terminology", Nucleic Acids Research, 32, (Database issue), 2004, D267-D270.

(56) References Cited

OTHER PUBLICATIONS

Breithaupt, Holger, "The Future of Medicine", EMBO Reports, 21(61), 2001, 465-467.
Brownie, Jannine et al., "The Elimination of Primer-Dimer Accumulation in PCR", Nucleic Acids Research, 25(16), 1997, 3235-3241.
Butler, J. et al., "The Development of Reduced Size STR Amplicons as Tools for Analysis of Degraded DNA*", Journal of Forensic Sciences, vol. 48, No. 5, 2003, 1054-1064.
Cairns, Paul et al., "Homozygous Deletions of 9p21 in Primary Human Bladder Tumors Detected by Comparative Multiplex Polymerase Chain Reaction", Cancer Research, 54, 1994, 1422-1424.
Caliendo, Angela, "Multiplex PCR and Emerging Technologies for the Detection of Respiratory Pathogens", Clinical Infectious Diseases, 52(4), 2011, S326-S330.
Cansar,, "HS-578-T—Copy Number Variation—Cell Line Synopsis", ICR Cancer Research UK, Retrieved on Mar. 26, 2018 from https://cansar.icr.ac.uk/cansar/cell-lines/Hs-578-T/copy_number_variation/chromosome_8/, Mar. 26, 2018, 50 pgs.
Carnevale, Alessandra et al., "Attitudes of Mexican Geneticists Towards Prenatal Diagnosis and Selective Abortion", American Journal of Medical Genetics, 75, 1998, 426-431.
Carvalho, B. et al., "Exploration, normalization, and genotype calls of high-density oligonucleotide SNP array data", Biostatistics, vol. 8, No. 2, 2007, 485-499.
Casbon, J. A. et al., "A method for counting PCR template molecules with application to next-generation sequencing", Nucleic Acids Research, vol. 39, No. 12, Apr. 13, 2011, 1-8.
Chakraborty, R. et al., "Paternity Exclusion by DNA Markers: Effects of Paternal Mutations", Journal of Forensic Sciences, vol. 41, No. 4, Jul. 1996, 671-677.
Chan, K.C. et al., "Size Distributions of Maternal and Fetal DNA in Maternal Plasma", Clinical Chemistry, vol. 50, No. 1, 2004, 88-92.
Chang, H.W. et al., "Assessment of Plasma DNA Levels, Allelic Imbalance, and CA 125 as Diagnostic Tests for Cancer", Journal of the National Cancer Institute, vol. 94, No. 22, Nov. 20, 2002, 1697-1703.
Chen, E. et al., "Noninvasive Prenatal Diagnosis of Fetal Trisomy 18 and Trisomy 13 by Maternal Plasma DNA Sequencing", PLoS ONE, 6 (7), e21791, 2011, 7 pgs.
Chen, X. Q. et al., "Microsatallite alterations in plasma DNA of small cell lung cancer patients", Nature Medicine, vol. 2, No. 9, Sep. 1996, 1033-1035.
Chetty, Shilpa et al., "Uptake of Noninvasive Prenatal Testing (NIPT) in Women Following Positive Aneuploidy Screening", Prenatal Diagnosis,33, 2013, 542-546.
Chiu, R. et al., "Non-Invasive Prenatal Assessment of Trisomy 21 by Multiplexed Maternal Plasma DNA Sequencing: Large Scale Validity Study", BMJ, 342, c7401, 2011, 9 pgs.
Chiu, Rossa W. et al., "Effects of Blood-Processing Protocols on Fetal and Total DNA Quantification in Maternal Plasma", Clinical Chemistry, 47(9), 2001, 1607-1613.
Chiu, Rossa W.K. et al., "Maternal Plasma DNA Analysis with Massively Parallel Sequencing by Litigation for Noninvasive Prenatal Diagnosis of Trisomy 21", Clinical Chemistry, 56, 3, 2010, 459-463.
Chiu, Rossa W.K. et al., "Non-Invasive Prenatal Diagnosis by Single Molecule Counting Technologies", Trends in Genetics, 25 (7), 2009, 324-331.
Chiu, Rossa W.K. et al., "Noninvasive Prenatal Diagnosis of Fetal Chromosomal Aneuploidy by Massively Parallel Genomic Sequencing of DNA in Maternal Plasma", PNAS, 105, 51 (with Supporting Information), 2008, 23.
Choi, M. et al., "Genetic diagnosis by whole exome capture and massively parallel DNA sequencing", PNAS, vol. 106, No. 45, Nov. 10, 2009, 19096-19101.
Chu, T. et al., "Statistical Considerations for Digital Approaches to Non-Invasive Fetal Genotyping", Bioinformatics (Advance Access publication), 26 (22), 2010, 2863-2866.
Chu, Tianjiao et al., "Statistical Model for Whole Genome Sequencing and its Application to Minimally Invasive Diagnosis of Fetal Genetic Disease", Bioinformatics, 25(10), 2009, 1244-1250.
Chu, Tianjiao. et al., "A Novel Approach Toward the Challenge of Accurately Quantifying Fetal DNA in Maternal Plasma", Prenatal Diagnosis,30, 2010, 1226-1229.
Cole, Neal W. et al., "Hyperglycemia-Induced Membrane Lipid Peroxidation and Elevated Homocysteine Levels Are Poorly Attenuated by Exogenous Folate in Embryonic Chick Brains", Comparative Biochemistry and Physiology, Part B, 150, 2008, 338-343.
Colella, S. et al., "QuantiSNP: an Objectives Bayes Hidden-Markov Model to Detect and Accurately Map Copy Number Variation Using SNP Genotyping Data", Nucleic Acids Research, 35 (6), 2007, 2013-2025.
Cossu, Gianfranco et al., "Rh D/d Genotyping by Quantitative Polymerase Chain Reaction and Capillary Zone Electrophoresis", Electrophoresis, 17, 1996, 1911-1915.
Coyle, J. F. et al., "Standards for detailed clinical models as the basis for medical data exchange and decision support", International Journal of Medical Informatics, 69(2-3), 2003, 157-174.
Craig, D. W. et al., "Identification of genetic variants using barcoded multiplexed sequencing", Nature Methods, vol. 5, Oct. 2008, 887-893.
Cross, Jillian et al., "Resolution of trisomic mosaicism in prenatal diagnosis: estimated performance of a 50K SNP microarray", Prenat Diagn 2007; 27, 2007, 1197-1204.
D'Aquila, Richard et al., "Maximizing sensitivity and specificity of PCR by pre-amplification heating", Nucleic Acids Research, 19(13), 1991, p. 3749.
Daruwala, Raoul-Sam et al., "A Versatile Statistical Analysis Algorithm to Detect Genome Copy Number Variation", PNAS, 101(46), 2004, 16292-16297.
De Bruin, E. et al., "Spatial and temporal diversity in genomic instability processes defines lung cancer evolution", Science, vol. 346, No. 6206, Oct. 10, 2014, 251-256.
De Vries, et al., "Diagnostic genome profiling in mental retardation", Am J Hum Genet, 77, published online Aug. 30, 2005, 2005, 606-616.
Deangelis, M. et al., "Solid-phase Reversible Immobilization for the Isolation of PCR Products", Nucleic Acids Research, 23 (22), 1995, 4742-4743.
Deutsch, S. et al., "Detection of aneuploidies by paralogous sequence quantification", J Med Genet, vol. 41, 2004, 908-915.
Devaney, S. et al., "Noninvasive Fetal Sex Determination Using Cell-Free Fetal DNA: A Systematic Review and Meta-analysis", JAMA, 306 (6), 2011, 627-636.
Dhallan, et al., "Methods to Increase the Percentage of Free Fetal DNA Recovered from the Maternal Circulation", JAMA, 291(9), 2004, 1114-1119.
Dhallan, Ravinder et al., "A non-invasive test for prenatal diagnosis based on fetal DNA present in maternal blood: a preliminary study", The Lancet, 369, 2007, 474-481.
Dieffenbach, C W. et al., "General concepts for PCR primer design", Genome Research. PCR methods and Applications vol. 3, 1993, S30-S37.
Ding, C et al., "Direct molecular haplotyping of long-range genomic DNA with M1-PCR", PNAS 100(13), 2003, 7449-7453.
Dodge, Y. , "Bayes' Theorem", The Concise Encyclopedia of Statistics, 2008, 30-31.
Dohm, J. et al., "Substantial Biases in Ultra-Short Read Data Sets From High-Throughput DNA Sequencing", Nucleic Acids Research, 36 (16), e105, 2008, 10 pgs.
Dolganov, Gregory et al., "A Novel Method of Gene Transcript Profiling in Airway Biopsy Homogenates Reveals Increased Expression of a Na—K+—Cl-Cotransporter (NKCC1) in Asthmatic Subjects", Genome Res.,11, 2001, 1473-1483.
Donohoe, Gerard G et al., "Rapid Single-Tube Screening of the C282Y Hemochromatosis Mutation by Real-Time Multiplex Allele-specific PCR without Fluorescent Probes", Clinical Chemistry, 46, 10, 2000, 1540-1547.
Donoso, P. et al., "Current Value of Preimplantation Genetic Aneuploidy Screening in IVF", Human Reproduction Update, 13(1), 2007, 15-25.

(56) References Cited

OTHER PUBLICATIONS

Echeverri, et al., "Caffeine's Vascular Mechanisms of Action", International Journal of Vascular Medicine vol. 2010(2010), 10 pages, Aug. 25, 2010.
Ehrich, Mathias et al., "Noninvasive Detection of Fetal Trisomy 21 by Sequencing of DNA in Maternal Blood: A Study in a Clinical Setting", American Journal of Obstetrics & Gynecology, 204, 2011, 205.e1-205.e11.
Eichler, H , "Mild Course of Fetal Rh D Haemolytic Disease due to Maternal Alloimmunisation to Paternal HLA Class I and II Antigens", Vox Sang, 68, 1995, 243-247.
Ellison, Aaron M. , "Bayesian Inference in Ecology", Ecology Letters, vol. 7, 2004, 509-520.
Ellonen, P. et al., "Development of SNP Microarray for Supplementary Paternity Testing", International Congress Series,1261, 2004, 12-14.
EP06838311.6, , "European Communication and Extended European Search Report", dated Dec. 30, 2008, 8 pgs.
EP08742125.1, "European Communication pursuant to Article 94(3) EPC and Examination Report", dated Feb. 12, 2010, 5 pgs.
Fan, et al., "Whole-genome molecular haplotyping of single cells", Nature Biotechnology, vol. 29, No. 1, Jan. 1, 2011, 51-57.
Fan, Christina H. et al., "Non-Invasive Prenatal Measurement of the Fetal Genome", Nature, doi:10.1038/nature11251, 2012, 26 pgs.
Fan, Christina H et al., "Noninvasive Diagnosis of Fetal Aneuploidy by Shotgun Sequencing DNA from Maternal Blood", PNAS, 105, 42, 2008, 16266-16271.
Fan, H. C. et al., "Microfluidic digital PCR enables rapid prenatal diagnosis of fetal aneuploidy", American Journal of Obstetrics & Gynecology, vol. 200, May 2009, 543.e1-543.e7.
Fan, H. Christina et al., "Sensitivity of Noninvasive Prenatal Detection of Fetal Aneuploidy from Maternal Plasma Using Shotgun Sequencing Is Limited Only by Counting Statistics", PLoS ONE, vol. 5, Issue 5 (e10439), May 3, 2010, 1-6.
Fan, Jian-Bing et al., "Highly Parallel Genomic Assay", Nature Reviews, 7, 2006, 632-644.
Fazio, Gennaro. et al., "Identification of RAPD Markers Linked to Fusarium Crown and Root Rot Resistance (Frl) in Tomato", Euphytica 105, 1999, 205-210.
Fiorentino, F. et al., "Development and Clinical Application of a Strategy for Preimplantation Genetic Diagnosis of Single Gene Disorders Combined with HLA Matching", Molecular Human Reproduction (Advance Access publication), 10 (6), 2004, 445-460.
Fiorentino, F et al., "Strategies and Clinical Outcome of 250 Cycles of Preimplantation Genetic Diagnosis for Single Gene Disorders", Human Reproduction, 21, 3, 2006, 670-684.
Fiorentino, Francesco et al., "Short Tandem Repeats Haplotyping of the HLA Region in Preimplantation HLA Matching", European Journal of Human Genetics, 13, 2005, 953-958.
Ford, E. et al., "A method for generating highly multiplexed ChIP-seq libraries", BMC Research Notes, vol. 7, No. 312, May 22, 2014, 1-5.
Forejt, et al., "Segmental trisomy of mouse chromosome 17: introducing an alternative model of Down's syndrome", Genomics, 4(6), 2003, 647-652.
Forshew, et al., "Noninvasive Identification and Monitoring of Cancer Mutations by Targeted Deep Sequencing of Plasma DNA", Noninvasive identification and monitoring of cancer mutations by targeted deep sequencing of plasma DNA. Sci. Transl. Med. 4, 136 30 (2012)., 1-12.
Fredriksson, et al., "Multiplex amplification of all coding sequences within 10 cancer genes by Gene-Collector", Nucleic Acids Research, 2007, vol. 35, No. 7 e47, 1-6.
Freeman, Jennifer L. et al., "Copy Number Variation: New Insights in Genome Diversity", Genome Research, 16, 2006, 949-961.
Frost, Mackenzie S et al., "Differential Effects of Chronic Pulsatile Versus Chronic Constant Maternal Hyperglycemia on Fetal Pancreatic B-Cells", Journal of Pregnancy, 2012,, Article ID 812094, 2012, 8.
Fu, G. K. et al., "Counting individual DNA molecules by the stochastic attachment of diverse labels", PNAS, vol. 108, No. 22, May 31, 2011, 9026-9031.
Fu, G. K. et al., "Digital Encoding of Cellular mRNAs Enabling Precise and Absolute Gene Expression Measurement by Single-Molecule Counting", Analytical Chemistry, vol. 86, Mar. 3, 2014, 2867-2870.
Ganshirt-Ahlert, D. et al., "Ratio of Fetal to Maternal DNA is Less Than 1 in 5000 at different Gestational Ages in Maternal Blood", Clinical Genetics,38, 1990, 38-43.
Ganshirt-Ahlert, D. et al., "Fetal DNA in Uterine Vein Blood", Obstetrics & Gynecology, 80 (4), 1992, 601-603.
Ganshirt-Ahlert, Dorothee et al., "Three Cases of 45,X/46,XYnf Mosaicism", Human Genetics, 76, 1987, 153-156.
Garcia-Murillas, I. et al., "Mutation tracking in circulating tumor DNA predicts relapse in early breast cancer", Science Translational Medicine, vol. 7, No. 302, Aug. 26, 2015, 1-2.
Gardina, P. et al., "Ploidy Status and Copy Number Aberrations in Primary Glioblastomas Defined by Integrated Analysis of Allelic Ratios, Signal Ratios and Loss of Heterozygosity Using 500K SNP Mapping Arrays", BMC Genomics, 9 (489), (doi:10.1186/1471-2164-9-489), 2008, 16 pgs.
Geiss, G. K. et al., "Direct multiplexed measurement of gene expression with color-coded probe pairs", Nature Biotechnology, vol. 26, No. 3, Feb. 17, 2008, 317-325.
Ghanta, Sujana et al., "Non-Invasive Prenatal Detection of Trisomy 21 Using Tandem Single Nucleotide Polymorphisms", PLoS ONE, 5 (10), 2010, 10 pgs.
Gjertson, David W. et al., "Assessing Probability of Paternity and the Product Rule in DNA Systems", Genetica, 96, 1995, 89-98.
Greenwalt, T. et al., "The Quantification of Fetomaternal Hemorrhage by an Enzyme-Linked Antibody Test with Glutaraldehyde Fixation", Vox Sang, 63, 1992, 268-271.
Guerra, J. , "Terminal Contributions for Duplex Oligonucleotide Thermodynamic Properties in the Context of Nearest Neighbor Models", Biopolymers, 95(3), (2010), 2011, 194-201.
Guetta, Esther et al., "Analysis of Fetal Blood Cells in the Maternal Circulation: Challenges, Ongoing Efforts, and Potential Solutions", Stem Cells and Development, 13, 2004, 93-99.
Guichoux, et al., "Current Trends in Microsatellite Genotyping", Molecular Ecology Resources, 11, 2011, 591-911.
Gunderson, K. L. et al., "A genome-wide scalable SNP genotyping assay using microarray technology", Nature Genetics, vol. 37, No. 5, May 2005, 549-554.
Hall, M. , "Panorama Non-Invasive Prenatal Screening for Microdeletion Syndromes", Apr. 1, 2014 (Apr. 1, 2014), XP055157224, Retrieved from the Internet: URL:http://www.panoramatest.com/sites/default/files/files/PanoramaMicr odeletionsWhite Paper-2.pdf [retrieved on Dec. 8, 2014].
Handyside, et al., "Isothermal whole genome amplification from single and small numbers of cells: a new era for preimplantation genetic diagnosis of inherited disease", Molecular Human Reproduction vol. IO, No. 10 pp. 767-772, 2004.
Hara, Eiji et al., "Subtractive eDNA cloning using oligo(dT)3o-latex and PCR: isolation of eDNA clones specific to undifferentiated human embryonal carcinoma cells", Nucleic Acids Research, 19(25), 1991, 7097-7104.
Hardenbol, P. , "Multiplexed Genotyping With Sequence-Tagged Molecular Inversion Probes", Nature Biotechnology, 21 (6), 2003, 673-678.
Hardenbol, Paul et al., "Highly multiplexed molecular inversion probe genotyping: Over 10,000 targeted SNPs genotyped in a singled tube assay", Genome Research, 15, 2005, 269-275.
Harismendy, O. et al., "Method for Improving Sequence Coverage Uniformity of Targeted Genomic Intervals Amplified by LR-PCR Using Illumina GA Sequencing-By-Synthesis Technology", Bio Techniques, 46(3), 2009, 229-231.
Harper, J. C. et al., "Recent Advances and Future Developments in PGD", Prenatal Diagnosis, 19, 1999, 1193-1199.
Harton, G.L. et al., "Preimplantation Genetic Testing for Marfan Syndrome", Molecular Human Reproduction, 2 (9), 1996, 713-715.
Hawkins, T. et al., "Whole genome amplification—applications and advances", Current Opinion in Biotechnology, 13, 2002, 65-67.

(56) References Cited

OTHER PUBLICATIONS

Hayden, et al., "Multiplex-Ready PCR: A new method for multiplexed SSR and SNP genotyping", BMC Genomics 2008, 9(80), 1-12.
Hellani, A. et al., "Clinical Application of Multiple Displacement Amplification in Preimplantation Genetic Diagnosis", Reproductive BioMedicine Online, 10 (3), 2005, 376-380.
Hellani, Ali et al., "Multiple displacement amplification on single cell and possible PGD applications", Molecular Human Reproduction, 10(11), 2004, 847-852.
Hojsgaard, S. et al., "BIFROST—Block recursive models induced from relevant knowledge, observations, and statistical techniques", Computational Statistics & Data Analysis, 19(2), 1995, 155-175.
Hollas, B. et al., "A stochastic approach to count RN A molecules using DNA sequencing methods", Lecture Notes in Computer Science, vol. 2812, 2003, 55-62.
Holleley, et al., "Multiplex Manager 1.0: a Cross-Platform Computer Program that Plans and Optimizes Multiplex PCR", BioTechniques46:511-517 (Jun. 2009), 511-517.
Hollox, E. et al., "Extensive Normal Copy Number Variation of a β-Defensin Antimicrobial-Gene Cluster", Am. J. Hum. Genet., 73, 2003, 591-600.
Homer, et al., "Resolving Individuals Contributing Trace Amounts of DNA to Highly Complex Mixtures Using High-Density SNP Genotyping Microarrays", PLOS Genetics, 4(8), 2008, 9 pgs.
Hoogendoorn, Bastiaan et al., "Genotyping Single Nucleotide Polymorphisms by Primer Extension and High Performance Liquid Chromatography", Hum Genet, 104, 1999, 89-93.
Hornak, M. et al., "Aneuploidy Detection in Pigs Using Comparative Genomic Hybridization: From the Oocytes to Blastocysts", PLoS ONE, vol. 7, No. 1, Jan. 2012, 6 pages.
Hospital, F. et al., "A General Algorithm to Compute Multilocus Genotype Frequencies Under Various Mating Systems" vol. 12, No. 6, Jan. 1, 1996 (Jan. 1, 1996), pp. 455-462.
Howie, et al., "Fast and accurate genotype imputation in genome-wide association studies through pre-phasing", Nature Genetics, vol. 44, No. 8, Jul. 22, 2012, 955-959.
Hu, Dong Gui et al., "Aneuploidy Detection in Single Cells Using DNA Array-Based Comparative Genomic Hybridization", Molecular Human Reproduction, 10(4), 2004, 283-289.
Hug, H. et al., "Measurement of the number of molecules of a single mRNA species in a complex mRNA preparation", J. Theor. Biol., vol. 221, 2003, 615-624.
Hultin, E. et al., "Competitive enzymatic reaction to control allele-specific extensions", Nucleic Acids Research, vol. 33, No. 5, Mar. 14, 2005, 1-10.
Ido, Yasuo et al., "Hyperglycemia-Induced Apoptosis in Human Umbilical Vein Endothelial Cells: Inhibition by the AMP-Activated Protein Kinase Activation", Diabetes, 51, 2002, 159-167.
Illumina, "Patent Owner Illumina'S Preliminary Response to Petition", Oct. 17, 2018, 75 pgs.
Illumina, , "Plaintiff/Counterclaim Defendant Illumina, Inc.'s Amended Patent L.R. 3-3 Preliminary Invalidity Contentions for U.S. Pat. No. 8,682,592", Oct. 30, 2018, 22 pages.
Illumina, , "Plaintiff/Counterclaim-Defendant Illumina, Inc.'s Patent L.R. 3-3 Contentions for U.S. Patent Preliminary Invalidity Contentions for U.S. Pat. No. 8,682,592", Oct. 9, 2018, 81 pages.
Illumina Catalog, "Paired-End Sample Preparation Guide, Illumina Catalog# PE-930-1 001, Part# 1005063 Rev. E", 2011, 1-40.
Ishii, et al., "Optimization of Annealing Temperature to Reduce Bias Caused by a Primer Mismatch in Multitemplate PCR", Applied and Environmental Microbiology, Aug. 2001, p. 3753-3755.
Jabara, C. B. et al., "Accurate sampling and deep sequencing of the HIV-1 protease gene using a Primer ID", PNAS, vol. 108, No. 50, Dec. 13, 2011, 20166-20171.
Jahr, S. et al., "DNA Fragments in the Blood Plasma of Cancer Patients: Quantitations and Evidence for Their Origin from Apoptotic and Necrotic Cells", Cancer Research, vol. 61, Feb. 15, 2001, 1659-1665.
Jamal-Hanjani, M. et al., "Detection of ubiquitous and heterogeneous mutations in cell-free DNA from patients with early-stage non-small-cell lung cancer", Annals of Oncology, vol. 27, No. 5, Jan. 28, 2016, 862-867.
Jamal-Hanjani, M. et al., "Tracking Genomic Cancer Evolution for Precision Medicine: The Lung TRACERx Study", PLOS Biology, vol. 12, No. 7, Jul. 2014, 1-7.
Jamal-Hanjani, M. et al., "Tracking the Evolution of Non-Small-Cell Lung Cancer", The New England Journal of Medicine, vol. 376, No. 22, Jun. 1, 2017, 2109-2121.
Jarvie, T. , "Next generation sequencing technologies", Drug Discovery Today: Technologies, vol. 2, No. 3, 2005, 255-260.
Jenkins, S. et al., "High-throughput SNP genotyping", Comparative and Functional Genomics, vol. 3, Dec. 5, 2001, 57-66.
Johnson, D.S. et al., "Comprehensive Analysis of Karyotypic Mosaicism Between Trophectoderm and Inner Cell Mass", Molecular Human Reproduction, 16(12), 2010, 944-949.
Johnson D.S, et al., "Preclinical Validation of a Microarray Method for Full Molecular Karyotyping of Blastomeres in a 24-h Protocol", Human Reproduction, 25 (4), 2010, 1066-1075.
Kaplinski, Lauris et al., "MultiPLX: Automatic Grouping and Evaluation of PCR Primers", Bioinformatics, 21(8), 2005, 1701-1702.
Kazakov, V.I. et al., "Extracellular DNA in the Blood of Pregnant Women", Tsitologia, vol. 37, No. 3, 1995, 1-8.
Kijak, G. et al., "Discrepant Results in the Interpretation of HIV-1 Drug-Resistance Genotypic Data Among Widely Used Algorithms", HIV Medicine, 4, 2003, 72-78.
Kim, H. et al., "Whole-genome and multisector exome sequencing of primary and post-treatment glioblastoma reveals patterns of tumor evolution", Genome Research, vol. 25, No. 3, Feb. 3, 2015, 316-327.
Kinde, I. et al., "Detection and quantification of rare mutations with massively parallel sequencing", PNAS, vol. 108, No. 23, Jun. 7, 2011, 9530-9535.
Kinnings, S. L. et al., "Factors affecting levels of circulating cell-free fetal DNA in maternal plasma and their implications for noninvasive prenatal testing", Prenatal Diagnosis, vol. 35, 2015, 816-822.
Kirkizlar, E. et al., "Detection of Clonal and Subclonal Copy-Number Variants in Cell-Free DNA from Patients with Breast Cancer Using a Massively Multiplexed PCR Methodology", Translational Oncology, vol. 8, No. 5, Oct. 2015, pp. 407-416.
Kivioja, T. et al., "Counting absolute numbers of molecules using unique molecular identifiers", Nature Methods, Advance Online Publication, Nov. 20, 2011, 1-5.
Konfortov, Bernard A. et al., "An Efficient Method for Multi-Locus Molecular Haplotyping", Nucleic Acids Research, 35(1), e6, 2007, 8 pgs.
Krjutskov, K. et al., "Development of a single tube 640-plex genotyping method for detection of nucleic acid variations on microarrays", Nucleic Acids Research, vol. 36, No. 12, May 23, 2008, 7 pages.
Kuliev, Anver et al., "Thirteen Years' Experience on Preimplantation Diagnosis: Report of the Fifth International Symposium on Preimplantation Genetics", Reproductive BioMedicine Online, 8, 2, 2004, 229-235.
Kwok, P. Y. , "High-throughput genotyping assay approaches", Pharmacogenomics, vol. 1, No. 1, 2000, 1-5.
Lambert-Messerlian, G. et al., "Adjustment of Serum Markers in First Trimester Screening", Journal of Medical Screening, 16 (2), 2009, 102-103.
Lander, E. S. et al., "Initial sequencing and analysis of the human genome", Nature, vol. 409, Feb. 15, 2001, 860-921.
Lathi, Ruth B. et al., "Informatics Enhanced SNP Microarray Analysis of 30 Miscarriage Samples Compared to Routine Cytogenetics", PLoS ONE, 7(3), 2012, 5 pgs.
Leary, R. J. et al., "Development of Personalized Tumor Biomarkers Using Massively Parallel Sequencing", Science Translational Medicine, vol. 2, No. 20, Feb. 24, 2010, 1-8.
Leary, Rebecca J et al., "Detection of Chromosomal Alterations in the Circulation of Cancer Patients with Whole-Genome Sequencing", Science Translational Medicine, 4, 162, 2012, 12.

(56) References Cited

OTHER PUBLICATIONS

Levsky, J. M. et al., "Fluorescence in situ hybridization: past, present and future", Journal of Cell Science, vol. 116, No. 14, 2003, 2833-2838.
Li, B. , "Highly Multiplexed Amplicon Preparation for Targeted Re-Sequencing of Sample Limited Specimens Using the Ion AmpliSeq Technology and Semiconductor Sequencing", Proceedings of the Annual Meeting of the American Society of Human Genetics [retrieved on Oct. 30, 2012]. Retrieved from the Internet: <URL: http://www.ashg.org/2012meeting/abstracts/fulltext/f120121811. htm>, 2012, 1 pg.
Li, Y. et al., "Non-Invasive Prenatal Diagnosis Using Cell-Free Fetal DNA in Maternal Plasma from PGD Pregnancies", Reproductive BioMedicine Online, 19 (5), 2009, 714-720.
Li, Ying et al., "Size Separation of Circulatory DNA in Maternal Plasma Permits Ready Detection of Fetal DNA Polymorphisms", Clinical Chemistry, 50, 6, 2004, 1002-1011.
Liao, Gary J.W. et al., "Targeted Massively Parallel Sequencing of Maternal Plasma DNA Permits Efficient and Unbiased Detection of Fetal Alleles", Clinical Chemistry, 57 (1), 2011, 92-101.
Liao, J. et al., "An Alternative Linker-Mediated Polymerase Chain Reaction Method Using a Dideoxynucleotide to Reduce Amplification Background", Analytical Biochemistry 253, 137-139 (1997).
Liew, Michael et al., "Genotyping of Single-Nucleotide Polymorphisms", Clinical Chemistry, 50(7), 2004, 1156-1164.
Lindroos, Katatina et al., "Genotyping SNPs by Minisequencing Primer Extension Using Oligonucleotide Microarrays", Methods in Molecular Biology, 212, Single Nucleotide Polymorphisms: Methods and Protocols, P-K Kwok (ed.), Humana Press, Inc., Totowa, NJ, 2003, 149-165.
Lo, et al., "Digital PCR for the Molecular Detection of Fetal Chromosomal Aneuploidy", PNAS, vol. 104, No. 32, Aug. 7, 2007, 13116-13121.
Lo, et al., "Fetal Nucleic Acids in Maternal Blood: the Promises", Clin. Chem. Lab. Med., 50(6), 2012, 995-998.
Lo, et al., "Free Fetal DNA in Maternal Circulation", JAMA, 292(23), (Letters to the Editor), 2004, 2835-2836.
"Non-Invasive Prenatal Diagnosis by Massively parallel Sequencing of Maternal Plasma DNA", Open Biol 2: 120086, 2012, 1-5.
Lo, et al., "Prenatal Sex Determination by DNA Amplification from Maternal Peripheral Blood", The Lancet,2, 8676, 1989, 1363-1365.
Lo, et al., "Rapid Clearance of Fetal DNA from Maternal Plasma", Am. J. Hum. Genet., 64, 1999, 218-224.
Lo, et al., "Strategies for the Detection of Autosomal Fetal DNA Sequence from Maternal Peripheral Blood", Annals New York Academy of Sciences,731, 1994, 204-213.
Lo, et al., "Two-way cell traffic between mother and fetus: biologic and clinical implications", Blood, 88(11), Dec. 1, 1996, 4390-4395.
Lo, Y. , "Noninvasive prenatal detection of fetal chromosomal aneuploidies by maternal plasma nucleic acid analysis: a review of the current state of the art", BJOG An International Journal of Obstetrics and Gynaecology, vol. 116, 2009, 152-157.
Lo, Y.M. Dennis , "Fetal Nucleic Acids in Maternal Plasma: Toward the Development of Noninvasive Prenatal Diagnosis of Fetal Chromosomal Aneuploidies", Ann. N.Y. Acad. Sci., 1137, 2008, 140-143.
Lo, Y.M. Dennis et al., "Maternal Plasma DNA Sequencing Reveals the Genome-Wide Genetic and Mutational Profile of the Fetus", Science Translational Medicine,, 2 (61), 2010, 13.
Lo, Y.M. Dennis et al., "Plasma placental RNA allelic ratio permits noninvasive prenatal chromosomal aneuploidy detection", Nature Medicine, 13 (2), 2007, 218-223.
Lo, Y.M. Dennis et al., "Presence of Fetal DNA in Maternal Plasma and Serum", The Lancet, 350, 1997, 485-487.
Lo, Y.M. Dennis et al., "Quantitative Analysis of Fetal DNA in Maternal Plasma and Serum: Implications for Noninvasive Prenatal Diagnosis", Am. J. Hum. Genet., 62, 1998, 768-775.
Lo, Y-M.D et al., "Detection of Single-Copy Fetal DNA Sequence from Maternal Blood", The Lancet, 335, 1990, 1463-1464.
Lo, Y-M.D et al., "Prenatal Determination of Fetal Rhesus D Status by DNA Amplification of Peripheral Blood of Rhesus-Negative Mothers", Annals New York Academy of Sciences, 731, 1994, 229-236.
Lo, Y-M.D. et al., "Detection of Fetal RhD Sequence from Peripheral Blood of Sensitized RhD-Negative Pregnant Women", British Journal of Haematology, 87, 1994, 658-660.
Lo, Y-M.D. et al., "Prenatal Determination of Fetal RhD Status by Analysis of Peripheral Blood of Rhesus Negative Mothers", The Lancet, 341, 1993, 1147-1148.
Lu, I. et al., "Establishment of a system based on universal multiplex-PCR for screening genetically modified crops", Anal. Bioanal. Chem, vol. 396, Oct. 24, 2009, 2055-2064.
Lun, Fiona M. et al., "Noninvasive Prenatal Diagnosis of Monogenic Diseases by Digital Size Selection and Relative Mutation Dosage on DNA in Maternal Plasma", PNAS, 105(50), 2008, 19920-19925.
Ma, Xiaotu et al., "Rise and fall of subclones from diagnosis to relapse in pediatric B-acute lymphoblastic leukaemia", Nature Communications, vol. 6, Mar. 19, 2015, 1-12.
Mamon, H. et al., "Letters to the Editor: Preferential Amplification of Apoptotic DNA from Plasma: Potential for Enhancing Detection of Minor DNA Alterations in Circulating DNA", Clinical Chemistry, vol. 54, No. 9, 2008, 1582-1584.
Maniatis, T. et al., "In: Molecular Cloning: A Laboratory Manual", Cold Spring Harbor Laboratory, New York, Thirteenth Printing, 1986, 458-459.
Mansfield, Elaine S , "Diagnosis of Down Syndrome and Other Aneuploidies Using Quantitative Polymerase Chain Reaction and Small Tandem Repeat Polymorphisms", Human Molecular Genetics, 2, 1, 1993, 43-50.
Margulies, M. et al., "Genome sequencing in microfabricated high-density picolitre reactors", Nature, vol. 437, Sep. 15, 2005, 376-380.
Margulies, M. et al., "Genome sequencing in microfabricated high-density picolitre reactors plus Supplemental Methods", Nature, vol. 437, Sep. 15, 2005, 40 pgs.
Markoulatos, P. et al., "Multiplex Polymerase Chain Reaction: A Practical Approach", Journal of Clinical Laboratory Analysis, vol. 16, 2002, 47-51.
May, Robert M. , "How Many Species Are There on Earth?", Science, 241, Sep. 16, 1988, 1441-1449.
McBride, D. et al., "Use of Cancer-Specific Genomic Rearrangements to Quantify Disease Burden in Plasma from Patients with Solid Tumors", Genes, Chromosomes & Cancer, vol. 49, Aug. 19, 2010, 1062-1069.
McCloskey, M. L. et al., "Encoding PCR Products with Batch-stamps and Barcodes", Biochem Genet., vol. 45, Oct. 23, 2007, 761-767.
McCray, Alexa T. et al., "Aggregating UMLS Semantic Types for Reducing Conceptual Complexity", MEDINFO 2001: Proceedings of the 10th World Congress on Medical Informatics (Studies in Health Technology and Informatics, 84, V. Patel et al. (eds.), IOS Press Amsterdam, 2001, 216-220.
Mennuti, M. et al., "Is It Time to Sound an Alarm About False-Positive Cell-Free DNA Testing for Fetal Aneuploidy?", American Journal of Obstetrics, 2013, 5 pgs.
Merriam-Webster, , "Medical Definition of Stimulant", http://www.merriam-webster.com/medical/stimulant, Mar. 14, 2016, 7 pages.
Mersy, et al., "Noninvasive Detection of Fetal Trisomy 21: Systematic Review and Report of Quality and Outcomes of Diagnostic Accuracy Studies Performed Between 1997 and 2012", Human Reproduction Update, 19(4), 2013, 318-329.
Miller, Robert , "Hyperglycemia-Induced Changes in Hepatic Membrane Fatty Acid Composition Correlate with Increased Caspase-3 Activities and Reduced Chick Embryo Viability", Comparative Biochemistry and Physiology, Part B, 141, 2005, 323-330.
Miller, Robert R. , "Homocysteine-Induced Changes in Brain Membrane Composition Correlate with Increased Brain Caspase-3 Activities and Reduced Chick Embryo Viability", Comparative Biochemistry and Physiology Part B, 136, 2003, 521-532.
Miner, B. E. et al., "Molecular barcodes detect redundancy and contamination in hairpin-bisulfite PCR", Nucleic Acids Research, vol. 32, No. 17, Sep. 30, 2004, 1-4.

(56) References Cited

OTHER PUBLICATIONS

Minkoff, E. et al., "Stem Cells, Cell Division, and Cancer", Biology Today Third Edition, Chapter 12, 2004, 10 pages.
Morand, et al., "Hesperidin contributes to the vascular protective effects of orange juice: a randomized crossover study in healthy volunteers", Am J Clin Nutr. Jan. 2011;93(1):73-80. Epub Nov. 10, 2010.
Munne, S. et al., "Chromosome Abnormalities in Human Embryos", Textbook of Assisted Reproductive Techniques, 2004, pp. 355-377.
Murtaza, M. et al., "Non-Invasive Analysis of Acquired Resistance to Cancer Therapy by Sequencing of Plasma DNA", Nature (doi:10.1038/nature12065), 2013, 6 pgs.
Muse, Spencer V. , "Examining rates and patterns of nucleotide substitution in plants", Plant Molecular Biology 42: 25-43, 2000.
Myers, Chad L. et al., "Accurate Detection of Aneuploidies in Array CGH and Gene Expression Microarray Data", Bioinformatics, 20(18), 2004, 3533-3543.
Nannya, Yasuhito et al., "A Robust Algorithm for Copy Number Detection Using High-density Oligonucleotide Single Nucleotide Polymorphism Genotyping Arrays", Cancer Res., 65, 14, 2005, 6071-6079.
Narayan, A. et al., "Ultrasensitive measurement of hotspot mutations in tumor DNA in blood using error-suppressed multiplexed deep sequencing", Cancer Research, vol. 72, No. 14, Jul. 15, 2012, 3492-3498.
Natera, Inc., , "Defendant Natera, Inc.'s Invalidity Contentions Under Patent L.R. 3-3; Document Production Accompanying Invalidity Contentions Under Patent L.R. 3-4", Aug. 20, 2018, 17 pages.
Natera, Inc. "Exhibit 8 Ehrich Invalidity Chart", Aug. 20, 2018, 16 pages.
Natera, Inc. "Petitioner Reply Per Board Order of Nov. 2, 2018 (Paper No. 10)", Nov. 9, 2018, 8 pgs.
Nicolaides, K. et al., "Noninvasive Prenatal Testing for Fetal Trisomies in a Routinely Screened First-Trimester Population", American Journal of Obstetrics (article in press), 207, 2012, 1.e1-1.e6.
Nicolaides, K.H et al., "Validation of Targeted Sequencing of Single-Nucleotide Polymorphisms for Non-Invasive Prenatal Detection of Aneuploidy of Chromosomes 13, 18, 21, X, and Y", Prenatal Diagnosis, 33, 2013, 575-579.
Nicolaides, Kypros H. et al., "Prenatal Detection of Fetal Triploidy from Cell-Free DNA Testing in Maternal Blood", Fetal Diagnosis and Therapy, 2013, 1-6.
Nygren, et al., "Quantification of Fetal DNA by Use of Methylation-Based DNA Discrimination", Clinical Chemistry 56:10 1627-1635 (2010).
Ogino, S. et al., "Bayesian Analysis and Risk Assessment in Genetic Counseling and Testing", Journal of Molecular Diagnostics, 6 (1), 2004, 9 pgs.
Ohsawa, M. et al., "Prenatal Diagnosis of Two Pedigrees of Fukuyama Type Congenital Muscular Dystrophy by Polymorphism Analysis", The Health and Welfare Ministry, 1994, 5 pgs.
O'Malley, R. et al., "An adapter ligation-mediated PCR method for high-throughput mapping of T-DNA inserts in the *Arabidopsis* genome", Nat. Protoc., 2, 2007, 2910-2917.
Orozco A.F., et al., "Placental Release of Distinct DNA-Associated Micro-Particles into Maternal Circulation: Reflective of Gestation Time and Preeclampsia", Placenta,30, 2009, 891-897.
Ozawa, Makiko et al., "Two Families with Fukuyama Congenital Muscular Dystrophy that Underwent in Utero Diagnosis Based on Polymorphism Analysis", Clinical Muscular Dystrophy: Research in Immunology and Genetic Counseling—FY 1994 Research Report, (including text in Japanese), 1994, 8.
Paez, Guillermo J. et al., "Genome coverage and sequence fidelity of Φ29 polymerase-based multiple strand displacement whole genome amplification", Nucleic Acids Research, 32(9), 2004, 1-11.
Page, S. L. et al., "Chromosome Choreography: The Meiotic Ballet", Science, 301, 2003, 785-789.
Palomaki, G. E. et al., "DNA sequencing of maternal plasma to detect Down syndrome: An international clinical validation study", Genetics in Medicine, vol. 13, No. 1, Nov. 2011, 913-920.
Palomaki, Glenn et al., "DNA Sequencing of Maternal Plasma Reliably Identifies Trisomy 18 and Trisomy 13 as Well as Down Syndrome: an International Collaborative Study", Genetics in Medicine, 2012, 10.
Palomaki, Glenn E. et al., "DNA Sequencing of Maternal Plasma to Detect Down Syndrome: An International Clinical Validation Study", Genetics in Medicine (pre-print version), 13, 2011, 8 pgs.
Papageorgiou, Elisavet A. et al., "Fetal-Specific DNA Methylation Ratio Permits Noninvasive Prenatal Diagnosis of Trisomy 21", Nature Medicine (advance online publication),17, 2011, 5 pgs.
Pathak, A. et al., "Circulating Cell-Free DNA in Plasma/Serum of Lung Cancer Patients as a Potential Screening and Prognostic Tool", Clinical Chemistry, 52, 2006, 1833-1842.
PCT/US2006/045281, , "International Preliminary Report on Patentability", dated May 27, 2008, 1 pg.
PCT/US2006/045281, , "International Search Report and Written Opinion", dated Sep. 28, 2007, 7 pgs.
PCT/US2008/003547, , "International Search Report", dated Apr. 15, 2009, 5 pgs.
PCT/US2009/034506, , "International Search Report", dated Jul. 8, 2009, 2 pgs.
PCT/US2009/045335, , "International Search Report", dated Jul. 27, 2009, 1 pg.
PCT/US2009/052730, , "International Search Report", dated Sep. 28, 2009, 1 pg.
PCT/US2010/050824, , "International Search Report", dated Nov. 15, 2010, 2 pgs.
PCT/US2011/037018, , "International Search Report", dated Sep. 27, 2011, 2 pgs.
PCT/US2011/061506, , "International Search Report", dated Mar. 16, 2012, 1 pgs.
PCT/US2011/066938, , "International Search Report", dated Jun. 20, 2012, 1 pg.
PCT/US2012066339, , "International Search Report", dated Mar. 5, 2013, 1 pg.
PCT/US2013/028378, , "International Search Report and Written Opinion", dated May 28, 2013, 11 pgs.
PCT/US2013/57924, , "International Search Report and Written Opinion", dated Feb. 18, 2014, 8 pgs.
PCT/US2014/051926, , "International Search Report and Written Opinion", dated Dec. 9, 2014, 3 pgs.
Pearson, K. , "On the criterion that a given system of deviations from the probable in the case of a correlated system of variables is such that it can be reasonably supposed to have arisen from random sampling", Philosophical Magazine Series 5, vol. 50, Issue 302, 1900, 157-175.
Pena, Sergio D.J et al., "Paternity Testing in the DNA Era", Trends in Genetics, 10, 6, 1994, 204-209.
Pergament, E. et al., "Single-Nucleotide Polymorphism-Based Noninvasive Prenatal Screening in a High-Risk and Low-Risk Cohort", Obstetrics & Gynecology, vol. 124, No. 2, Part 1, Aug. 2014, 210-218 + Appendices.
Perkel, Jeffrey M. , "Overcoming the Challenges of Multiplex PCR", Biocompare Editorial Article, Null, 2012, 1-5.
Perry, George H. et al., "The Fine-Scale and Complex Architecture of Human Copy-Number Variation", The American Journal of Human Genetics,82, 2008, 685-695.
Pertl, B. et al., "Detection of Male and Female Fetal DNA in Maternal Plasma by Multiplex Fluorescent Polymerase Chain Reaction Amplification of Short Tandem Repeats", Hum. Genet., 106, 2000, 45-49.
Peters, David P. et al., "Noninvasive Prenatal Diagnosis of a Fetal Microdeletion Syndrome", New England Journal of Medicine, 365(19), 2011, 1847-1848.
Pfaffl, Michael W. , "Relative Expression Software Tool (REST©) for Group-Wise Comparison and Statistical Analysis of Relative Expression Results in real-Time PCR", Nucleic Acids Research, 30(9), 2002, 10 pgs.

(56) References Cited

OTHER PUBLICATIONS

Phillips, C. et al., "Resolving Relationship Tests that Show Ambiguous STR Results Using Autosomal SNPs as Supplementary Markers", Forensic Science International: Genetics 2, 2008, 198-204.
Podder, Mohua et al., "Robust SN P genotyping by multiplex PCR and arrayed primer", BMC Medical Genomics,1(5), 2008, 1-15.
Popova, T. et al., "Genome Alteration Print (GAP): a tool to visualize and mine complex cancer genomic profiles obtained by SNP arrays", Genome Biology, vol. 10, R128, Nov. 11, 2009, 1-14.
Porreca, Gregory J et al., "Multiplex Amplification of Large Sets of Human Exons", Nature Methods, 4, (advance online publication), 2007, 6.
Price, T.S. et al., ""SW-Array: a dynamic programming solution for the identification of copy-number changes in genomic DNA using array comparative genome hybridization data",", Nucleic Acids Research, vol. 33, No. 11, Jun. 16, 2005, 3455-3464.
Primdahl, H. et al., "Allelic Imbalances in Human Bladder Cancer: Genome-Wide Detection With High-Density Single-Nucleotide Polymorphism Arrays", Journal of the National Cancer Institute, vol. 94, No. 3, Feb. 6, 2002, 216-223.
Quinn, G. P. et al., "Experimental Design and Data Analysis for Biologists", Graphical Exploration of Data, 2002, 64-67.
Rabinowitz, et al., "Accurate Prediction of HIV-1 Drug Response from the Reverse Transcriptase and Protease Amino Acid Sequences Using Sparse Models Created by Convex Optimization", Bioinformatics, 22, 5, 2006, 541-549.
Rabinowitz, Matthew et al., "Origins and rates of aneuploidy inhuman blastomeres", Fertility and Sterility, vol. 97, No. 2, Feb. 2012, 395-401.
Rabinowitz, Matthew. et al., "Non-Invasive Prenatal Aneuploidy Testing of Chromosomes 13, 18, 21, X, and Y Using Targeted Sequencing of Polymorphic Loci", The American Society of Human Genetics, meeting poster, 2012, 1 pg.
Rachlin, J. et al., "Computational tradeoffs in multiplex PCR assay design for SNP genotyping", BMC Genomics, vol. 6, No. 102, Jul. 25, 2005, 11 pages.
Ragoussis, J. , "Genotyping Technologies for Genetic Research", Annual Review of Genomics and Human Genetics, vol. 10 (1), Sep. 1, 2009, 117-133.
Rahmann, Sven et al., "Mean and variance of the Gibbs free energy of oligonucleotides in the nearest neighbor model under varying conditions", Bioinformatics, 20(17), 2004, 2928-2933.
Rava, Richard P. et al., "Circulating Fetal Cell-Free DNA Fraction Differ in Autosomal Aneuploidies and Monosomy X", Clinical Chemistry, 60(1), (papers in press), 2013, 8 pgs.
Rechitsky, Svetlana et al., "Preimplantation Genetic Diagnosis with HLA Matching", Reproductive Bio Medicine Online, 9, 2, 2004, 210-221.
Renwick, P. et al., "Proof of Principle and First Cases Using Preimplantation Genetic Haplotyping—A Paradigm Shift for Embryo Diagnosis", Reproductive BioMedicine Online, 13 (1), 2006, 110-119.
Ricciotti, Hope , "Eating by Trimester", Online]. Retrieved from Internet:<http://www.youandyourfamily.com/article.php?story=Eating+by+Trimester>, 2014, 3.
Riley, D. E. , "DNA Testing: An Introduction for Non-Scientists an Illustrated Explanation", Scientific Testimony: An Online Journal, http://www.scientific.org/tutorials/articles/riley/riley.html, Apr. 6, 2005, 22 pages.
Rogaeva, E. et al., "The Solved and Unsolved Mysteries of the Genetics of Early-Onset Alzheimer's Disease", NeuroMolecular Medicine, vol. 2, 2002, 1-10.
Roper, Stephen M. et al., "Forensic Aspects of DNA-Based Human Identity Testing", Journal of Forensic Nursing, 4, 2008, 150-156.
Roux, K. , "Optimization and Troubleshooting in PCR", PCR Methods Appl. 4, 1995, 185-194.
Rozen, Steve et al., "Primer3 on the WWW for General Users and for Biologis Programmers", Methods in Molecular Biology, 132: Bioinformatics Methods and Protocols, 1999, 365-386.
Russell, L. M. , "X Chromosome Loss and Ageing", Cytogenetic and Genome Res., 116, 2007, 181-185.
Ryan, A. et al., "Informatics-Based, Highly Accurate, Noninvasive Prenatal Paternity Testing", Genetics in Medicine (advance online publication), 2012, 5 pgs.
Rychlik, et al., "Optimization of the annealing temperature for DNA amplification in vitro", Nucleic Acids Research, 18(21), 1990, 6409-6412.
Sahota, A. , "Evaluation of Seven PCR-Based Assays for the Analysis of Microchimerism", Clinical Biochemistry, vol. 31, No. 8., 1998, 641-645.
Samango-Sprouse, C. et al., "SNP-Based Non-Invasive Prenatal Testing Detects Sex Chromosome Aneuploidies with High Accuracy", Prenatal Diagnosis, 33, 2013, 1-7.
Sander, Chris , "Genetic Medicine and the Future of Health Care", Science, 287(5460), 2000, 1977-1978.
Santalucia, J. et al., "The Thermodynamics of DNA Structural Motifs", Annu. Rev. Biophys. Biomol. Struct., 33, 2004, 415-440.
Santalucia, John J.R et al., "Improved Nearest-Neighbor Parameters for Predicting DNA Duplex Stability", Biochemistry, 35, 1996, 3555-3562.
Sasabe, Yutaka , "Genetic Diagnosis of Gametes and Embryos Resulting from ART", Japanese Journal of Fertility and Sterility, vol. 46, No. 1, 2001, 43-46.
Schmitt, M. W. et al., "Detection of ultra-rare mutations by next-generation sequencing", PNAS, vol. 109, No. 36, Sep. 4, 2012, 14508-14513.
Schoumans, J et al., "Detection of chromosomal imbalances in children with idiopathic mental retardation by array based comparative genomic hybridisation (array-CGH)", JMed Genet, 42, 2005, 699-705.
Sebat, Jonathan et al., "Strong Association of De Novo Copy Number Mutations with Autism", Science, 316, 2007, 445-449.
Sehnert, A. et al., "Optimal Detection of Fetal Chromosomal Abnormalities by Massively Parallel DNA Sequencing of Cell-Free Fetal DNA from Maternal Blood", Clinical Chemistry (papers in press), 57 (7), 2011, 8 pgs.
Sermon, Karen et al., "Preimplantation genetic diagnosis", The Lancet, Lancet Limited. 363(9421), 2000, 1633-1641.
Servin, B et al., "MOM: A Program to Compute Fully Informative Genotype Frequencies in Complex Breeding Schemes", Journal of Heredity, vol. 93, No. 3, Jan. 1, 2002 (Jan. 1, 2002), pp. 227-228.
Shaw-Smith, et al., "Microarray Based Comparative Genomic Hybridisation (array-CGH) Detects Submicroscopic Chromosomal Deletions and Duplications in Patients with Learning Disability/Mental Retardation and Dysmorphic Features", J. Med. Genet., 41, 2004, 241-248.
Shen, et al., "High-quality DNA sequence capture of 524 disease candidate genes", High-quality DNA sequence capture of 524 disease candidate genes, Proceedings of the National Academy of Sciences, vol. 108, No. 16, Apr. 5, 2011 (Apr. 5, 2011), pp. 6549-6554.
Shen, R. et al., "High-throughput SNP genotyping on universal bead arrays", Mutation Research, vol. 573, Feb. 11, 2005, 70-82.
Shen, Zhiyong , "MPprimer: a program for reliable multiplex PCR primer design", BMC Bioinformatics 2010, 11:143, 1-7.
Sherlock, J et al., "Assessment of Diagnostic Quantitative Fluorescent Multiplex Polymerase Chain Reaction Assays Performed on Single Cells", Annals of Human Genetics,62, 1, 1998, 9-23.
Shiroguchi, K. et al., "Digital RNA sequencing minimizes sequence-dependent bias and amplification noise with optimized single-molecule barcodes", PNAS, vol. 109, No. 4, Jan. 24, 2012, 1347-1352.
Simpson, J. et al., "Fetal Cells in Maternal Blood: Overview and Historical Perspective", Annals New York Academy of Sciences, 731, 1994, 1-8.
Sint, Daniela et al., "Advances in Multiplex PCR: Balancing Primer Efficiencies and Improving Detection Success", Methods in Ecology and Evolution, 3, 2012, 898-905.
Slater, Howard et al., "High-Resolution Identification of Chromosomal Abnormalities Using Oligonucleotide Arrays Containing 116,204 SNPs", Am. J. Hum. Genet., 77, 5, 2005, 709-726.

(56) References Cited

OTHER PUBLICATIONS

Snijders, Antoine et al., "Assembly of Microarrays for Genome-Wide Measurement of DNA Copy Number", Nature Genetic, 29, 2001, 263-264.
Sparks, A. et al., "Non-Invasive Prenatal Detection and Selective Analysis of Cell-Free DNA Obtained from Maternal Blood: Evaluation for Trisomy 21 and Trisomy 18", American Journal of Obstetrics & Gynecology 206, 2012, 319.e1-319.e9.
Sparks, Andrew B. et al., "Selective Analysis of Cell-Free DNA in Maternal Blood for Evaluation of Fetal Trisomy", Prenatal Diagnosis, 32, 2012, 1-7.
Spiro, Alexander et al., "A Bead-Based Method for Multiplexed Identification and Quantitation of DNA Sequences Using Flow Cytometry", Applied and Environmental Microbiology, 66, 10, 2000, 4258-4265.
Spits, C et al., "Optimization and Evaluation of Single-Cell Whole Genome Multiple Displacement Amplification", Human Mutation, 27(5), 496-503, 2006.
Srinivasan, et al., "Noninvasive Detection of Fetal Subchromosome Abnormalities via Deep Sequencing of Maternal Plasma", The American Journal of Human Genetics 92, 167-176, Feb. 7, 2013.
Stephens, Mathews. et al., "A Comparison of Bayesian Methods for Haplotype Reconstruction from Population Genotype Data", Am. J. Hum. Genet.,73, 2003, 1162-1169.
Stevens, Robert et al., "Ontology-Based Knowledge Representation for Bioinformatics", Briefings in Bioinformatics, 1, 4, 2000, 398-414.
Steyerberg, E.W et al., "Application of Shrinkage Techniques in Logistic Regression Analysis: A Case Study", Statistica Neerlandica, 55(1), 2001, 76-88.
Strom, C. et al., "Three births after preimplantation genetic diagnosis for cystic fibrosis with sequential first and second polar body analysis", American Journal of Obstetrics and Gynecology, 178 (6), 1998, 1298-1306.
Strom, Charles M. et al., "Neonatal Outcome of Preimplantation Genetic Diagnosis by Polar Body Removal: The First 109 Infants", Pediatrics, 106( 4), 2000, 650-653.
Stroun, Maurice et al., "Prehistory of the Notion of Circulating Nucleic Acids in Plasma/Serum (CNAPS): Birth of a Hypothesis", Ann. N.Y. Acad. Sci., 1075, 2006, 10-20.
Su, S.Y. et al., ""Inferring combined CNV/SNP haplotypes from genotype data"", Bioinformatics, vol. 26, No. 11,1, Jun. 1, 2010, 1437-1445.
Sun, Guihua et al., "SNPs in human miRNA genes affect biogenesis and function", RNA, 15(9), 2009, 1640-1651.
Sweet-Kind Singer, J. A. et al., "Log-penalized linear regression", IEEE International Symposium on Information Theory, 2003. Proceedings, 2003, 286.
Taliun, D. et al., "Efficient haplotype block recognition of very long and dense genetic sequences", BMC Bioinformatics, vol. 15 (10), 2014, 1-18.
Tamura, et al., "Sibling Incest and formulation of paternity probability: case report", Legal Medicine, 2000, vol. 2, p. 189-196.
Tang, et al., , Multiplex fluorescent PCR for noninvasive prenatal detection of fetal-derived paternally inherited diseases using circulatory fetal DNA in maternal plasma, Eur J Obstet Gynecol Reprod Biol, 2009, v.144, No. 1, p. 35-39.
Tang, N. et al., "Detection of Fetal-Derived Paternally Inherited X-Chromosome Polymorphisms in Maternal Plasma", Clinical Chemistry, 45 (11), 1999, 2033-2035.
Tebbutt, S. J. et al., "Microarray genotyping resource to determine population stratification in genetic association studies of complex disease", BioTechniques, vol. 37, Dec. 2004, 977-985.
Ten Bosch, J. , "Keeping Up With the Next Generation Massively Parallel Sequencing in Clinical Diagnostics", Journal of Molecular Diagnostics, vol. 10, No. 6, 2008, 484-492.
Tewhey, R. et al., "The importance of phase information for human genomics", Nature Reviews Genetics, vol. 12, No. 3, Mar. 1, 2011, 215-223.

Thermofisher Scientific, , "Ion AmpliSeq Cancer Hotspot Panel v2", Retrieved from the Internet: https://tools.thermofisher.com/content/sfs/brochures/Ion-AmpliSeq-Cancer-Hotspot-Panel-Flyer.pdf, 2015, 2 pages.
Thomas, M.R et al., "The Time of Appearance and Disappearance of Fetal DNA from the Maternal Circulation", Prenatal Diagnosis, 15, 1995, 641-646.
Tong, Yu et al., "Noninvasive Prenatal Detection of Fetal Trisomy 18 by Epigenetic Allelic Ratio Analysis in Maternal Plasma: Theoretical and Empirical Considerations", Clinical Chemistry, 52(12), 2006, 2194-2202.
Tong, Yu K. et al., "Noninvasive Prenatal Detection of Trisomy 21 by Epigenetic-Genetic Chromosome-Dosage Approach", Clinical Chemistry, 56(1), 2010, 90-98.
Troyanskaya, Olga G. et al., "A Bayesian Framework for Combining Heterogeneous Data Sources for Gene Function Prediction (in *Saccharomyces cerevisiae*)", PNAS, 100(14), 2003, 8348-8353.
Tsui, Nancy B.Y et al., "Non-Invasive Prenatal Detection of Fetal Trisomy 18 by RNA-SNP Allelic Ratio Analysis Using Maternal Plasma SERPINB2 mRNA: A Feasibility Study", Prenatal Diagnosis, 29, 2009, 1031-1037.
Tu, J. et al., "Pair-barcode high-throughput sequencing for large-scale multiplexed sample analysis", BMC Genomics, vol. 13, No. 43, Jan. 25, 2012, 1-9.
Turner, E. et al., "Massively Parallel Exon Capture and Library-Free Resequencing Across 16 Genomes", Nature Methods, 6 (5), 2009, 315-316.
Vallone, Peter , "AutoDimer: a Screening Tool for Primer-Dimer and Hairpin Structures", Bio Techniques, 37, 2004, 226-231.
Varley, Katherine Elena et al., "Nested Patch PCR Enables Highly Multiplexed Mutation Discovery in Candidate Genes", Genome Res., 18(11), 2008, 1844-1850.
Verlinsky, Y. et al., "Over a Decade of Experience with Preimplantation Genetic Diagnosis", Fertility and Sterility, 82 (2), 2004, 302-303.
Wagner, Jasenka et al., "Non-Invasive Prenatal Paternity Testing from Maternal Blood", Int. J. Legal Med., 123, 2009, 75-79.
Wang, Eric et al., "Gestational Age and Maternal Weight Effects on Fetal Cell-Free DNA in Maternal Plasma", Prenatal Diagnosis, 33, 2013, 662-666.
Wang, Hui-Yun et al., "A genotyping system capable of simultaneously analyzing >1000 single nucleotide polymorphisms in a haploid genome", Genome Res., 15, 2005, 276-283.
Wang, T.L. et al., "Digital karyotyping", PNAS, vol. 99, No. 25, Dec. 10, 2002, 16156-16161.
Wang, Yuker et al., "Allele quantification using molecular inversion probes (MIP)", Nucleic Acids Research, vol. 33, No. 21, Nov. 28, 2005, 14 pgs.
Wapner, R. et al., "Chromosomal Microarray Versus Karyotyping for Prenatal Diagnosis", The New England Journal of Medicine, 367 (23), 2012, 2175-2184.
Wapner, R. et al., "First-Trimester Screening for Trisomies 21 and 18", The New England Journal of Medicine, vol. 349, No. 15, Oct. 9, 2003, 1405-1413.
Watkins, N. et al., "Thermodynamic contributions of single internal rA •dA, rC • dC, rG • dG and rU • dT mismatches in RNA/DNA duplexes", Nucleic Acids Research, 9 (5),, 2010, 1894-1902.
Wells, D , "Microarray for Analysis and Diagnosis of Human Embryos", 12th International Congress on Prenatal Diagnosis and Therapy, Budapest, Hungary, 2004, 9-17.
Wells, Dagan , "Advances in Preimplantation Genetic Diagnosis", European Journal of Obstetrics and Gynecology and Reproductive Biology, 115S, 2004, S97-S101.
Wells, Dagan , "Detailed Chromosomal and Molecular Genetic Analysis of Single Cells by Whole Genome Amplification and Comparative Genomic Hybridisation", Nucleic Acids Research, 27, 4, 1999, 1214-1218.
Wen, Daxing et al., "Universal Multiples PCR: A Novel Method of Simultaneous Amplification of Multiple DNA Fragments", Plant Methods, 8(32), NULL, 2012, 1-9.
Wikipedia, , "Maximum a posteriori estimation", https://en.wikipedia.org/w/index.php?title=Maximum_a_posteriori_estimation&oldid=26878808, [retrieved on Aug. 1, 2017], Oct. 30, 2005, 2 pages.

(56) References Cited

OTHER PUBLICATIONS

Wilton, et al., "Birth of a Healthy Infant After Preimplantation Confirmation of Euploidy by Comparative Genomic Hybridization", N. Engl. J. Med., 345(21), 2001, 1537-1541.
Wilton, L. , "Preimplantation Genetic Diagnosis and Chromosome Analysis of Blastomeres Using Comparative Genomic Hybridization", Human Reproduction Update, 11 (1), 2005, 33-41.
Wright, C. et al., "The use of cell-free fetal nucleic acids in maternal blood for non-invasive prenatal diagnosis", Human Reproduction Update, vol. 15, No. 1, 2009, 139-151.
Wright, C. F. et al., "Cell-free fetal DNA and RNA in maternal blood: implications for safer antenatal testing", BMJ, vol. 39, Jul. 18, 2009, 161-165.
Wu, Y. Y. et al., "Rapid and/or high-throughput genotyping for human red blood cell, platelet and leukocyte antigens, and forensic applications", Clinica Chimica Acta, vol. 363, 2006, 165-176.
Xia, Tianbing et al., "Thermodynamic Parameters for an Expanded Nearest-Neighbor Model for Formation of RNA Duplexes with Watson-Crick Base Pairs", Biochemistry, 37, 1998, 14719-14735.
Xu, N. et al., "A Mutation in the Fibroblast Growth Factor Receptor 1 Gene Causes Fully Penetrant Normosmic Isolated Hypogonadotropic Hypogonadism", The Journal of Clinical Endocrinology & Metabolism, vol. 92, No. 3, 2007, 1155-1158.
Xu, S. et al., "Circulating tumor DNA identified by targeted sequencing in advanced-stage non-small cell lung cancer patients", Cancer Letters, vol. 370, 2016, 324-331.
Yeh, Iwei et al., "Knowledge Acquisition, Consistency Checking and Concurrency Control for Gene Ontology (GO)", Bioinformatics, 19, 2, 2003, 241-248.
You, Frank M. et al., "BatchPrimer3: A high throughput web application for PCR and sequencing primer design", BMC Bioinformatics, Biomed Central, London, GB, vol. 9, No. 1, May 29, 2008 (May 29, 2008), p. 253.
Yuan, X. et al., "Probability Theory-based SNP Association Study Method for Identifying Susceptibility Loci and Genetic Disease Models in Human Case-Control Data", IEEE Trans Nanobioscience, vol. 9, No. 4, Dec. 2010, 232-241.
Zhang, Rui et al., "Quantifying RNA allelic ratios by microfluidic multiplex PCR and sequencing", Nature Methods, 11(1), 2014, 51-56.
Zhao, Xiaojun. et al., "An Integrated View of Copy Number and Allelic Alterations in the Cancer Genome Using Single Nucleotide Polymorphism Arrays", Cancer Research,64, 2004, 3060-3071.
Zhong, X. et al., "Risk free simultaneous prenatal identification of fetal Rhesus D status and sex by multiplex real-time PCR using cell free fetal DNA in maternal plasma", Swiss Medical Weekly, vol. 131, Mar. 2001, 70-74.
Zhou, W. et al., "Counting Alleles Reveals a Connection Between Chromosome 18q Loss and Vascular Invasion", Nature Biotechnology, 19, 2001, 78-81.
Zimmermann, et al., "Noninvasive Prenatal Aneuploidy Testing of Chromosomes 13, 18, 21 X, and Y, Using targeted Sequencing of Polymorphic Loci", Prenatal Diagnosis, 32, 2012, 1-9.
Zimmermann, B. , "Noninvasive prenatal aneuploidy testing of chromosomes 13, 18, 21, X and Y, using targeted sequencing of polymorphic loci, Supplemental Information", Prenatal Diagnosis, vol. 32, 2012, 7 pages.
Allan, J. et al., "Micrococcal Nuclease Does Not Substantially Bias Nucleosome Mapping", Journal of Molecular Biology, vol. 417, Jan. 30, 2012, 152-164.
Beck, J. et al., "Digital Droplet PCR for Rapid Quantification of Donor DNA in the Circulation of Transplant Recipients as a Potential Universal Biomarker of Graft Injury", Clinical Chemistry, vol. 59, No. 12, 2013, 1732-1741.
Cheung, V. G. et al., "Whole genome amplification using a degenerate oligonucleotide primer allows hundreds of genotypes to be performed on less than one nanogram of genomic DNA", Proceedings of the National Academy of Sciences, USA, vol. 93, Dec. 1996, 14676-14679.
Diehl, F. et al., "Circulating mutant DNA to assess tumor dynamics", Nature Medicine, vol. 14, No. 9, Jul. 31, 2008, 985-990.
Gielis, E. M. et al., "Plasma donor-derived cell-free DNA kinetics after kidney transplantation using a single tube multiplex PCR assay", PLOS One, vol. 13, No. 12, e0208207, Dec. 6, 2018, 16 pgs.
Grskovic, M. et al., "Validation of a Clinical-Grade Assay to Measure Donor-Derived Cell-Free DNA in Solid Organ Transplant Recipients", The Journal of Molecular Diagnostics, vol. 18, No. 6 + Supplemental Appendix 51, Nov. 2016, 890-902.
Imielinski, M. et al., "Mapping the Hallmarks of Lung Adenocarcinoma with Massively Parallel Sequencing", Cell, vol. 150, Sep. 14, 2012, 1107-1120.
Life Technologies, , "Ion AmpliSeq™ Designer provides full flexibility to sequence genes of your choice", Retrieved from the Internet<URL: http://tools.lifetechnologies.com/content/sfs/brochures/IonAmpliSeq_CustomPanels_AppNote_CO1, 2012, 4 pages.
Lindberg, J. et al., "Exome Sequencing of Prostate Cancer Supports the Hypothesis of Independent Tumour Origins", European Urology, vol. 63, 2013, 347-353.
Munne, S. et al., "Chromosome abnormalities in human embryos", European Society of Human Reproduction and Embryology: Human Reproduction Update, vol. 4, No. 6, 1998, 842-855.
NCBI, , "dbSNP record for rs1294331", Retrieved from the Internet: <URL: www.ncbi.nlm.nih.gov/snp/?term=rs 1294331 >, 2019, 2 pgs.
NCBI, , "dbSNP record for rs1872575", Retrieved from the Internet: <URL: www.ncbi.nlm.nih.gov/snp/?term=rs1872575, 2019, 2 pgs.
NCBI, , "dbSNP record for rs2362450", Retrieved from the Internet: <URL: www.ncbi.nlm.nih.gov/snp/?term=rs2362450>, 2019, 1 pg.
NCBI, , "dbSNP record for rs2384571", Retrieved from the Internet: <URL: www.ncbi.nlm.nih.gov/snp/?term=rs2384571>, 2019, 2 pgs.
NCBI, , "dbSNP record for rs2498982", Retrieved from the Internet: <URL: www.ncbi.nlm.nih.gov/snp/?term=rs2498982>, 2019, 3 pgs.
NCBI, , "dbSNP record for rs3731877", Retrieved from the Internet: <URL: www.ncbi.nlm.nih.gov/snp/?term=rs3731877>, 2019, 2 pgs.
Schwarzenbach, H. et al., "Cell-free nucleic acids as biomarkers in cancer patients", Nature Reviews: Cancer, vol. 11, Jun. 2011, 426-437.
Shi, H. et al., "Melanoma whole-exome sequencing identifies V600E B-RAF amplification-mediated acquired B-RAF inhibitor resistance", Nature Communications, vol. 3, No. 724, Mar. 6, 2012, 8 pages.
Takano, T. et al., "Epidermal Growth Factor Receptor Gene Mutations and Increased Copy Numbers Predict Gefitinib Sensitivity in Patients With Recurrent Non-Small-Cell Lung Cancer", Journal of Clinical Oncology, vol. 23, No. 28, Oct. 1, 2005, 6829-6837.
Takara Biomedicals, , "Competitive PCR Guide", Lit. # L0126, Aug. 1999, 9 pages.
Tounta, G. et al., "A Multiplex PCR for Non-invasive Fetal RHD Genotyping Using Cell-free Fetal DNA", in vivo, vol. 25, 2011, 411-418.
Tynan, J. A. et al., "Restriction Enzyme-Mediated Enhanced Detection of Circulating Cell-Free Fetal DNA in Maternal Plasma", The Journal of Molecular Diagnostics, vol. 13, No. 4, Jul. 2011, 382-389.
Tzimagiorgis, G. et al., "Recovering circulating extracellular or cell-free RNA from bodily fluids", Cancer Epidemiology, vol. 35, 2011, 580-589.
Wapner, R. J. et al., "Expanding the scope of noninvasive prenatal testing: detection of fetal microdeletion syndromes", American Journal of Obstetrics & Gynecology, vol. 212, Dec. 17, 2014, 1.e1-1.e9.
Widlak, P. et al., "Cleavage Preferences of the Apoptotic Endonuclease DFF 40 (Caspase-activated DNase or Nuclease) on Naked DNA and Chromatin Substrates", The Journal of Biological Chemistry, vol. 275, No. 11, Mar. 17, 2000, 8228-8232.
Yung, T. K. et al., "Single-Molecule Detection of Epidermal Growth Factor Receptor Mutations in Plasma by Microfluidics Digital PCR in Non-Small Cell Lung Cancer Patients", Clinical Cancer Research, vol. 15, Mar. 10, 2009, 2076-2084.
Zachariah, R. et al., "Circulating cell-free DNA as a potential biomarker for minimal and mild endometriosis", Reproductive BioMedicine Online, vol. 18, No. 3, Jan. 27, 2009, 4007-411.

(56) References Cited

OTHER PUBLICATIONS

Gundry, C. N. et al., "Base-pair neutral homozygotes can be discriminated by calibrated high-resolution melting of small amplicons", Nucleic Acids Research, vol. 36, No. 10, Apr. 29, 2008, 3401-3408.

Liu, Y. Y. et al., "Predominant Hematopoietic Origin of Cell-free DNA in Plasma and Serum after Sex-mismatched Bone Marrow Transplantation", Clinical Chemistry, vol. 48, No. 3, 2002, 421-427.

Wang, W.-P. et al., "Multiplex single nucleotide polymorphism genotyping by adapter ligation-mediated allele-specific amplification", Analytical Biochemistry, vol. 355, May 5, 2006, 240-248.

Andras, S. C. et al., "Strategies for Signal Amplification in Nucleic Acid Detection", Molecular Biotechnology, vol. 19, 2001, 29-44.

Bai, H. et al., "Detection and Clinical Significance of Intratumoral EGFR Mutational Heterogeneity in Chinese Patients with Advanced Non-Small Cell Lung Cancer", PLOS One, vol. 8, No. 2, Feb. 2013, 7 pages.

Diehl, F. et al., "Detection and quantification of mutations in the plasma of patients with colorectal tumors", PNAS, vol. 102, No. 45, Nov. 8, 2005, 16368-16373.

Fouquet, C. et al., "Rapid and Sensitive p53 Alteration Analysis in Biopsies from Lung Cancer Patients Using a Functional Assay and a Universal Oligonudeotide Array: A Prospective Study", Clinical Cancer Research, vol. 10, May 15, 2004, 3479-3489.

Spertini, D. et al., "Screening of Transgenic Plants by Amplification of Unknown Genomic DNA Flanking T-DNA", BioTechniques, vol. 27, Aug. 1999, 308-314.

\* cited by examiner

METHODS FOR MULTIPLEX PCR AMPLIFICATION OF TARGET LOCI IN A NUCLEIC ACID SAMPLE

RELATED APPLICATIONS

This application is a continuation of U.S. Utility application Ser. No. 16/012,667 filed Jun. 19, 2018. U.S. Utility application Ser. No. 16/012,667 is a continuation of U.S. Utility application Ser. No. 13/335,043 filed Dec. 22, 2011, now U.S. Pat. No. 10,113,196. U.S. Utility application Ser. No. 13/335,043, now U.S. Pat. No. 10,113,196, claims the benefit of U.S. Provisional Application Ser. No. 61/426,208, filed Dec. 22, 2010, and is a continuation-in-part of U.S. Utility application Ser. No. 13/300,235, filed Nov. 18, 2011, now U.S. Pat. No. 10,017,812. U.S. Utility application Ser. No. 13/300,235, now U.S. Pat. No. 10,017,812, claims the benefit of U.S. Provisional Application Ser. No. 61/571,248, filed Jun. 23, 2011; U.S. Provisional Application Ser. No. 61/542,508, filed Oct. 3, 2011; and is a continuation-in-part of U.S. Utility application Ser. No. 13/110,685, filed May 18, 2011, now U.S. Pat. No. 8,825,412. U.S. Utility application Ser. No. 13/110,685, now U.S. Pat. No. 8,825,412, claims the benefit of U.S. Provisional Application Ser. No. 61/395,850, filed May 18, 2010; U.S. Provisional Application Ser. No. 61/398,159, filed Jun. 21, 2010; U.S. Provisional Application Ser. No. 61/462,972, filed Feb. 9, 2011; U.S. Provisional Application Ser. No. 61/448,547, filed Mar. 2, 2011; and U.S. Provisional Application Ser. No. 61/516, 996, filed Apr. 12, 2011, and the entirety of all these applications are hereby incorporated herein by reference for the teachings therein.

FIELD

The present disclosure relates generally to methods for non-invasive prenatal paternity testing.

BACKGROUND

Unclear parentage is a significant problem, and estimates range between 4% and 10% of children who believe their biological father to be a man who is not their actual biological father. In cases where a woman is pregnant, but relevant individuals are not sure who the biological father is, there are several options to determine the correct biological father of the fetus. One method is to wait until birth, and conduct genetic fingerprinting on the child and compare the genetic fingerprint of the child's genome with that of the suspected fathers. However, the mother often wishes to know the identity of the biological father of her fetus prenatally. Another method is to perform chorionic villus sampling in the first trimester or amniocentesis in the second trimester, and use the genetic material retrieved to conduct genetic fingerprinting prenatally. However, these methods are invasive, and carry a significant risk of miscarriage.

It has recently been discovered that fetal cell-free DNA (cfDNA) and intact fetal cells can enter maternal blood circulation. Consequently, analysis of this fetal genetic material can allow early Non-Invasive Prenatal Genetic Diagnosis (NIPGD or NPD). A key challenge in performing NIPGD on fetal cells is the task of identifying and extracting fetal cells or nucleic acids from the mother's blood. The fetal cell concentration in maternal blood depends on the stage of pregnancy and the condition of the fetus, but estimates range from one to forty fetal cells in every milliliter of maternal blood, or less than one fetal cell per 100,000 maternal nucleated cells. Current techniques are able to isolate small quantities of fetal cells from the mother's blood, although it is difficult to enrich the fetal cells to purity in any quantity. The most effective technique in this context involves the use of monoclonal antibodies, but other techniques used to isolate fetal cells include density centrifugation, selective lysis of adult erythrocytes, and FACS. A key challenge is performing NIPGD on fetal cfDNA is that it is typically mixed with maternal cfDNA, and thus the analysis of the cfDNA is hindered by the need to account for the maternal genotypic signal. Fetal DNA analysis has been demonstrated using PCR amplification using primers that are designed to hybridize to sequences that are specific to the paternally inherited genes. These sources of fetal genetic material open the door to non-invasive prenatal diagnostic techniques.

Once the fetal DNA has been isolated, either pure or in a mixture, it may be amplified. There are a number of methods available for whole genome amplification (WGA): ligation-mediated PCR (LM-PCR), degenerate oligonucleotide primer PCR (DOP-PCR), and multiple displacement amplification (MDA). There are a number of methods available for targeted amplification including PCR, and circularizing probes such as MOLECULAR INVERSION PROBES (MIPs), and PADLOCK probes. There are other methods that may be used for preferentially enrich fetal DNA such as size separation and hybrid capture probes.

There are numerous difficulties in using DNA amplification in these contexts. Amplification of single-cell DNA, DNA from a small number of cells, or from smaller amounts of DNA, by PCR can fail completely. This is often due to contamination of the DNA, the loss of the cell, its DNA, or accessibility of the DNA during the amplification reaction. Other sources of error that may arise in measuring the fetal DNA by amplification and microarray analysis include transcription errors introduced by the DNA polymerase where a particular nucleotide is incorrectly copied during PCR, and microarray reading errors due to imperfect hybridization on the array. Another problem is allele drop-out (ADO) defined as the failure to amplify one of the two alleles in a heterozygous cell.

Many techniques exist which provide genotyping data. Some examples include the following. TAQMAN is a unique genotyping technology produced and distributed by LIFE TECHNOLOGY. TAQMAN uses polymerase chain reaction (PCR) to amplify sequences of interest. AFFYMETRIX's 500K ARRAYS and ILLUMINA's INFINIUM system are genotyping arrays that detect for the presence of specific sequences of DNA at a large number of locations simultaneously. ILLUMINA's HISEQ and MISEQ, and LIFE TECHNOLOGY's ION TORRENT and SOLID platform allow the direct sequencing of a large number of individual DNA sequences.

SUMMARY

Disclosed herein are methods for determining the paternity of a gestating fetus in a non-invasive manner. According to aspects illustrated herein, in an embodiment, a method for establishing whether an alleged father is the biological father of a fetus that is gestating in a pregnant mother includes obtaining genetic material from the alleged father, obtaining a blood sample from the pregnant mother, making genotypic measurements, at a plurality of polymorphic loci, on the genetic material from the alleged father, obtaining genotypic measurements, at the plurality of polymorphic loci, from the genetic material from the pregnant mother, making genotypic measurements on a mixed sample of DNA originating from the blood sample from the pregnant mother, where the mixed sample of DNA comprises fetal DNA and maternal DNA, determining, on a computer, the probability that the alleged father is the biological father of the fetus gestating in the pregnant mother using the genotypic measurements made from the DNA from the alleged father, the genotypic measurements obtained from the pregnant mother, and the genotypic measurements made on the mixed sample of DNA, and establishing whether the alleged father is the biological father of the fetus using the determined probability that the alleged father is the biological father of the fetus.

In an embodiment, the polymorphic loci comprise single nucleotide polymorphisms. In an embodiment, the mixed sample of DNA comprises DNA that was from free floating DNA in a plasma fraction of the blood sample from the pregnant mother. In an embodiment, the mixed sample of DNA comprises maternal whole blood or a fraction of maternal blood containing nucleated cells. In an embodiment, the fraction of maternal blood containing nucleated cells has been enriched for cells of fetal origin.

In an embodiment, the determination of whether the alleged father is the biological father includes calculating a test statistic for the alleged father and the fetus, wherein the test statistic indicates a degree of genetic similarity between the alleged father and the fetus, and wherein the test statistic is based on the genotypic measurements made from DNA from the alleged father, the genotypic measurements made from the mixed sample of DNA, and the genotypic measurements obtained from DNA from the pregnant mother, calculating a distribution of a test statistic for a plurality of individuals who are genetically unrelated to the fetus, where each calculated test statistic indicates a degree of genetic similarity between an unrelated individual from the plurality of individuals who are unrelated to the fetus and the fetus, wherein the test statistic is based on genotypic measurements made from DNA from the unrelated individual, the genotypic measurements made from the mixed sample of DNA, and genotypic measurements obtained from DNA from the pregnant mother, calculating a probability that the test statistic calculated for the alleged father and the fetus is part of the distribution of the test statistic calculated for the plurality of unrelated individuals and the fetus, and determining the probability that the alleged father is the biological father of the fetus using the probability that the test statistic calculated for the alleged father is part of the distribution of the test statistic calculated for the plurality of unrelated individuals and the fetus. In an embodiment, establishing whether an alleged father is the biological father of the fetus also includes establishing that the alleged father is the biological father of the fetus by rejecting a hypothesis that the alleged father is unrelated to the fetus if the probability that the alleged father is the biological father of the fetus is above an upper threshold, or establishing that the alleged father is not the biological father of the fetus by not rejecting a hypothesis that the alleged father is unrelated to the fetus if the probability that the alleged father is the biological father of the fetus is below a lower threshold, or not establishing whether an alleged father is the biological father of the fetus if the likelihood is between the lower threshold and the upper threshold, or if the likelihood was not determined with sufficiently high confidence.

In an embodiment, determining the probability that the alleged father is the biological father of the fetus includes obtaining population frequencies of alleles for each locus in the plurality of polymorphic loci, creating a partition of possible fractions of fetal DNA in the mixed sample of DNA that range from a lower limit of fetal fraction to an upper limit of fetal fraction, calculating a probability that the alleged father is the biological father of the fetus given the genotypic measurements obtained from DNA from the mother, the genotypic measurements made from DNA from the alleged father, the genotypic measurements made from the mixed sample of DNA, for each of the possible fetal fractions in the partition, determining the probability that the alleged father is the biological father of the fetus by combining the calculated probabilities that the alleged father is the biological father of the fetus for each of the possible fetal fractions in the partition, calculating a probability that the alleged father is not the biological father of the fetus given the genotypic measurements made from DNA from the mother, the genotypic measurements made from the mixed sample of DNA, the obtained allele population frequencies; for each of the possible fetal fractions in the partition, and determining the probability that the alleged father is not the biological father of the fetus by combining the calculated probabilities that the alleged father is not the biological father of the fetus for each of the possible fetal fractions in the partition.

In an embodiment, calculating the probability that the alleged father is the biological father of the fetus and calculating the probability that the alleged father is not the biological father of the fetus may also include calculating, for each of the plurality of polymorphic loci, a likelihood of observed sequence data at a particular locus using a platform response model, one or a plurality of fractions in the possible fetal fractions partition, a plurality of allele ratios for the mother, a plurality of allele ratios for the alleged father, and a plurality of allele ratios for the fetus, calculating a likelihood that the alleged father is the biological father by combining the likelihood of the observed sequence data at each polymorphic locus over all fetal fractions in the partition, over the mother allele ratios in the set of polymorphic loci, over the alleged father allele ratios in the set of polymorphic loci, and over the fetal allele rations in the set of polymorphic loci, calculating a likelihood that the alleged father is not the biological father by combining the likelihood of the observed sequence data at each polymorphic locus over all fetal fractions in the partition, over the mother allele ratios in the set of polymorphic loci, over population frequencies for the set of polymorphic loci, and over the fetal allele ratios in the set of polymorphic loci, calculating a probability that the alleged father is the biological father based on the likelihood that the alleged father is the biological father, and calculating a probability that the alleged father is not the biological father based on the likelihood that the alleged father is not the biological father.

In an embodiment, calculating the probability that the alleged father is the biological father based on the likelihood that the alleged father is the biological father is performed using a maximum likelihood estimation, or a maximum a posteriori technique. In an embodiment, establishing whether an alleged father is the biological father of a fetus may also include establishing that the alleged father is the biological father if the calculated probability that the alleged father is the biological father of the fetus is significantly greater than the calculated probability that the alleged father is not the biological father, or establishing that the alleged father is not the biological father of the fetus if the calculated probability that the alleged father is the biological father is significantly greater than the calculated probability that the alleged father is not the biological father. In an embodiment, the polymorphic loci correspond to chromosomes that have a high likelihood of being disomic.

In an embodiment, the partition of possible fractions of fetal DNA contains only one fetal fraction, and where the fetal fraction is determined by a technique taken from the list consisting of quantitative PCR, digital PCR, targeted PCR, circularizing probes, other methods of DNA amplification, capture by hybridization probes, other methods of preferential enrichment, SNP microarrays, DNA microarrays, sequencing, other techniques for measuring polymorphic alleles, other techniques for measuring non-polymorphic alleles, measuring polymorphic alleles that are present in the genome of the father but not present in the genome of the mother, measuring non-polymorphic alleles that are present in the genome of the father but not present in the genome of the mother, measuring alleles that are specific to the Y-chromosome, comparing the measured amount of paternally inherited alleles to the measured amount of maternally inherited alleles, maximum likelihood estimates, maximum a posteriori techniques, and combinations thereof. In an embodiment, the method of claim 1, wherein the partition of possible fetal fractions contains only one fetal fraction, and where the fetal fraction is determined using the method of claim 26.

In an embodiment, the alleged father's genetic material is obtained from tissue selected from the group consisting of: blood, somatic tissue, sperm, hair, buccal sample, skin, other forensic samples, and combinations thereof. In an embodiment, a confidence is computed for the established determination of whether the alleged father is the biological father of the fetus. In an embodiment, the fraction of fetal DNA in the mixed sample of DNA has been enriched using a method selected from the group consisting of: size selection, universal ligation mediated PCR, PCR with short extension times, other methods of enrichment, and combinations thereof.

In an embodiment, obtaining genotypic measurements from the genetic material of pregnant mother may include making genotypic measurements on a sample of genetic material from the pregnant mother that consists essentially of maternal genetic material. In an embodiment, obtaining genotypic measurements from the genetic material from the pregnant mother may include inferring which genotypic measurements from the genotypic measurements made on the mixed sample of DNA are likely attributable to genetic material from the pregnant mother, and using those genotypic measurements that were inferred to be attributable to genetic material from the mother as the obtained genotypic measurements. In an embodiment, the method may also include making a clinical decision based on the established paternity determination. In an embodiment, the clinical decision is to terminate a pregnancy.

In an embodiment, making genetotypic measurements may be done by measuring genetic material using a technique or technology selected from the group consisting of padlock probes, molecular inversion probes, other circularizing probes, genotyping microarrays, SNP genotyping assays, chip based microarrays, bead based microarrays, other SNP microarrays, other genotyping methods, Sanger DNA sequencing, pyrosequencing, high throughput sequencing, targeted sequencing using circularizing probes, targeted sequencing using capture by hybridization probes, reversible dye terminator sequencing, sequencing by ligation, sequencing by hybridization, other methods of DNA sequencing, other high throughput genotyping platforms, fluorescent in situ hybridization (FISH), comparative genomic hybridization (CGH), array CGH, and multiples or combinations thereof.

In an embodiment, making genotypic measurements may be done on genetic material that is amplified and/or preferentially enriched prior to being measured using a technique or technology that is selected from the group consisting of: Polymerase Chain Reaction (PCR), ligand mediated PCR, degenerative oligonucleotide primer PCR, targeted amplification, PCR, mini-PCR, universal PCR amplification, Multiple Displacement Amplification (MDA), allele-specific PCR, allele-specific amplification techniques, linear amplification methods, ligation of substrate DNA followed by another method of amplification, bridge amplification, padlock probes, circularizing probes, capture by hybridization probes, and combinations thereof.

In an embodiment, the method may also include generating a report comprising the established paternity of the fetus. In an embodiment, the invention may comprise a report disclosing the established paternity of the fetus generated using a method described herein.

Disclosed herein are methods for determining the fraction of DNA originating from a target individual is present in a mixture of DNA that contains DNA from the target individual, and also DNA from at least one other individual. According to aspects illustrated herein, in an embodiment, a method for determining a fraction of DNA from a target individual present in a mixed sample of DNA that comprises DNA from the target individual and DNA from a second individual may include making genotypic measurements at a plurality of polymorphic loci from the mixed sample of DNA, obtaining genotypic data at the plurality of polymorphic loci from the second individual, and determining, on a computer, the fraction of DNA from the target individual present in the mixed sample using the genotypic measurements from the mixed sample of DNA, the genotypic data from the second individual, and probabilistic estimation techniques.

In an embodiment, obtaining genotypic data from the second individual includes making genetic measurements from DNA that consists essentially of DNA from the second individual. In an embodiment, obtaining genotypic data from the second individual may include inferring which genotypic measurements from the genotypic measurements made on the mixed sample of DNA are likely attributable to genetic material from the second individual, and using those genotypic measurements that were inferred to be attributable to genetic material from the second individual as the obtained genotypic measurements.

In an embodiment, inferring the genotypic data of the related individual may also include using allele population frequencies at the loci. In an embodiment, the determined fraction of DNA from a target individual is expressed as a probability of fractions of DNA. In an embodiment, the genotypic measurements made from the mixed sample comprise genotypic measurements made by sequencing the DNA in the mixed sample. In an embodiment, the DNA in the mixed sample is preferentially enriched at the plurality of polymorphic loci prior to making genotypic measurements from the mixed sample of DNA. In an embodiment, the polymorphic loci comprise single nucleotide polymorphisms.

In an embodiment, determining the fraction may also include determining a probability of a plurality of fractions of DNA from the target individual present in the mixed sample of DNA, determining the fraction by selecting the fraction from the plurality of fractions with the largest probability. In an embodiment, determining the fraction may also include determining a probability of a plurality of fractions of DNA from the target individual present in the mixed sample of DNA, using a maximum likelihood estimation technique to determine the most likely fraction, and determining the fraction by selecting the fraction that was determined to be the most likely.

In an embodiment, the target individual is a fetus gestating in a pregnant mother, and the second individual is the pregnant mother. In an embodiment, the method may also include using a platform model that relates genotypic data measured at the polymorphic loci, and using a table that relates maternal genotypes to child genotypes. In an embodiment, the determination also uses genotypic measurements at a plurality of polymorphic loci measured on DNA from the father of the fetus. In an embodiment, the method does not make use of genotypic data from the father of the fetus. In an embodiment, the method does not make use of loci on the Y chromosome. In an embodiment, the invention may comprise a report disclosing an established paternity of the fetus determined using a method disclosed herein for determining the fraction of fetal DNA present in the maternal plasma. In an embodiment, the invention may comprise a report disclosing a ploidy state of the fetus determined using a method disclosed herein for determining the fraction of fetal DNA present in the maternal plasma.

BRIEF DESCRIPTION OF THE DRAWINGS

The presently disclosed embodiments will be further explained with reference to the attached drawings, wherein like structures are referred to by like numerals throughout the several views. The drawings shown are not necessarily to scale, with emphasis instead generally being placed upon illustrating the principles of the presently disclosed embodiments.

Figure 1:
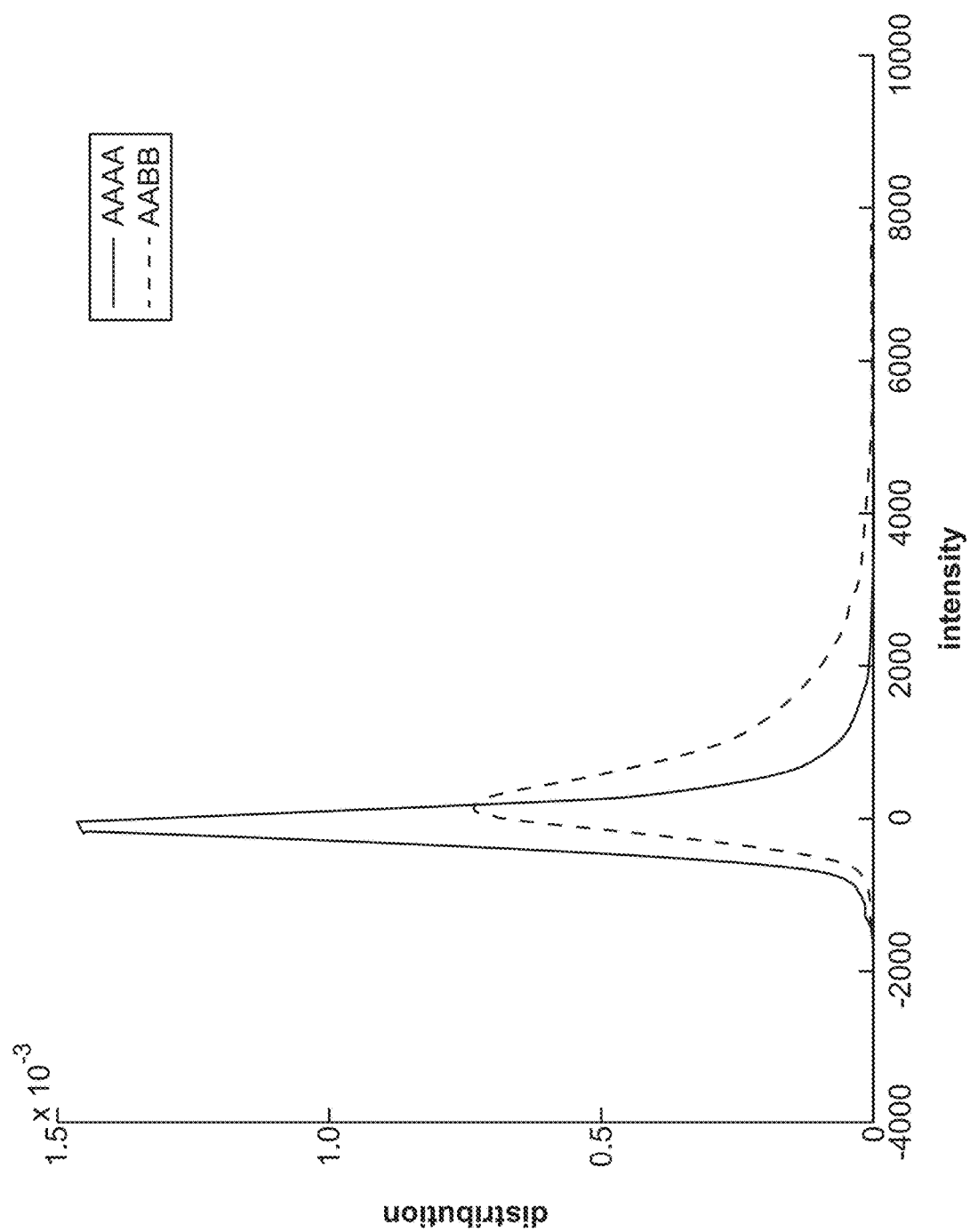
FIG. 1 shows the distribution of allele intensities from two parental contexts as measured on maternal plasma.

While the above-identified drawings set forth presently disclosed embodiments, other embodiments are also contemplated, as noted in the discussion. This disclosure presents illustrative embodiments by way of representation and not limitation. Numerous other modifications and embodiments can be devised by those skilled in the art which fall within the scope and spirit of the principles of the presently disclosed embodiments.

DETAILED DESCRIPTION

According to aspects illustrated herein, a method is provided for determining whether or not an alleged father is the biological father of a fetus that is gestating in a pregnant mother. In an embodiment, the method includes obtaining genetic material from the alleged father, and obtaining a blood sample from the pregnant mother. In an embodiment, the method may include making genotypic measurements of the alleged father and the pregnant mother, and making genotypic measurements on the free floating DNA (ffDNA, i.e. cfDNA) found in the plasma of the pregnant mother. In an embodiment, the method includes obtaining genotypic data for a set of SNPs of the mother and alleged father of the fetus; making genotypic measurements for the set of SNPs on a mixed sample that comprises DNA from the target individual and also DNA from the mother of the target individual. In an embodiment, the method may include using the genotypic measurements to determine, on a computer, the probability that the alleged father is the biological father of the fetus gestating in the pregnant mother. In an embodiment, the method may include using the genotypic data of the pregnant mother and the alleged father to determine an expected allelic distribution for the genotypic measurements of the fetal/maternal DNA mixture if the alleged father were the biological father of the fetus. In an embodiment, the method may include using the genotypic data of the pregnant mother and genotypic data of a plurality of individuals known not to be the father to determine an expected allelic distribution for the genotypic measurements of the fetal/maternal DNA mixture if the alleged father is not the biological father of the fetus. In an embodiment, the method may involve calculating the probabilities that the alleged father is the biological father of the fetus given the expected allelic distributions, and the actual maternal plasma DNA measurements. In an embodiment, the series of steps outlined in the method results in a transformation of the genetic material of the pregnant mother and the alleged father to produce and determine the correct identity of the biological father of a gestating fetus prenatally and in a non-invasive manner. In an embodiment, determining the likelihood that the alleged father is the biological father includes calling or establishing the alleged father as the biological father if the likelihood that the father is excluded from the allelic distribution created using the plurality of unrelated individuals is above a threshold. In an embodiment, determining the likelihood that the alleged father is the biological father includes calling the alleged father as not the biological father if the likelihood that the alleged father is excluded from the allelic distribution created using the plurality of unrelated individuals is below a threshold. In an embodiment, the paternity determination is made by initially assuming that the alleged father is in fact the father of the child; if the alleged father is incorrect, the child genotypes will not fit these predictions, and the initial assumption is considered to be wrong; however, if the child genotypes do fit the predicitions, then the assumption is considered to be correct. Thus, the paternity test considers how well the observed ffDNA fits the child genotypes predicted by the alleged father's genotypes. In an embodiment, an electronic or physical report may be generated stating the paternity determination.

In an embodiment, the paternity determination is made using genetic measurements of free-floating DNA (ffDNA) found in maternal blood, and the genotype information from the mother and alleged father. The general method could be applied to measurements of ffDNA using a variety of platforms such as SNP microarrays, untargeted high throughput sequencing, or targeted sequencing. The methods discussed here address the fact that free-floating fetal DNA is found in maternal plasma at low yet unknown concentrations and is difficult to detect. The paternity test may comprise evaluating the ffDNA measurements and how likely they are to have been generated by the alleged father, based on his genotypes. Regardless of the measurement platform, the test may be based on the genotypes measured at polymorphic locations. In some embodiments the possible alleles at each polymorphic locus may be generalized to A and B, and optionally C, D, and/or E, etc.

In an embodiment, this method involves using allele measurement data from a plurality of loci. In an embodiment, the loci are polymorphic. In an embodiment, some or most of the loci are polymorphic. In an embodiment, the polymorphic loci are single nucleotide polymorphisms (SNPs). In an embodiment, some or most of the polymorphic loci are heterozygous. In an embodiment, it is not necessary to determine which loci are heterozygous in advance of the testing.

In an embodiment, a method disclosed herein uses selective enrichment techniques that preserve the relative allele frequencies that are present in the original sample of DNA at each polymorphic locus from a set of polymorphic loci. In some embodiments the amplification and/or selective enrichment technique may involve PCR techniques such as mini-PCR or ligation mediated PCR, fragment capture by hybridization, or circularizing probes such as Molecular Inversion Probes. In some embodiments, methods for amplification or selective enrichment may involve using PCR primers or other probes where, upon correct hybridization to the target sequence, the 3-prime end or 5-prime end of a nucleotide probe is separated from the polymorphic site of the allele by a small number of nucleotides. In an embodiment, probes in which the hybridizing region is designed to hybridize to a polymorphic site are excluded. These embodiments are improvements over other methods that involve targeted amplification and/or selective enrichment in that they better preserve the original allele frequencies of the sample at each polymorphic locus, whether the sample is pure genomic sample from a single individual or mixture of individuals.

In an embodiment, a method disclosed herein uses highly efficient highly multiplexed targeted PCR to amplify DNA followed by high throughput sequencing to determine the allele frequencies at each target locus. One technique that allows highly multiplexed targeted PCR to perform in a highly efficient manner involves designing primers that are unlikely to hybridize with one another. The PCR probes may be selected by creating a thermodynamic model of potentially adverse interactions, or unintended interactions, between at least 500, at least 1,000, at least 5,000, at least 10,000, at least 20,000, at least 50,000, or at least 100,000 potential primer pairs, or between primers and sample DNA, and then using the model to eliminate designs that are incompatible with other the designs in the pool, or with the sample DNA. Another technique that allows highly multiplexed targeted PCR to perform in a highly efficient manner is using a partial or full nesting approach to the targeted PCR. Using one or a combination of these approaches allows multiplexing of at least 300, at least 800, at least 1,200, at least 4,000 or at least 10,000 primers in a single pool with the resulting amplified DNA comprising a majority of DNA molecules that, when sequenced, will map to targeted loci. Using one or a combination of these approaches allows multiplexing of a large number of primers in a single pool with the resulting amplified DNA comprising greater than 50%, greater than 80%, greater than 90%, greater than 95%, greater than 98%, or greater than 99% DNA molecules that map to targeted loci.

In an embodiment, a method disclosed herein involves determining whether the distribution of observed allele measurements is indicative of a paternity inclusion or exclusion using a maximum likelihood estimation (MLE) technique. The use of a maximum likelihood estimation technique is different from and a significant improvement over methods that use single hypothesis rejection technique in that the resultant determinations will be made with significantly higher accuracy. One reason is that single hypothesis rejection techniques does not contain information on the alternative hypothesis. Another reason is that the maximum likelihood technique allows for the determination of optimal cutoff thresholds for each individual sample. Another reason is that the use of a maximum likelihood technique allows the calculation of a confidence for each paternity determination. The ability to make a confidence calculation for each determination allows a practitioner to know which calls are accurate, and which are more likely to be wrong. In some embodiments, a wide variety of methods may be combined with a maximum likelihood estimation technique to enhance the accuracy of the ploidy calls. In an embodiment, a method disclosed herein involves estimating the fetal fraction of DNA in the mixed sample and using that estimation to calculate both the paternity call (determination) and the confidence of the paternity call.

In an embodiment, the method involves calculating a test statistic that is indicative of the degree of relatedness between a first individual and a second individual, given genotypic measurements at a plurality of polymorphic loci for the first individual, and genotypic measurements at a plurality of polymorphic loci for a mixture of DNA where the mixture of DNA comprises DNA from the second individual and a related individual. In an embodiment, the first individual is an alleged father, the second individual is a gestating fetus, and the related individual is the mother of the fetus. The test statistic may be calculated for the fetus, the mother, and a plurality of individuals known to be unrelated to the fetus, thereby generating a distribution of the metric for unrelated individuals. The test statistic may also be calculated for the fetus, the mother, and the alleged father. A single hypothesis rejection test may be used to determine if the test statistic calculated using the alleged father's genotypic data is part of the distribution of test statistics calculated using the genotypic data of the unrelated individuals. If the test statistic calculated using the alleged father's genotypic data is found to be part of the distribution of test statistics calculated using the genotypic data of the unrelated individuals, then paternity can be excluded, that is, the alleged father may be determined to not be related to the fetus. If the test statistic calculated using the alleged father's genotypic data is found not to be part of the distribution of test statistics calculated using the genotypic data of the unrelated individuals, then paternity can be included, that is, the alleged father may be determined to be related to the fetus.

In an embodiment, the paternity determination involves determining the probability of the measured genotypic data given two possible hypotheses: the hypothesis that the alleged father is the biological father of the fetus, and the hypothesis that the alleged father is not the biological father of the fetus. A probability can then be calculated for each of the hypotheses given the data, and the paternity may be established based on the likelihood of each of the two hypotheses. The determination may utilize genetic measurements made on the maternal plasma, genetic measurements made on DNA from the alleged father, and optionally maternal genotypic data. In an embodiment, the maternal genotypic data can be inferred from the genotypic measurements made on the maternal plasma. In an embodiment, the probability can be determined using a partition of the range of possible fetal fractions; the range of fetal fractions could be anywhere from 0.01% to 99.9%, and the mesh may have increments ranging from 10% to 1%, from 1% to 0.1%, and lower than 0.1%. In an embodiment, the partition of possible fetal fractions may be from 2% to 30%, and the increments are about 1%. In an embodiment, the mesh could be continuous, and the likelihoods could be intergrated over the ranges rather than combined. In an embodiment, the probability can be determined using only one fetal fraction, where that fetal fraction may be determined using any appropriate method. For each possible fetal fraction in the mesh, one can calculate the probability of the data given the two hypotheses. For the hypothesis that the alleged father is the biological father, the alleged father genotypes may be used in the calculation of the probability, while for the hypothesis that the alleged father is not the biological father, population based allele frequency data may additionally be used in the calculation of the probability. In an embodiment, one can use the parent contexts and a platform model in calculating the likelihood of data given hypothesis. In an embodiment, the likelihoods can be combined over all fetal fractions in the partition, over all mother genotypes, and over all father genotypes. In an embodiment, the parental genotypes may be probabilistic (e.g. at a given SNP, a parent may have the genotype GT with 99% chance, GG with 0.5% chance, and TT with 0.5% chance; in another embodiment the parental genotypes may take on one value (e.g. at a given SNP, a parent has the genotype GT). In some embodiments the terms probability and likelihood may be interchangeable, as in common parlance; in other embodiments, the two terms may not be interchangeable, and may be read as one skilled in the art in statistics would read them.

In some methods known in the art, fetal fraction is determined using measurements made at loci that are found exclusively on the paternal genotype, for example, loci that are found exclusively on the Y-chromosome, or the Rhesus-D gene. Unfortunately, these methods require either that the fetus is male (in the case where the loci are found exclusively on the Y chromosome) or that a gene or set of genes can be identified prior to measurements of the DNA where those genes are present on the paternal genotype, and not present in the maternal genotype. An additional complication is that in the context of paternity testing, it is not known whether or not the alleged father is the biological father, and therefore, with the exception of the Y-chromosome specific loci, it is not possible to determine what loci may be present on the father, and not on the mother. Therefore, in the context of paternity testing, it is not currently possible to determine the fetal fraction when the fetus is a female, and when the fetus is male, fetal fraction can only be determined by using Y-chromosome specific loci. In an embodiment, a method is disclosed herein for determining the fraction of fetal DNA that is present in the mixture of DNA comprising maternal and fetal DNA. In an embodiment, the method can determine the fetal fraction of fetal DNA that is present in the mixture of DNA comprising maternal and fetal DNA using genotypic measurements from autosomal chromosomes. In an embodiment, the method can determine the fetal fraction of fetal DNA that is present in the mixture of DNA comprising maternal and fetal DNA irrespective of the sex of the fetus. In an embodiment, the method can determine the fetal fraction of fetal DNA that is present in the mixture of DNA comprising maternal and fetal DNA irrespective of what genes the mother and alleged father may have. The instant method does not require that the fetus be male, or that a locus or loci can be identified that are present on the father and not on the mother. The instant method does not require that the paternal genotype be known. The instant method does not require that the maternal genotype be known, as it can be inferred from the measurements made on the DNA in the maternal plasma, which comprises a mixture of both fetal and maternal DNA.

In an embodiment, the distribution of polymprohic loci can be modeled using a binomial distribution. In an embodiment, the distribution of polymorphic loci can be modeled using a beta-binomial distribution. By using the beta-binomial distribution as a model for allele distribution, one can more accurately model likely allele measurements than when using other distributions; this can result in more accurate paternity determinations.

In an embodiment, a method disclosed herein takes into account the tendency for the data to be noisy and contain errors by attaching a probability to each measurement. The use of maximum likelihood techniques to choose the correct hypothesis from the set of hypotheses that were made using the measurement data with attached probabilistic estimates makes it more likely that the incorrect measurements will be discounted, and the correct measurements will be used in the calculations that lead to the paternity determination. To be more precise, this method systematically reduces the influence of incorrectly measured data on the paternity determination. This is an improvement over methods where all data is assumed to be equally correct or methods where outlying data is arbitrarily excluded from calculations leading to a paternity determination. In an embodiment, individual SNPs are weighted by expected measurement variance based on the SNP quality and observed depth of read; this may result in an increase in the accuracy of the resulting statistic, resulting in an increase of the accuracy of the paternity call significantly, especially in borderline cases.

The methods described herein are particularly advantageous when used on samples where a small amount of DNA is available, or where the percent of fetal DNA is low. This is due to the correspondingly higher allele dropout rate that may occur when only a small amount of DNA is available and/or the correspondingly higher fetal allele dropout rate when the percent of fetal DNA is low in a mixed sample of fetal and maternal DNA. A high allele dropout rate, meaning that a large percentage of the alleles were not measured for the target individual, results in poorly accurate fetal fraction calculations, and poorly accurate paternity determinations. The methods described herein allow for an accurate ploidy determination to be made when the percent of molecules of DNA that are fetal in the mixture is less than 40%, less than 30%, less than 20%, less than 10%, less than 8%, less than 6%, less than 4%, and even less than 3%.

In an embodiment, it is possible to determine the paternity of an individual based on measurements when that individual's DNA is mixed with DNA of a related individual. In an embodiment, the mixture of DNA is the free floating DNA found in maternal plasma, which may include DNA from the mother, with known genotype, and which may be mixed with DNA of the fetus, with unknown genotype. The paternity of the fetus can then be determined by looking at the actual measurements, and determining the likelihood of paternity given the observed data. In some embodiments, a method disclosed herein could be used in situations where there is a very small amount of DNA present, such as in forensic situations, where one or a few cells are available (typically less than ten cells, less than twenty cells, less than 40 cells, less than 100 cells, or an equivalent amount of DNA.) In some embodiments, a method disclosed herein could be used in situations where the DNA is highly fragmented, such as ffDNA found in plasma. In these embodiments, a method disclosed herein serves to make paternity calls from a small amount of DNA that is not contaminated by other DNA, but where the paternity calling very difficult due to the small amount of DNA. The genetic measurements used as part of these methods could be made on any sample comprising DNA or RNA, for example but not limited to: blood, plasma, body fluids, urine, hair, tears, saliva, tissue, skin, fingernails, blastomeres, embryos, amniotic fluid, chorionic villus samples, feces, bile, lymph, cervical mucus, semen, or other cells or materials comprising nucleic acids. In an embodiment, a method disclosed herein could be run with nucleic acid detection methods such as sequencing, microarrays, qPCR, digital PCR, or other methods used to measure nucleic acids. In some embodiments, a method disclosed herein involves calculating, on a computer, allele ratios at the plurality of polymorphic loci from the DNA measurements made on the processed samples. In some embodiments, a method disclosed herein involves calculating, on a computer, allele ratios or allelic distributions at a plurality of polymorphic loci from the DNA measurements made on the processed samples along with any combination of other improvements described in this disclosure.

Further discussion of these points may be found elsewhere in this document.

Non-Invasive Prenatal Paternity Testing (NPPT)

The process of non-invasive prenatal paternity testing involves a number of steps. Some of the steps may include: (1) obtaining the genetic material from the fetus; (2) enriching the genetic material of the fetus that may be in a mixed sample, ex vivo; (3) amplifying the genetic material, ex vivo; (4) preferentially enriching specific loci in the genetic material, ex vivo; (5) measuring the genetic material, ex vivo; and (6) analyzing the genotypic data, on a computer, and ex vivo. Methods to reduce to practice these six and other relevant steps are described herein. At least some of the method steps are not directly applied on the body. In an embodiment, the present disclosure relates to methods of treatment and diagnosis applied to tissue and other biological materials isolated and separated from the body. At least some of the method steps are executed on a computer.

Some embodiments of the present disclosure allow a clinician to determine the genetic state of a fetus, specifically its biological relationship to another individual, that is gestating in a mother in a non-invasive manner such that the health of the baby is not put at risk by the collection of the genetic material of the fetus, and that the mother is not required to undergo an invasive procedure.

Modern technological advances have resulted in the ability to measure large amounts of genetic information from a genetic sample using such methods as high throughput sequencing and genotyping arrays. The methods disclosed herein allow a clinician to take greater advantage of the large amounts of data available, and make a more accurate diagnosis of the fetal genetic identity. In an embodiment, an informatics based method may result in paternity determinations of higher accuracy than by methods currently known in the art. The details of a number of embodiments are given below. Different embodiments may involve different combinations of the aforementioned steps. Various combinations of the different embodiments of the different steps may be used interchangeably.

In an embodiment, a blood sample is taken from a pregnant mother, and the free floating DNA in the plasma of the mother's blood, which contains a mixture of both DNA of maternal origin, and DNA of fetal origin, is isolated and used to determine the ploidy status of the fetus. In an embodiment, a method disclosed herein involves preferential enrichment of those DNA sequences in a mixture of DNA that correspond to polymorphic alleles in a way that the allele ratios and/or allele distributions remain reasonably consistent upon enrichment. In an embodiment, the method involves amplifying the isolated DNA using whole genome amplification (WGA). In an embodiment, a method disclosed herein involves targeted PCR based amplification such that a high percentage of the resulting molecules correspond to targeted loci. In an embodiment, a method disclosed herein involves sequencing a mixture of DNA that contains both DNA of maternal origin, and DNA of fetal origin. In an embodiment, the method involves measuring the amplified DNA using a microarray designed to detect nucleic acid sequences such as a SNP array. In an embodiment, a method disclosed herein involves using measured allele distributions to determine the paternity of a fetus that is gestating in a mother. In an embodiment, a method disclosed herein involves reporting the determined paternity state to a clinician. In an embodiment, a method disclosed herein involves taking a clinical action, for example, performing follow up invasive testing such as chorionic villus sampling or amniocentesis, preparing for the birth of a child, or an elective termination of a fetus.

This application makes reference to U.S. Utility application Ser. No. 11/603,406, filed Nov. 28, 2006 (US Publication No.: 20070184467); U.S. Utility application Ser. No. 12/076,348, filed Mar. 17, 2008 (US Publication No.: 20080243398); PCT Utility Application Serial No. PCT/US09/52730, filed Aug. 4, 2009 (PCT Publication No.: WO/2010/017214); PCT Utility Application Serial No. PCT/US Serial No. 10/050824, filed Sep. 30, 2010 (PCT Publication No.: WO/2011/041485), U.S. Utility application Ser. No. 13/110,685, filed May 18, 2011, and U.S. Utility application Ser. No. 13/300,235, filed Nov. 18, 2011. Some of the vocabulary used in this filing may have its antecedents in these references. Some of the concepts described herein may be better understood in light of the concepts found in these references.

Screening Maternal Blood Comprising Free Floating Fetal DNA

The methods described herein may be used to help determine whether a child, fetus, or other target individual is genetically related to another individual. In some embodiment, this may be done in cases where the genetic material of the target individual is found in the presence of a quantity of genetic material from another individual. In one embodiment, the method may be used to help determine whether a fetus is genetically related to an alleged father using the free floating fetal DNA found in the maternal blood, along with a genetic sample from the father and optionally the mother. In an embodiment, the fetus may have originated from an egg from an egg donor such that the fetus is not genetically related to the mother in which the fetus is gestating. In an embodiment, the method may be applicable in cases where the amount of target DNA is in any proportion with the non-target DNA; for example, the target DNA could make up anywhere between 0.000001 and 99.999999% of the DNA present. In an embodiment, the non-target contaminating DNA could be from a plurality of individuals; it is advantageous where genetic data from some or all of the relevant non-target individual(s) is known, or where genetic samples from said related individuals are available. In an embodiment, a method disclosed herein can be used to determine genotypic data of a fetus from maternal blood that contains fetal DNA. It may also be used in a case where there are multiple fetuses in the uterus of a pregnant woman, or where other contaminating DNA may be present in the sample, for example from other already born siblings.

This technique may make use of the phenomenon of fetal blood cells gaining access to maternal circulation through the placental villi. Ordinarily, only a very small number of fetal cells enter the maternal circulation in this fashion (not enough to produce a positive Kleihauer-Betke test for fetal-maternal hemorrhage). The fetal cells can be sorted out and analyzed by a variety of techniques to look for particular DNA sequences, but without the risks that invasive procedures inherently have. This technique may also make use of the phenomenon of free floating fetal DNA gaining access to maternal circulation by DNA release following apoptosis of placental tissue where the placental tissue in question contains DNA of the same genotype as the fetus. The free floating DNA found in maternal plasma has been shown to contain fetal DNA in proportions as high as 30-40% fetal DNA.

In an embodiment, blood may be drawn from a pregnant woman. Research has shown that maternal blood may contain a small amount of free floating DNA from the fetus, in addition to free floating DNA of maternal origin. In addition, there also may be nucleated fetal blood cells comprising DNA of fetal origin, in addition to many blood cells of maternal origin, which typically do not contain nuclear DNA. There are many methods know in the art to isolate fetal DNA, or create fractions enriched in fetal DNA. For example, chromatography has been show to create certain fractions that are enriched in fetal DNA.

Once the sample of maternal blood, plasma, or other fluid, drawn in a relatively non-invasive manner, and that contains an amount of fetal DNA, either cellular or free floating, either enriched in its proportion to the maternal DNA, or in its original ratio, is in hand, one may genotype the DNA found in said sample. In some embodiments, the blood may be drawn using a needle to withdraw blood from a vein, for example, the basilica vein. The method described herein can be used to determine genotypic data of the fetus. For example, it can be used to determine the ploidy state at one or more chromosomes, it can be used to determine the identity of one or a set of SNPs, including insertions, deletions, and translocations. It can be used to determine one or more haplotypes, including the parent of origin of one or more genotypic features. It can also be used to determine the degree of relatedness between the fetus an another individual.

Note that this method will work with any nucleic acids that can be used for any genotyping and/or sequencing methods, such as the ILLUMINA INFINIUM ARRAY platform, AFFYMETRIX GENECHIP, ILLUMINA GENOME ANALYZER, or LIFE TECHNOLOGIES' SOLID SYSTEM, along with the genotypic data measured therefrom. This includes extracted free-floating DNA from plasma or amplifications (e.g. whole genome amplification, PCR) of the same; genomic DNA from other cell types (e.g. human lymphocytes from whole blood) or amplifications of the same. For preparation of the DNA, any extraction or purification method that generates genomic DNA suitable for the one of these platforms will work as well. This method could work equally well with samples of RNA. In an embodiment, storage of the samples may be done in a way that will minimize degradation (e.g. below freezing, at about −20 C, or at a lower temperature).

Parental Support

Some embodiments may be used in combination with the PARENTAL SUPPORT™ (PS) method, embodiments of which are described in U.S. application Ser. No. 11/603,406 (US Publication No.: 20070184467), U.S. application Ser. No. 12/076,348 (US Publication No.: 20080243398), U.S. application Ser. No. 13/110,685, PCT Application PCT/US09/52730 (PCT Publication No.: WO/2010/017214), PCT Application No. PCT/US10/050824 (PCT Publication No.: WO/2011/041485), PCT Application No. PCT/US2011/037018 (PCT Publication No.: WO/2011/146632), and PCT Application No. PCT/US2011/61506, which are incorporated herein by reference in their entirety. PARENTAL SUPPORT™ is an informatics based approach that can be used to analyze genetic data. In some embodiments, the methods disclosed herein may be considered as part of the PARENTAL SUPPORT™ method. In some embodiments, The PARENTAL SUPPORT™ method is a collection of methods that may be used to determine the genetic data of a target individual, with high accuracy, of one or a small number of cells from that individual, or of a mixture of DNA consisting of DNA from the target individual and DNA from one or a plurality of other individuals, specifically to determine disease-related alleles, other alleles of interest, the ploidy state of one or a plurality of chromosomes in the target individual, and or the extent of relationship of another individual to the target individual. PARENTAL SUPPORT™ may refer to any of these methods. PARENTAL SUPPORT™ is an example of an informatics based method.

The PARENTAL SUPPORT™ method makes use of known parental genetic data, i.e. haplotypic and/or diploid genetic data of the mother and/or the father, together with the knowledge of the mechanism of meiosis and the imperfect measurement of the target DNA, and possibly of one or more related individuals, along with population based crossover frequencies, in order to reconstruct, in silico, the genotype at a plurality of alleles, and/or the paternity state of an embryo or of any target cell(s), and the target DNA at the location of key loci with a high degree of confidence. The PARENTAL SUPPORT™ method makes use of known parental genetic data, i.e. haplotypic and/or diploid genetic data of the mother and/or the father, together with the knowledge of the mechanism of meiosis and the imperfect measurement of the target DNA, to create hypotheses about what genetic data may be expected for different situations, to calculate the likelihood of each of the situations given the observed genetic data, thereby determining which situation is most likely. In some embodiments the situation is question may include whether the target individual has inherited a disease linked haplotype of interest, whether the target individual has inherited a phenotype linked haplotype of interest, whether the target individual has one or more aneuploid chromosomes, and/or whether the target individual is related to an individual of interest, and what the degree of relationship may be. The PARENTAL SUPPORT™ method allows the cleaning of noisy genetic data. PARENTAL SUPPORT™ may be particularly relevant where only a small fraction of the genetic material available is from the target individual (e.g. NPD or NPPT) and where direct measurements of the genotypes are inherently noisy due to the contaminating DNA signal from another individual. The PARENTAL SUPPORT™ method is able to reconstruct highly accurate ordered diploid allele sequences on the embryo, together with copy number of chromosomes segments, even though the conventional, unordered diploid measurements may be characterized by high rates of allele dropouts, drop-ins, variable amplification biases and other errors. The method may employ both an underlying genetic model and an underlying model of measurement error. The genetic model may determine both allele probabilities at each SNP and crossover probabilities between SNPs. Allele probabilities may be modeled at each SNP based on data obtained from the parents and model crossover probabilities between SNPs based on data obtained from the HapMap database, as developed by the International HapMap Project. Given the proper underlying genetic model and measurement error model, maximum a posteriori (MAP) estimation may be used, with modifications for computationally efficiency, to estimate the correct, ordered allele values at each SNP in the embryo.

Definitions

Single Nucleotide Polymorphism (SNP) refers to a single nucleotide that may differ between the genomes of two members of the same species. The usage of the term should not imply any limit on the frequency with which each variant occurs.

Sequence refers to a DNA sequence or a genetic sequence. It may refer to the primary, physical structure of the DNA molecule or strand in an individual. It may refer to the sequence of nucleotides found in that DNA molecule, or the complementary strand to the DNA molecule. It may refer to the information contained in the DNA molecule as its representation in silico.

Locus refers to a particular region of interest on the DNA of an individual, which may refer to a SNP, the site of a possible insertion or deletion, or the site of some other relevant genetic variation. Disease-linked SNPs may also refer to disease-linked loci.

Polymorphic Allele, also "Polymorphic Locus," refers to an allele or locus where the genotype varies between individuals within a given species. Some examples of polymorphic alleles include single nucleotide polymorphisms, short tandem repeats, deletions, duplications, and inversions.

Polymorphic Site refers to the specific nucleotides found in a polymorphic region that vary between individuals.

Allele refers to the genes that occupy a particular locus.

Genetic Data also "Genotypic Data" refers to the data describing aspects of the genome of one or more individuals. It may refer to one or a set of loci, partial or entire sequences, partial or entire chromosomes, or the entire genome. It may refer to the identity of one or a plurality of nucleotides; it may refer to a set of sequential nucleotides, or nucleotides from different locations in the genome, or a combination thereof. Genotypic data is typically in silico, however, it is also possible to consider physical nucleotides in a sequence as chemically encoded genetic data. Genotypic Data may be said to be "on," "of," "at," "from" or "on" the individual(s). Genotypic Data may refer to output measurements from a genotyping platform where those measurements are made on genetic material.

Genetic Material also "Genetic Sample" refers to physical matter, such as tissue or blood, from one or more individuals comprising DNA or RNA Confidence refers to the statistical likelihood that the called SNP, allele, set of alleles, ploidy call, or paternity call is correct.

Aneuploidy refers to the state where the wrong number of chromosomes is present in a cell. In the case of a somatic human cell it may refer to the case where a cell does not contain 22 pairs of autosomal chromosomes and one pair of sex chromosomes. In the case of a human gamete, it may refer to the case where a cell does not contain one of each of the 23 chromosomes. In the case of a single chromosome type, it may refer to the case where more or less than two homologous but non-identical chromosome copies are present, or where there are two chromosome copies present that originate from the same parent.

Chromosome may refer to a single chromosome copy, meaning a single molecule of DNA of which there are 46 in a normal somatic cell; an example is 'the maternally derived chromosome 18'. Chromosome may also refer to a chromosome type, of which there are 23 in a normal human somatic cell; an example is 'chromosome 18'.

Monosomy refers to the state where a cell only contains one of a chromosome type.

Disomy refers to the state where a cell contains two of a chromosome type.

Uniparental Disomy refers to the state where a cell contains two of a chromosome type, and where both chromosomes originate from one parent.

Trisomy refers to the state where a cell contains three of a chromosome type.

The State of the Genetic Material or simply "Genetic State" may refer to the identity of a set of SNPs on the DNA, to the phased haplotypes of the genetic material, or to the sequence of the DNA, including insertions, deletions, repeats and mutations. It may also refer to the ploidy state of one or more chromosomes, chromosomal segments, or set of chromosomal segments.

Establishing the Paternity or "Determining the Paternity" refers to establishing or determining that an alleged father either is or is not the biological father of a gestating fetus, or determining or establishing the likelihood that an alleged father is the biological father of the fetus.

Paternity Determination refers to the determination that the alleged father is or is not the biological father of the fetus. A paternity determination is the result of establishing, calling or determining the paternity.

Paternity refers to the identity of the biological father of an individual.

Paternity Inclusion refers to establishing that an alleged father is the biological father of a fetus.

Paternity Exclusion refers to establishing that an alleged father is not the biological father of a fetus.

Alleged Father refers to a male whose paternal relationship to a fetus is in question.

Biological Father of an individual refers to the male whose genetic material was inherited by the individual.

Allelic Ratio refers to the ratio between the amount of each allele at a polymorphic locus that is present in a sample or in an individual. When the sample is measured by sequencing, the allelic ratio may refer to the ratio of sequence reads that map to each allele at the locus. When the sample is measured by an intensity based measurement method, the allele ratio may refer to the ratio of the amounts of each allele present at that locus as estimated by the measurement method.

Allelic Distribution, or 'allele count distribution' refers to the relative amount of each allele that is present for each locus in a set of loci. An allelic distribution can refer to an individual, to a sample, or to a set of measurements made on a sample. In the context of sequencing, the allelic distribution refers to the number or probable number of reads that map to a particular allele for each allele in a set of polymorphic loci. The allele measurements may be treated probabilistically, that is, the likelihood that a given allele is present for a give sequence read is a fraction between 0 and 1, or they may be treated in a binary fashion, that is, any given read is considered to be exactly zero or one copies of a particular allele.

Allelic Bias refers to the degree to which the measured ratio of alleles at a heterozygous locus is different to the ratio that was present in the original sample of DNA. The degree of allelic bias at a particular locus is equal to the observed allelelic ratio at that locus, as measured, divided by the ratio of alleles in the original DNA sample at that locus. Allelic bias may be defined to be greater than one, such that if the calculation of the degree of allelic bias returns a value, x, that is less than 1, then the degree of allelic bias may be restated as 1/x. Allelic bias may be due to amplification bias, purification bias, or some other phenomenon that affects different alleles differently.

Primer, also "PCR probe" refers to a single DNA molecule (a DNA oligomer) or a collection of DNA molecules (DNA oligomers) where the DNA molecules are identical, or nearly so, and where the primer contains a region that is designed to hybridize to a targeted polymorphic locus, and may contain a priming sequence designed to allow PCR amplification. A primer may also contain a molecular barcode. A primer may contain a random region that differs for each individual molecule.

Hybrid Capture Probe refers to any nucleic acid sequence, possibly modified, that is generated by various methods such as PCR or direct synthesis and intended to be complementary to one strand of a specific target DNA sequence in a sample. The exogenous hybrid capture probes may be added to a prepared sample and hybridized through a deanture-reannealing process to form duplexes of exogenous-endogenous fragments. These duplexes may then be physically separated from the sample by various means.

Sequence Read refers to data representing a sequence of nucleotide bases that were measured using a clonal sequencing method. Clonal sequencing may produce sequence data representing single, or clones, or clusters of one original DNA molecule. A sequence read may also have associated quality score at each base position of the sequence indicating the probability that nucleotide has been called correctly.

Mapping a sequence read is the process of determining a sequence read's location of origin in the genome sequence of a particular organism. The location of origin of sequence reads is based on similarity of nucleotide sequence of the read and the genome sequence.

Homozygous refers to having similar alleles at corresponding chromosomal loci.

Heterozygous refers to having dissimilar alleles at corresponding chromosomal loci.

Heterozygosity Rate refers to the rate of individuals in the population having heterozygous alleles at a given locus. The heterozygosity rate may also refer to the expected or measured ratio of alleles, at a given locus in an individual, or a sample of DNA.

Haplotype refers to a combination of alleles at multiple loci that are typically inherited together on the same chromosome. Haplotype may refer to as few as two loci or to an entire chromosome depending on the number of recombination events that have occurred between a given set of loci. Haplotype can also refer to a set of single nucleotide polymorphisms (SNPs) on a single chromatid that are statistically associated.

Haplotypic Data, also "Phased Data" or "Ordered Genetic Data," refers to data from a single chromosome in a diploid or polyploid genome, i.e., either the segregated maternal or paternal copy of a chromosome in a diploid genome.

Phasing refers to the act of determining the haplotypic genetic data of an individual given unordered, diploid (or polyploid) genetic data. It may refer to the act of determining which of two genes at an allele, for a set of alleles found on one chromosome, are associated with each of the two homologous chromosomes in an individual.

Phased Data refers to genetic data where one or more haplotypes have been determined.

Fetal refers to "of the fetus," or "of the region of the placenta that is genetically similar to the fetus". In a pregnant woman, some portion of the placenta is genetically similar to the fetus, and the free floating fetal DNA found in maternal blood may have originated from the portion of the placenta with a genotype that matches the fetus.

DNA of Fetal Origin refers to DNA that was originally part of a cell whose genotype was essentially equivalent to that of the fetus. Note that the genetic information in half of the chromosomes in a fetus is inherited from the mother of the fetus; in some embodiments, the DNA from these maternally inherited chromosomes that came from a fetal cell is considered to be "of fetal origin," and not "of maternal origin."

DNA of Maternal Origin refers to DNA that was originally part of a cell whose genotype was essentially equivalent to that of the mother.

Child may refer to an embryo, a blastomere, or a fetus. Note that in the presently disclosed embodiments, the concepts described apply equally well to individuals who are a born child, a fetus, an embryo or a set of cells therefrom. The use of the term child may simply be meant to connote that the individual referred to as the child is the genetic offspring of the parents.

Parent refers to the genetic mother or father of an individual. An individual typically has two parents, a mother and a father, though this may not necessarily be the case such as in genetic or chromosomal chimerism.

Mother may refer to the biological mother of an individual, and/or it may refer to the women who is carrying the individual as he/she gestates.

Parental Context refers to the genetic state of a given SNP, on each of the two relevant chromosomes for one or both of the two parents of the target.

Maternal Plasma refers to the plasma portion of the blood from a female who is pregnant.

Clinical Decision refers to any decision to take or not take an action that has an outcome that affects the health or survival of an individual. In the context of prenatal paternity testing, a clinical decision may refer to a decision to abort or not abort a fetus. A clinical decision may also refer to a decision to conduct further testing, or to take actions to prepare for the birth of a child.

Diagnostic Box refers to one or a combination of machines designed to perform one or a plurality of aspects of the methods disclosed herein. In an embodiment, the diagnostic box may be placed at a point of patient care. In an embodiment, the diagnostic box may perform targeted amplification followed by sequencing. In an embodiment the diagnostic box may function alone or with the help of a technician.

Informatics Based Method or 'informatics based approach' refers to a method that relies heavily on statistics to make sense of a large amount of data. In the context of prenatal diagnosis, it refers to a method designed to determine the ploidy state at one or more chromosomes or the allelic state at one or more alleles by statistically inferring the most likely state, rather than by directly physically measuring the state, given a large amount of genetic data, for example from a molecular array or sequencing. In an embodiment of the present disclosure, the informatics based technique may be one disclosed in this patent. In an embodiment of the present disclosure it may be PARENTAL SUPPORT™

Preferential Enrichment of DNA that corresponds to one or a plurality of loci, or preferential enrichment of DNA at one or a plurality of loci, refers to any method that results in the percentage of molecules of DNA in a post-enrichment DNA mixture that correspond to the loci being higher than the percentage of molecules of DNA in the pre-enrichment DNA mixture that correspond to the loci. The method may involve selective amplification of DNA molecules that correspond to the loci. The method may involve removing DNA molecules that do not correspond to the loci.

Amplification refers to a method that increases the number of copies of a molecule of DNA.

Selective Amplification may refer to a method that increases the number of copies of a particular molecule of DNA, or molecules of DNA that correspond to a particular region of DNA. It may also refer to a method that increases the number of copies of a particular targeted molecule of DNA, or targeted region of DNA more than it increases non-targeted molecules or regions of DNA. Selective amplification may be a method of preferential enrichment.

Universal Priming Sequence refers to a DNA sequence that may be appended to a population of target DNA molecules, for example by ligation, PCR, or ligation mediated PCR. Once added to the population of target molecules, primers specific to the universal priming sequences can be used to amplify the target population using a single pair of amplification primers. Universal priming sequences are typically not related to the target sequences.

Universal Adapters, or 'ligation adaptors' or 'library tags' are DNA molecules containing a universal priming sequence that can be covalently linked to the 5-prime and 3-prime end of a population of target double stranded DNA molecules. The addition of the adapters provides universal priming sequences to the 5-prime and 3-prime end of the target population from which PCR amplification can take place, amplifying all molecules from the target population, using a single pair of amplification primers.

Targeting refers to a method used to selectively amplify or otherwise preferentially enrich those molecules of DNA that correspond to a set of loci, in a mixture of DNA.

Hypothesis refers to the possibility that the alleged father is the biological father of the fetus, or that the alleged father is not the biological father of the fetus.

Determining, establishing, and calculating may be used interchangeably.

Parental Contexts

The parental context refers to the genetic state of a given allele, on each of the two relevant chromosomes for one or both of the two parents of the target. Note that in an embodiment, the parental context does not refer to the allelic state of the target, rather, it refers to the allelic state of the parents. The parental context for a given SNP may consist of four base pairs, two paternal and two maternal; they may be the same or different from one another. It is typically written as "$m_1m_2|f_1f_2$," where $m_1$ and $m_2$ are the genetic state of the given SNP on the two maternal chromosomes, and $f_1$ and $f_2$ are the genetic state of the given SNP on the two paternal chromosomes. In some embodiments, the parental context may be written as "$f_1f_2|m_1m_2$." Note that subscripts "1" and "2" refer to the genotype, at the given allele, of the first and second chromosome; also note that the choice of which chromosome is labeled "1" and which is labeled "2" may be arbitrary.

Note that in this disclosure, A and B are often used to generically represent base pair identities; A or B could equally well represent C (cytosine), G (guanine), A (adenine) or T (thymine). For example, if, at a given SNP based allele, the mother's genotype was T at that SNP on one chromosome, and G at that SNP on the homologous chromosome, and the father's genotype at that allele is G at that SNP on both of the homologous chromosomes, one may say that the target individual's allele has the parental context of AB|BB; it could also be said that the allele has the parental context of AB|AA. Note that, in theory, any of the four possible nucleotides could occur at a given allele, and thus it is possible, for example, for the mother to have a genotype of AT, and the father to have a genotype of GC at a given allele. However, empirical data indicate that in most cases only two of the four possible base pairs are observed at a given allele. It is possible, for example when using single tandem repeats, to have more than two parental, more than four and even more than ten contexts. In this disclosure the discussion assumes that only two possible base pairs will be observed at a given allele, although the embodiments disclosed herein could be modified to take into account the cases where this assumption does not hold.

A "parental context" may refer to a set or subset of target SNPs that have the same parental context. For example, if one were to measure 1000 alleles on a given chromosome on a target individual, then the context AA|BB could refer to the set of all alleles in the group of 1,000 alleles where the genotype of the mother of the target was homozygous, and the genotype of the father of the target is homozygous, but where the maternal genotype and the paternal genotype are dissimilar at that locus. If the parental data is not phased, and thus AB=BA, then there are nine possible parental contexts: AA|AA, AA|AB, AA|BB, AB|AA, AB|AB, AB|BB, BB|AA, BB|AB, and BB|BB. If the parental data is phased, and thus AB BA, then there are sixteen different possible parental contexts: AA|AA, AA|AB, AA|BA, AA|BB, AB|AA, AB|AB, AB|BA, AB|BB, BA|AA, BA|AB, BA|BA, BA|BB, BB|AA, BB|AB, BB|BA, and BB|BB. Every SNP allele on a chromosome, excluding some SNPs on the sex chromosomes, has one of these parental contexts. The set of SNPs wherein the parental context for one parent is heterozygous may be referred to as the heterozygous context.

Different Implementations of the Presently Disclosed Embodiments

Method are disclosed herein for determining the paternity of a target individual. The target individual may be a blastomere, an embryo, or a fetus. In some embodiments of the present disclosure, a method for determining the paternity of an individual may include any of the steps described in this document, and combinations thereof:

In some embodiments the source of the genetic material to be used in determining the paternity of the fetus may be fetal cells, such as nucleated fetal red blood cells, isolated from the maternal blood. The method may involve obtaining a blood sample from the pregnant mother. In some embodiments of the present disclosure, the genetic material to be used in determining the paternity of the fetus may free floating DNA from maternal plasma, where the free floating DNA may be comprised of a mixture of fetal and maternal DNA.

In some embodiments, the source of the genetic material of the fetus may be fetal cells, such as nucleated fetal red blood cells, isolated from the maternal blood. The method may involve obtaining a blood sample from the pregnant mother. The method may involve isolating a fetal red blood cell using visual techniques, based on the idea that a certain combination of colors are uniquely associated with nucleated red blood cell, and a similar combination of colors is not associated with any other present cell in the maternal blood. The combination of colors associated with the nucleated red blood cells may include the red color of the hemoglobin around the nucleus, which color may be made more distinct by staining, and the color of the nuclear material which can be stained, for example, blue. By isolating the cells from maternal blood and spreading them over a slide, and then identifying those points at which one sees both red (from the Hemoglobin) and blue (from the nuclear material) one may be able to identify the location of nucleated red blood cells. One may then extract those nucleated red blood cells using a micromanipulator, use genotyping and/or sequencing techniques to measure aspects of the genotype of the genetic material in those cells.

In one embodiment, one may stain the nucleated red blood cell with a die that only fluoresces in the presence of fetal hemoglobin and not maternal hemoglobin, and so remove the ambiguity between whether a nucleated red blood cell is derived from the mother or the fetus. Some embodiments of the present disclosure may involve staining or otherwise marking nuclear material. Some embodiments of the present disclosure may involve specifically marking fetal nuclear material using fetal cell specific antibodies.

There are many other ways to isolate fetal cells from maternal blood, or fetal DNA from maternal blood, or to enrich samples of fetal genetic material in the presence of maternal genetic material. Some of these methods are listed here, but this is not intended to be an exhaustive list. Some appropriate techniques are listed here for convenience: using fluorescently or otherwise tagged antibodies, size exclusion chromatography, magnetically or otherwise labeled affinity tags, epigenetic differences, such as differential methylation between the maternal and fetal cells at specific alleles, density gradient centrifugation succeeded by CD45/14 depletion and CD71-positive selection from CD45/14 negative-cells, single or double Percoll gradients with different osmolalities, or galactose specific lectin method.

In some embodiments, the genetic sample may be prepared, isolated and/or purified. In some embodiments, the sample may be centrifuged to separate various layers. In some embodiments the preparation of the DNA may involve amplification, separation, purification by chromatography, purification by electrophoresis, filtration, liquid separation, isolation, precipitation, preferential enrichment, preferential amplification, targeted amplification, or any of a number of other techniques either known in the art or described herein.

In some embodiments, the method of the present disclosure may involve amplifying DNA. Amplification of the DNA, a process which transforms a small amount of genetic material to a larger amount of genetic material that comprises a similar set of genetic data, can be done by a wide variety of methods, including, but not limited to polymerase chain reaction (PCR). One method of amplifying DNA is whole genome amplification (WGA). There are a number of methods available for WGA: ligation-mediated PCR (LM-PCR), degenerate oligonucleotide primer PCR (DOP-PCR), and multiple displacement amplification (MDA). In LM-PCR, short DNA sequences called adapters are ligated to blunt ends of DNA. These adapters contain universal amplification sequences, which are used to amplify the DNA by PCR. In DOP-PCR, random primers that also contain universal amplification sequences are used in a first round of annealing and PCR. Then, a second round of PCR is used to amplify the sequences further with the universal primer sequences. MDA uses the phi-29 polymerase, which is a highly processive and non-specific enzyme that replicates DNA and has been used for single-cell analysis. Single-cell whole genome amplification has been used successfully for a variety of applications for a number of years. There are other methods of amplifying DNA from a sample of DNA. The DNA amplification transforms the initial sample of DNA into a sample of DNA that is similar in the set of sequences, but of much greater quantities. In some cases, amplification may not be required.

In some embodiments, DNA may be amplified using a universal amplification, such as WGA or MDA. In some embodiments, DNA may be amplified by targeted amplification, for example using targeted PCR, or circularizing probes. In some embodiments, the DNA may be preferentially enriched using a targeted amplification method, or a method that results in the full or partial separation of desired from undesired DNA, such as capture by hybridization approaches. In some embodiments, DNA may be amplified by using a combination of a universal amplification method and a preferential enrichment method. A fuller description of some of these methods can be found elsewhere in this document.

The genetic data of the target individual and/or of the related individual can be transformed from a molecular state to an electronic state by measuring the appropriate genetic material using tools and or techniques taken from a group including, but not limited to: genotyping microarrays, and high throughput sequencing. Some high throughput sequencing methods include Sanger DNA sequencing, pyrosequencing, the ILLUMINA SOLEXA platform, ILLUMINA's GENOME ANALYZER, or APPLIED BIOSYSTEM's 454 sequencing platform, HELICOS's TRUE SINGLE MOLECULE SEQUENCING platform, HALCYON MOLECULAR's electron microscope sequencing method, or any other sequencing method. All of these methods physically transform the genetic data stored in a sample of DNA into a set of genetic data that is typically stored in a memory device en route to being processed.

A relevant individual's genetic data may be measured by analyzing substances taken from a group including, but not limited to: the individual's bulk diploid tissue, one or more diploid cells from the individual, one or more haploid cells from the individual, one or more blastomeres from the target individual, extra-cellular genetic material found on the individual, extra-cellular genetic material from the individual found in maternal blood, cells from the individual found in maternal blood, one or more embryos created from a gamete from the related individual, one or more blastomeres taken from such an embryo, extra-cellular genetic material found on the related individual, genetic material known to have originated from the related individual, and combinations thereof.

In some embodiments, the likelihood that an alleged father is the biological father of a fetus may be calculated. In some embodiments, the paternity determination may be used to make a clinical decision. This knowledge, typically stored as a physical arrangement of matter in a memory device, may then be transformed into a report. The report may then be acted upon. For example, the clinical decision may be to terminate the pregnancy; alternately, the clinical decision may be to continue the pregnancy.

In an embodiment of the present disclosure, any of the methods described herein may be modified to allow for multiple targets to come from same target individual, for example, multiple blood draws from the same pregnant mother. This may improve the accuracy of the model, as multiple genetic measurements may provide more data with which the target genotype may be determined. In an embodiment, one set of target genetic data served as the primary data which was reported, and the other served as data to double-check the primary target genetic data. In an embodiment, a plurality of sets of genetic data, each measured from genetic material taken from the target individual, are considered in parallel, and thus both sets of target genetic data serve to help determine the paternity of the fetus.

In an embodiment, the method may be used for the purpose of paternity testing. For example, given the SNP-based genotypic information from the mother, and from a man who may or may not be the genetic father, and the measured genotypic information from the mixed sample, it is possible to determine if the genotypic information of the male indeed represents that actual genetic father of the gestating fetus. A simple way to do this is to simply look at the contexts where the mother is AA, and the possible father is AB or BB. In these cases, one may expect to see the father contribution half (AA|AB) or all (AA|BB) of the time, respectively. Taking into account the expected ADO, it is straightforward to determine whether or not the fetal SNPs that are observed are correlated with those of the possible father. Other methods for making a paternity determination are described elsewhere in this document.

In an embodiment of the present disclosure, a pregnant mother would like to determine if a man is the biological father of her fetus. She goes to her doctor, and gives a sample of her blood, and she and her husband gives samples of their own DNA from cheek swabs. A laboratory researcher genotypes the parental DNA using the MDA protocol to amplify the parental DNA, and ILLUMINA INFINIUM arrays to measure the genetic data of the parents at a large number of SNPs. The researcher then spins down the blood, takes the plasma, and isolates a sample of free-floating DNA using size exclusion chromatography. Alternately, the researcher uses one or more fluorescent antibodies, such as one that is specific to fetal hemoglobin to isolate a nucleated fetal red blood cell. The researcher then takes the isolated or enriched fetal genetic material and amplifies it using a library of 70-mer oligonucleotides appropriately designed such that two ends of each oligonucleotide corresponded to the flanking sequences on either side of a target allele. Upon addition of a polymerase, ligase, and the appropriate reagents, the oligonucleotides underwent gap-filling circularization, capturing the desired allele. An exonuclease was added, heat-inactivated, and the products were used directly as a template for PCR amplification. The PCR products were sequenced on an ILLUMINA GENOME ANALYZER. The sequence reads were used as input for the PARENTAL SUPPORT™ method, which then predicted the ploidy state of the fetus. The method determines that the alleged father is not the biological father of the fetus, and calculates a confidence on the determination of 99.98%. A report is generated disclosing both the paternity determination and the confidence of the determination.

In another embodiment a woman who is pregnant wants to know if a man is the biological father of her fetus. The obstetrician takes a blood draw from the mother and father. The blood is sent to a laboratory, where a technician centrifuges the maternal sample to isolate the plasma and the buffy coat. The DNA in the buffy coat and the paternal blood sample are transformed through amplification and the genetic data encoded in the amplified genetic material is further transformed from molecularly stored genetic data into electronically stored genetic data by running the genetic material on a high throughput sequencer to measure the parental genotypes. The plasma sample is preferentially enriched at a set of loci using a 5,000-plex hemi-nested targeted PCR method. The mixture of DNA fragments is prepared into a DNA library suitable for sequencing. The DNA is then sequenced using a high throughput sequencing method, for example, the ILLUMINA GAIIx GENOME ANALYZER. The sequencing transforms the information that is encoded molecularly in the DNA into information that is encoded electronically in computer hardware. An informatics based technique that includes the presently disclosed embodiments, such as PARENTAL SUPPORT™, may be used to determine the paternity of the fetus. This may involve calculating, on a computer, allele counts at the plurality of polymorphic loci from the DNA measurements made on the enriched sample; and determining the likelihood that the man is the biological father of her fetus. The probability that the alleged father is the biological father of the fetus is determined to be 99.9999%, and the confidence of the paternity determination is calculated to be 99.99%. A report is printed out, or sent electronically to the pregnant woman's obstetrician, who transmits the determination to the woman. The woman, her husband, and the doctor sit down and discuss the report.

In an embodiment, the raw genetic material of the mother and the father is transformed by way of amplification to an amount of DNA that is similar in sequence, but larger in quantity. Then, by way of a genotyping method, the genotypic data that is encoded by nucleic acids is transformed into genetic measurements that may be stored physically and/or electronically on a memory device, such as those described above. The relevant algorithms that makeup the PARENTAL SUPPORT™ algorithm, relevant parts of which are discussed in detail herein, are translated into a computer program, using a programming language. Then, through the execution of the computer program on the computer hardware, instead of being physically encoded bits and bytes, arranged in a pattern that represents raw measurement data, they become transformed into a pattern that represents a high confidence determination of the paternity of the fetus. The details of this transformation will rely on the data itself and the computer language and hardware system used to execute the method described herein. Then, the data that is physically configured to represent a high quality paternity determination of the fetus is transformed into a report which may be sent to a health care practitioner. This transformation may be carried out using a printer or a computer display. The report may be a printed copy, on paper or other suitable medium, or else it may be electronic. In the case of an electronic report, it may be transmitted, it may be physically stored on a memory device at a location on the computer accessible by the health care practitioner; it also may be displayed on a screen so that it may be read. In the case of a screen display, the data may be transformed to a readable format by causing the physical transformation of pixels on the display device. The transformation may be accomplished by way of physically firing electrons at a phosphorescent screen, by way of altering an electric charge that physically changes the transparency of a specific set of pixels on a screen that may lie in front of a substrate that emits or absorbs photons. This transformation may be accomplished by way of changing the nanoscale orientation of the molecules in a liquid crystal, for example, from nematic to cholesteric or smectic phase, at a specific set of pixels. This transformation may be accomplished by way of an electric current causing photons to be emitted from a specific set of pixels made from a plurality of light emitting diodes arranged in a meaningful pattern. This transformation may be accomplished by any other way used to display information, such as a computer screen, or some other output device or way of transmitting information. The health care practitioner may then act on the report, such that the data in the report is transformed into an action. The action may be to continue or discontinue the pregnancy, in which case a gestating fetus is transformed into non-living fetus. Alternately, one may transform a set of genotypic measurements into a report that helps a physician treat his pregnant patient.

In some embodiments, the methods described herein can be used at a very early gestational age, for example as early as four week, as early as five weeks, as early as six weeks, as early as seven weeks, as early as eight weeks, as early as nine weeks, as early as ten weeks, as early as eleven weeks, and as early as twelve weeks.

Any of the embodiments disclosed herein may be implemented in digital electronic circuitry, integrated circuitry, specially designed ASICs (application-specific integrated circuits), computer hardware, firmware, software, or in combinations thereof. Apparatus of the presently disclosed embodiments can be implemented in a computer program product tangibly embodied in a machine-readable storage device for execution by a programmable processor; and method steps of the presently disclosed embodiments can be performed by a programmable processor executing a program of instructions to perform functions of the presently disclosed embodiments by operating on input data and generating output. The presently disclosed embodiments can be implemented advantageously in one or more computer programs that are executable and/or interpretable on a programmable system including at least one programmable processor, which may be special or general purpose, coupled to receive data and instructions from, and to transmit data and instructions to, a storage system, at least one input device, and at least one output device. Each computer program can be implemented in a high-level procedural or object-oriented programming language or in assembly or machine language if desired; and in any case, the language can be a compiled or interpreted language. A computer program may be deployed in any form, including as a stand-alone program, or as a module, component, subroutine, or other unit suitable for use in a computing environment. A computer program may be deployed to be executed or interpreted on one computer or on multiple computers at one site, or distributed across multiple sites and interconnected by a communication network.

Computer readable storage media, as used herein, refers to physical or tangible storage (as opposed to signals) and includes without limitation volatile and non-volatile, removable and non-removable media implemented in any method or technology for the tangible storage of information such as computer-readable instructions, data structures, program modules or other data. Computer readable storage media includes, but is not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other physical or material medium which can be used to tangibly store the desired information or data or instructions and which can be accessed by a computer or processor.

Targeted Enrichment and Sequencing

The use of a technique to enrich a sample of DNA at a set of target loci followed by sequencing as part of a method for non-invasive prenatal allele calling or ploidy calling may confer a number of unexpected advantages. In some embodiments of the present disclosure, the method involves measuring genetic data for use with an informatics based method, such as PARENTAL SUPPORT™ (PS). The ultimate outcome of some of the embodiments is the actionable genetic data of an embryo or a fetus. There are many methods that may be used to measure the genetic data of the individual and/or the related individuals as part of embodied methods. In an embodiment, a method for enriching the concentration of a set of targeted alleles is disclosed herein, the method comprising one or more of the following steps: targeted amplification of genetic material, addition of loci specific oligonucleotide probes, ligation of specified DNA strands, isolation of sets of desired DNA, removal of unwanted components of a reaction, detection of certain sequences of DNA by hybridization, and detection of the sequence of one or a plurality of strands of DNA by DNA sequencing methods. In some cases the DNA strands may refer to target genetic material, in some cases they may refer to primers, in some cases they may refer to synthesized sequences, or combinations thereof. These steps may be carried out in a number of different orders. Given the highly variable nature of molecular biology, it is generally not obvious which methods, and which combinations of steps, will perform poorly, well, or best in various situations.

For example, a universal amplification step of the DNA prior to targeted amplification may confer several advantages, such as removing the risk of bottlenecking and reducing allelic bias. The DNA may be mixed an oligonucleotide probe that can hybridize with two neighboring regions of the target sequence, one on either side. After hybridization, the ends of the probe may be connected by adding a polymerase, a means for ligation, and any necessary reagents to allow the circularization of the probe. After circularization, an exonuclease may be added to digest to non-circularized genetic material, followed by detection of the circularized probe. The DNA may be mixed with PCR primers that can hybridize with two neighboring regions of the target sequence, one on either side. After hybridization, the ends of the probe may be connected by adding a polymerase, a means for ligation, and any necessary reagents to complete PCR amplification. Amplified or unamplified DNA may be targeted by hybrid capture probes that target a set of loci; after hybridization, the probe may be localized and separated from the mixture to provide a mixture of DNA that is enriched in target sequences.

In some embodiments the detection of the target genetic material may be done in a multiplexed fashion. The number of genetic target sequences that may be run in parallel can range from one to ten, ten to one hundred, one hundred to one thousand, one thousand to ten thousand, ten thousand to one hundred thousand, one hundred thousand to one million, or one million to ten million. Note that the prior art includes disclosures of successful multiplexed PCR reactions involving pools of up to about 50 or 100 primers, and not more. Prior attempts to multiplex more than 100 primers per pool have resulted in significant problems with unwanted side reactions such as primer-dimer formation.

In some embodiments, this method may be used to genotype a single cell, a small number of cells, two to five cells, six to ten cells, ten to twenty cells, twenty to fifty cell, fifty to one hundred cells, one hundred to one thousand cells, or a small amount of extracellular DNA, for example from one to ten picograms, from ten to one hundred picograms, from one hundred picograms to one nanogram, from one to ten nanograms, from ten to one hundred nanograms, or from one hundred nanograms to one microgram.

The use of a method to target certain loci followed by sequencing as part of a method for allele calling or ploidy calling may confer a number of unexpected advantages. Some methods by which DNA may be targeted, or preferentially enriched, include using circularizing probes, linked inverted probes (LIPs, MIPs), capture by hybridization methods such as SURESELECT, and targeted PCR or ligation-mediated PCR amplification strategies.

In some embodiments, a method of the present disclosure involves measuring genetic data for use with an informatics based method, such as PARENTAL SUPPORT™ (PS). PARENTAL SUPPORT™ is an informatics based approach to manipulating genetic data, aspects of which are described herein. The ultimate outcome of some of the embodiments is the actionable genetic data of an embryo or a fetus followed by a clinical decision based on the actionable data. The algorithms behind the PS method take the measured genetic data of the target individual, often an embryo or fetus, and the measured genetic data from related individuals, and are able to increase the accuracy with which the genetic state of the target individual is known. In an embodiment, the measured genetic data is used in the context of making paternity determinations during prenatal genetic diagnosis. There are many methods that may be used to measure the genetic data of the individual and/or the related individuals in the aforementioned contexts. The different methods comprise a number of steps, those steps often involving amplification of genetic material, addition of olgionucleotide probes, ligation of specified DNA strands, isolation of sets of desired DNA, removal of unwanted components of a reaction, detection of certain sequences of DNA by hybridization, detection of the sequence of one or a plurality of strands of DNA by DNA sequencing methods. In some cases the DNA strands may refer to target genetic material, in some cases they may refer to primers, in some cases they may refer to synthesized sequences, or combinations thereof. These steps may be carried out in a number of different orders. Given the highly variable nature of molecular biology, it is generally not obvious which methods, and which combinations of steps, will perform poorly, well, or best in various situations.

Some embodiments of the present disclosure involve the use of "Linked Inverted Probes" (LIPs), which have been previously described in the literature. LIPs is a generic term meant to encompass technologies that involve the creation of a circular molecule of DNA, where the probes are designed to hybridize to targeted region of DNA on either side of a targeted allele, such that addition of appropriate polymerases and/or ligases, and the appropriate conditions, buffers and other reagents, will complete the complementary, inverted region of DNA across the targeted allele to create a circular loop of DNA that captures the information found in the targeted allele. LIPs may also be called pre-circularized probes, pre-circularizing probes, or circularizing probes. The LIPs probe may be a linear DNA molecule between 50 and 500 nucleotides in length, and in an embodiment between 70 and 100 nucleotides in length; in some embodiments, it may be longer or shorter than described herein. Others embodiments of the present disclosure involve different incarnations, of the LIPs technology, such as Padlock Probes and Molecular Inversion Probes (MIPs).

One method to target specific locations for sequencing is to synthesize probes in which the 3' and 5' ends of the probes anneal to target DNA at locations adjacent to and on either side of the targeted region, in an inverted manner, such that the addition of DNA polymerase and DNA ligase results in extension from the 3' end, adding bases to single stranded probe that are complementary to the target molecule (gap-fill), followed by ligation of the new 3' end to the 5' end of the original probe resulting in a circular DNA molecule that can be subsequently isolated from background DNA. The probe ends are designed to flank the targeted region of interest. One aspect of this approach is commonly called MIPS and has been used in conjunction with array technologies to determine the nature of the sequence filled in.

Ligation-mediated PCR is method of PCR used to preferentially enrich a sample of DNA by amplifying one or a plurality of loci in a mixture of DNA, the method comprising: obtaining a set of primer pairs, where each primer in the pair contains a target specific sequence and a non-target sequence, where the target specific sequence is designed to anneal to a target region, one upstream and one downstream from the polymorphic site; polymerization of the DNA from the 3-prime end of upstream primer to the fill the single strand region between it and the 5-prime end of the downstream primer with nucleotides complementary to the target molecule; ligation of the last polymerized base of the upstream primer to the adjacent 5-prime base of the downstream primer; and amplification of only polymerized and ligated molecules using the non-target sequences contained at the 5-prime end of the upstream primer and the 3-prime end of the downstream primer. Pairs of primers to distinct targets may be mixed in the same reaction. The non-target sequences serve as universal sequences such that all pairs of primers that have been successfully polymerized and ligated may be amplified with a single pair of amplification primers.

In an embodiment, a sample of DNA may be preferentially enriched using a capture by hybridization approach. Some examples of commercial capture by hybridization technologies include AGILENT's SURESELECT and ILLUMINA's TRUSEQ. In capture by hybridization, a set of oligonucleotides that is complimentary or mostly complimentary to the desired targeted sequences is allowed to hybridize to a mixture of DNA, and then physically separated from the mixture. Once the desired sequences have hybridized to the targeting oligonucleotides, the effect of physically removing the targeting oligonucleotides is to also remove the targeted sequences. Once the hybridized oligos are removed, they can be heated to above their melting temperature and they can be amplified. Some ways to physically remove the targeting oligonucleotides is by covalently bonding the targeting oligos to a solid support, for example a magnetic bead, or a chip. Another way to physically remove the targeting oligonucleotides is by covalently bonding them to a molecular moiety with a strong affinity for another molecular moiety. An example of such a molecular pair is biotin and streptavidin, such as is used in SURESELECT. Thus that targeted sequences could be covalently attached to a biotin molecule, and after hybridization, a solid support with streptavidin affixed can be used to pull down the biotinylated oligonucleotides, to which are hybridized to the targeted sequences.

In some embodiments, PCR can be used to target specific locations of the genome. In plasma samples, the original DNA is highly fragmented (typically less than 500 bp, with an average length less than 200 bp). In PCR, both forward and reverse primers must anneal to the same fragment to enable amplification. Therefore, if the fragments are short, the PCR assays must amplify relatively short regions as well. PCR assay can be generated in large numbers, however, the interactions between different PCR assays makes it difficult to multiplex them beyond about one hundred assays. Various complex molecular approaches can be used to increase the level of multiplexing, but it may still be limited to fewer than 100, perhaps 200, or possibly 500 assays per reaction. Samples with large quantities of DNA can be split among multiple sub-reactions and then recombined before sequencing. For samples where either the overall sample or some subpopulation of DNA molecules is limited, splitting the sample would introduce statistical noise. In an embodiment, a small or limited quantity of DNA may refer to an amount below 10 pg, between 10 and 100 pg, between 100 pg and 1 ng, between 1 and 10 ng, or between 10 and 100 ng. Note that while this method is particularly useful on small amounts of DNA where other methods that involve splitting into multiple pools can cause significant problems related to introduced stochastic noise, this method still provides the benefit of minimizing bias when it is run on samples of any quantity of DNA. In these situations a universal pre-amplification step may be used to increase the overall sample quantity. Ideally, this pre-amplification step should not appreciably alter the allelic distributions.

In general, to perform targeted sequencing of multiple (n) targets of a sample (greater than 50, greater than 100, greater than 500, or greater than 1,000), one can split the sample into a number of parallel reactions that amplify one or a smaller number of individual targets. This has been performed in PCR multiwell plates or can be done in commercial platforms such as the FLUIDIGM ACCESS ARRAY (48 reactions per sample in microfluidic chips) or DROPLET PCR by RAIN DANCE TECHNOLOGY (100s to a few thousands of targets). Unfortunately, these split-and-pool methods are problematic for samples with a limited amount of DNA, as there is often not enough copies of the genome to ensure that there is one copy of each region of the genome in each well. This is an especially severe problem when polymorphic loci are targeted, and the relative proportions of the alleles at the polymorphic loci are needed, as the stochastic noise introduced by the splitting and pooling will cause very poorly accurate measurements of the proportions of the alleles that were present in the original sample of DNA. Described here is a method to effectively and efficiently amplify many PCR reactions that is applicable to cases where only a limited amount of DNA is available. In an embodiment, the method may be applied for analysis of single cells, body fluids, mixtures of DNA such as the free floating DNA found in maternal plasma, biopsies, environmental and/or forensic samples.

In an embodiment, the targeted sequencing may involve one, a plurality, or all of the following steps. a) Generate and universally amplify a library with adaptor sequences on both ends of DNA fragments. b) Divide into multiple reactions after library amplification. c) Perform about 100-plex, about 1000-plex, or about 10,000-plex amplification of selected targets using one target specific "Forward" primer per target and one tag specific primer. d) Perform a second amplification from this product using "Reverse" target specific primers and one (or more) primer specific to a universal tag that was introduced as part of the target specific forward primers in the first round. e) Divide the product into multiple aliquots and amplify subpools of targets in individual reactions (for example, 50 to 500-plex, though this can be used all the way down to singleplex. f) Pool products of parallel subpools reactions. During these amplifications primers may carry sequencing compatible tags (partial or full length) such that the products can be sequenced.

In an embodiment, it is possible to mitigate potential losses in subsequent steps by amplifying all or a fraction of the original cell free DNA (cfDNA) sample. Various methods are available to amplify all of the genetic material in a sample, increasing the amount available for downstream procedures. In an embodiment, ligation mediated PCR (LM-PCR) DNA fragments are amplified by PCR after ligation of either one distinct adaptors, two distinct adapters, or many distinct adaptors. In an embodiment, multiple displacement amplification (MDA) phi-29 polymerase is used to amplify all DNA isothermally. In DOP-PCR and variations, random priming is used to amplify the original material DNA. Each method has certain characteristics such as uniformity of amplification across all represented regions of the genome, efficiency of capture and amplification of original DNA, and amplification performance as a function of the length of the fragment.

Traditional PCR assay design results in significant losses of distinct fetal molecules, but losses can be greatly reduced by designing very short PCR assays, termed mini-PCR assays. Fetal cfDNA in maternal serum is highly fragmented and the fragment sizes are distributed in approximately a Gaussian fashion with a mean of about 160 bp, a standard deviation of about 15 bp, a minimum size of about 100 bp, and a maximum size of about 220 bp. The distribution of fragment start and end positions with respect to the targeted polymorphisms, while not necessarily random, vary widely among individual targets and among all targets collectively and the polymorphic site of one particular target locus may occupy any position from the start to the end among the various fragments originating from that locus. Note that the term mini-PCR may equally well refer to normal PCR with no additional restrictions or limitations.

During PCR, amplification will only occur from template DNA fragments comprising both forward and reverse primer sites. Because fetal cfDNA fragments are short, the likelihood of both primer sites being present the likelihood of a fetal fragment of length L comprising both the forward and reverse primers sites is ratio of the length of the amplicon to the length of the fragment. Under ideal conditions, assays in which the amplicon is 45, 50, 55, 60, 65, or 70 bp will successfully amplify from about 72%, 69%, 66%, 63%, 59%, or 56%, respectively, of available template fragment molecules. The amplicon length is the distance between the 5-prime ends of the forward and reverse priming sites. Amplicon length that is shorter than typically used by those known in the art may result in more efficient measurements of the desired polymorphic loci by only requiring short sequence reads. In an embodiment, a substantial fraction of the amplicons should be less than 100 bp, less than 90 bp, less than 80 bp, less than 70 bp, less than 65 bp, less than 60 bp, less than 55 bp, less than 50 bp, or less than 45 bp.

Note that in methods known in the prior art, short assays such as those described herein are usually avoided because they are not required and they impose considerable constraint on primer design by limiting primer length, annealing characteristics, and the distance between the forward and reverse primer.

Multiplex PCR may involve a single round of PCR in which all targets are amplified or it may involve one round of PCR followed by one or more rounds of nested PCR or some variant of nested PCR. Nested PCR consists of a subsequent round or rounds of PCR amplification using one or more new primers that bind internally, by at least one base pair, to the primers used in a previous round. Nested PCR reduces the number of spurious amplification targets by amplifying, in subsequent reactions, only those amplification products from the previous one that have the correct internal sequence. Reducing spurious amplification targets improves the number of useful measurements that can be obtained, especially in sequencing. Nested PCR typically entails designing primers completely internal to the previous primer binding sites, necessarily increasing the minimum DNA segment size required for amplification. For samples such as maternal plasma cfDNA, in which the DNA is highly fragmented, the larger assay size reduces the number of distinct cfDNA molecules from which a measurement can be obtained. In an embodiment, to offset this effect, one may use a partial nesting approach where one or both of the second round primers overlap the first binding sites extending internally some number of bases to achieve additional specificity while minimally increasing in the total assay size.

In an embodiment, a multiplex pool of PCR assays are designed to amplify potentially heterozygous SNP or other polymorphic or non-polymorphic loci on one or more chromosomes and these assays are used in a single reaction to amplify DNA. The number of PCR assays may be between 50 and 200 PCR assays, between 200 and 1,000 PCR assays, between 1,000 and 5,000 PCR assays, or between 5,000 and 20,000 PCR assays (50 to 200-plex, 200 to 1,000-plex, 1,000 to 5,000-plex, 5,000 to 20,000-plex, more than 20,000-plex respectively).

In an embodiment, a 100-plex to-500 plex, 500-plex to 1,000-plex, 1,000-plex to 2,000-plex, 2,000-plex to 5,000-plex, 5,000-plex to 10,000-plex, 10,000-plex to 20,000-plex, 20,000-plex to 50,000-plex, or 50,000-plex to 100,000-plex PCR assay pool is created such that forward and reverse primers have tails corresponding to the required forward and reverse sequences required by a high throughput sequencing instrument such as the HISEQ, GAIIX, or MISEQ available from ILLUMINA. In addition, included 5-prime to the sequencing tails is an additional sequence that can be used as a priming site in a subsequent PCR to add nucleotide barcode sequences to the amplicons, enabling multiplex sequencing of multiple samples in a single lane of the high throughput sequencing instrument. In an embodiment, a 10,000-plex PCR assay pool is created such that reverse primers have tails corresponding to the required reverse sequences required by a high throughput sequencing instrument. After amplification with the first 10,000-plex assay, a subsequent PCR amplification may be performed using a another 10,000-plex pool having partly nested forward primers (e.g. 6-bases nested) for all targets and a reverse primer corresponding to the reverse sequencing tail included in the first round. This subsequent round of partly nested amplification with just one target specific primer and a universal primer limits the required size of the assay, reducing sampling noise, but greatly reduces the number of spurious amplicons. The sequencing tags can be added to appended ligation adaptors and/or as part of PCR probes, such that the tag is part of the final amplicon.

Fetal fraction affects performance of the test; it is more difficult to determine the correct paternity on samples with a lower fetal fraction. There are a number of ways to enrich the fetal fraction of the DNA found in maternal plasma. Fetal fraction can be increased by the previously described LM-PCR method already discussed as well as by a targeted removal of long maternal fragments. In embodiment, the longer fragments are removed using size selection techniques. In an embodiment, prior to multiplex PCR amplification of the target loci, an additional multiplex PCR reaction may be carried out to selectively remove long and largely maternal fragments corresponding to the loci targeted in the subsequent multiplex PCR. Additional primers are designed to anneal a site a greater distance from the polymorphism than is expected to be present among cell free fetal DNA fragments. These primers may be used in a one cycle multiplex PCR reaction prior to multiplex PCR of the target polymorphic loci. These distal primers are tagged with a molecule or moiety that can allow selective recognition of the tagged pieces of DNA. In an embodiment, these molecules of DNA may be covalently modified with a biotin molecule that allows removal of newly formed double stranded DNA comprising these primers after one cycle of PCR. Double stranded DNA formed during that first round is likely maternal in origin. Removal of the hybrid material may be accomplish by the used of magnetic streptavidin beads. There are other methods of tagging that may work equally well. In an embodiment, size selection methods may be used to enrich the sample for shorter strands of DNA; for example those less than about 800 bp, less than about 500 bp, or less than about 300 bp. Amplification of short fragments can then proceed as usual.

In some embodiments, the target DNA may originate from single cells, from samples of DNA consisting of less than one copy of the target genome, from low amounts of DNA, from DNA from mixed origin (e.g. pregnancy plasma: placental and maternal DNA; cancer patient plasma and tumors: mix between healthy and cancer DNA, transplantation etc), from other body fluids, from cell cultures, from culture supernatants, from forensic samples of DNA, from ancient samples of DNA (e.g. insects trapped in amber), from other samples of DNA, and combinations thereof.

In some embodiments, the methods described herein may be used to amplify and/or detect SNPs, single tandem repeats (STRs), copy number, nucleotide methylation, mRNA levels, other types of RNA expression levels, other genetic and/or epigenetic features. The mini-PCR methods described herein may be used along with next-generation sequencing; it may be used with other downstream methods such as microarrays, counting by digital PCR, real-time PCR, Mass-spectrometry analysis etc.

In some embodiment, the mini-PCR amplification methods described herein may be used as part of a method for accurate quantification of minority populations. It may be used for absolute quantification using spike calibrators. It may be used for mutation/minor allele quantification through very deep sequencing, and may be run in a highly multiplexed fashion. It may be used for standard paternity and identity testing of relatives or ancestors, in human, animals, plants or other creatures. It may be used for forensic testing. It may be used for rapid genotyping and copy number analysis (CN), on any kind of material, e.g. amniotic fluid and CVS, sperm, product of conception (POC). It may be used for single cell analysis, such as genotyping on samples biopsied from embryos. It may be used for rapid embryo analysis (within less than one, one, or two days of biopsy) by targeted sequencing using min-PCR.

Highly multiplexed PCR can often result in the production of a very high proportion of product DNA resulting from unproductive side reactions such as primer dimer formation. In an embodiment, the particular primers that are most likely to cause unproductive side reactions may be removed from the primer library to give a primer library that will result in a greater proportion of amplified DNA that maps to the genome. The step of removing problematic primers, that is, those primers that are particularly likely to firm dimers has unexpectedly enabled extremely high PCR multiplexing levels for subsequent analysis by sequencing. In systems such as sequencing, where performance significantly degrades by primer dimers and/or other mischief products, greater than 10, greater than 50, and greater than 100 times higher multiplexing than other described multiplexing has been achieved. Note this is opposed to probe based detection methods, e.g. microarrays, TaqMan, PCR etc. where an excess of primer dimers will not affect the outcome appreciably. Also note that the general belief in the art is that multiplexing PCR for sequencing is limited to about 100 assays in the same well.

There are a number of ways to choose primers for a library where the amount of non-mapping primer-dimer or other primer mischief products are minimized. Empirical data indicate that a small number of 'bad' primers are responsible for a large amount of non-mapping primer dimer side reactions. Removing these 'bad' primers can increase the percent of sequence reads that map to targeted loci. One way to identify the 'bad' primers is to look at the sequencing data of DNA that was amplified by targeted amplification; those primer dimers that are seen with greatest frequency can be removed to give a primer library that is significantly less likely to result in side product DNA that does not map to the genome. There are also publicly available programs that can calculate the binding energy of various primer combinations, and removing those with the highest binding energy will also give a primer library that is significantly less likely to result in side product DNA that does not map to the genome.

Note that there are other methods for determining which PCR probes are likely to form dimers. In an embodiment, analysis of a pool of DNA that has been amplified using a non-optimized set of primers may be sufficient to determine problematic primers. For example, analysis may be done using sequencing, and those dimers which are present in the greatest number are determined to be those most likely to form dimers, and may be removed.

To select target locations, one may start with a pool of alleged primer pair designs and create a thermodynamic model of potentially adverse interactions between primer pairs, and then use the model to eliminate designs that are incompatible with other the designs in the pool.

There are many workflows that are possible when conducting PCR; some workflows typical to the methods disclosed herein are described. The steps outlined herein are not meant to exclude other possible steps nor does it imply that any of the steps described herein are required for the method to work properly. A large number of parameter variations or other modifications are known in the literature, and may be made without affecting the essence of the invention. One particular generalized workflow is given below followed by a number of possible variants. The variants typically refer to possible secondary PCR reactions, for example different types of nesting that may be done (step 3). It is important to note that variants may be done at different times, or in different orders than explicitly described herein.

1. The DNA in the sample may have ligation adapters, often referred to as library tags or ligation adaptor tags (LTs), appended, where the ligation adapters contain a universal priming sequence, followed by a universal amplification. In an embodiment, this may be done using a standard protocol designed to create sequencing libraries after fragmentation. In an embodiment, the DNA sample can be blunt ended, and then an A can be added at the 3' end. A Y-adaptor with a T-overhang can be added and ligated. In some embodiments, other sticky ends can be used other than an A or T overhang. In some embodiments, other adaptors can be added, for example looped ligation adaptors. In some embodiments, the adaptors may have tag designed for PCR amplification.

2. Specific Target Amplification (STA): Pre-amplification of hundreds to thousands to tens of thousands and even hundreds of thousands of targets may be multiplexed in one reaction. STA is typically run from 10 to 30 cycles, though it may be run from 5 to 40 cycles, from 2 to 50 cycles, and even from 1 to 100 cycles. Primers may be tailed, for example for a simpler workflow or to avoid sequencing of a large proportion of dimers. Note that typically, dimers of both primers carrying the same tag will not be amplified or sequenced efficiently. In some embodiments, between 1 and 10 cycles of PCR may be carried out; in some embodiments between 10 and 20 cycles of PCR may be carried out; in some embodiments between 20 and 30 cycles of PCR may be carried out; in some embodiments between 30 and 40 cycles of PCR may be carried out; in some embodiments more than 40 cycles of PCR may be carried out. The amplification may be a linear amplification. The number of PCR cycles may be optimized to result in an optimal depth of read (DOR) profile. Different DOR profiles may be desirable for different purposes. In some embodiments, a more even distribution of reads between all assays is desirable; if the DOR is too small for some assays, the stochastic noise can be too high for the data to be too useful, while if the depth of read is too high, the marginal usefulness of each additional read is relatively small.

Primer tails may improve the detection of fragmented DNA from universally tagged libraries. If the library tag and the primer-tails contain a homologous sequence, hybridization can be improved (for example, melting temperature ($T_M$) is lowered) and primers can be extended if only a portion of the primer target sequence is in the sample DNA fragment. In some embodiments, 13 or more target specific base pairs may be used. In some embodiments, 10 to 12 target specific base pairs may be used. In some embodiments, 8 to 9 target specific base pairs may be used. In some embodiments, 6 to 7 target specific base pairs may be used. In some embodiments, STA may be performed on pre-amplified DNA, e.g. MDA, RCA, other whole genome amplifications, or adaptor-mediated universal PCR. In some embodiments, STA may be performed on samples that are enriched or depleted of certain sequences and populations, e.g. by size selection, target capture, directed degradation.

3. In some embodiments, it is possible to perform secondary multiplex PCRs or primer extension reactions to increase specificity and reduce undesirable products. For example, full nesting, semi-nesting, hemi-nesting, and/or subdividing into parallel reactions of smaller assay pools are all techniques that may be used to increase specificity. Experiments have shown that splitting a sample into three 400-plex reactions resulted in product DNA with greater specificity than one 1,200-plex reaction with exactly the same primers. Similarly, experiments have shown that splitting a sample into four 2,400-plex reactions resulted in product DNA with greater specificity than one 9,600-plex reaction with exactly the same primers. In an embodiment, it is possible to use target-specific and tag specific primers of the same and opposing directionality.

4. In some embodiments, it is possible to amplify a DNA sample (dilution, purified or otherwise) produced by an STA reaction using tag-specific primers and "universal amplification", i.e. to amplify many or all pre-amplified and tagged targets. Primers may contain additional functional sequences, e.g. barcodes, or a full adaptor sequence necessary for sequencing on a high throughput sequencing platform.

These methods may be used for analysis of any sample of DNA, and are especially useful when the sample of DNA is particularly small, or when it is a sample of DNA where the DNA originates from more than one individual, such as in the case of maternal plasma. These methods may be used on DNA samples such as a single or small number of cells, genomic DNA, plasma DNA, amplified plasma libraries, amplified apoptotic supernatant libraries, or other samples of mixed DNA. In an embodiment, these methods may be used in the case where cells of different genetic constitution may be present in a single individual, such as with cancer or transplants.

In some embodiments, the multiplex PCR amplification may involve using various types of nesting protocol, for example: semi-nested mini-PCR, fully nested mini-PCR, heminested mini-PCR, triply hemi-nested mini-PCR, one-sided nested mini-PCR, one-sided mini-PCR or reverse semi-nested mini-PCR.

Diagnostic Box

In an embodiment, the present disclosure comprises a diagnostic box that is capable of partly or completely carrying out aspects of the methods described in this disclosure. In an embodiment, the diagnostic box may be located at a physician's office, a hospital laboratory, or any suitable location reasonably proximal to the point of patient care. The box may be able to run the aspects of the method in a wholly automated fashion, or the box may require one or a number of steps to be completed manually by a technician. In an embodiment, the box may be able to analyze the genotypic data measured on the maternal plasma. In an embodiment, the box may be linked to means to transmit the genotypic data measured using the diagnostic box to an external computation facility which may then analyze the genotypic data, and possibly also generate a report. The diagnostic box may include a robotic unit that is capable of transferring aqueous or liquid samples from one container to another. It may comprise a number of reagents, both solid and liquid. It may comprise a high throughput sequencer. It may comprise a computer.

Primer Kit

In some embodiments, a kit may be formulated that comprises a plurality of primers designed to achieve the methods described in this disclosure. The primers may be outer forward and reverse primers, inner forward and reverse primers as disclosed herein; they could be primers that have been designed to have low binding affinity to other primers in the kit as disclosed in the section on primer design; they could be hybrid capture probes or pre-circularized probes as described in the relevant sections, or some combination thereof. In an embodiment, a kit may be formulated for determining a ploidy status of a target chromosome in a gestating fetus designed to be used with the methods disclosed herein, the kit comprising a plurality of inner forward primers and optionally the plurality of inner reverse primers, and optionally outer forward primers and outer reverse primers, where each of the primers is designed to hybridize to the region of DNA immediately upstream and/or downstream from one of the polymorphic sites on the target chromosome, and optionally additional chromosomes. In an embodiment, the primer kit may be used in combination with the diagnostic box described elsewhere in this document.

Maximum Likelihood Estimates

Many methods known in the art for detecting the presence or absence of a phenotype or genotype, for example, a chromosomal abnormality, a medical condition or a paternity relationship involve the use of a single hypothesis rejection test, where a metric that is directly related to or correlated with the condition is measured, and if the metric is on one side of a given threshold, the condition is determined to be present, while if the metric falls on the other side of the threshold, the condition is determined to be absent. A single-hypothesis rejection test only looks at the null distribution when deciding between the null and alternate hypotheses. Without taking into account the alternate distribution, one cannot estimate the likelihood of each hypothesis given the observed data and therefore cannot calculate a confidence on the call. Hence with a single-hypothesis rejection test, one gets a yes or no answer without an estimate of the confidence associated with the specific case.

In some embodiments, the method disclosed herein is able to detect the presence or absence of phenotype or genotype, for example, a chromosomal abnormality, a medical condition or a paternity relationship, using a maximum likelihood method. This is a substantial improvement over a method using a single hypothesis rejection technique as the threshold for calling absence or presence of the condition can be adjusted as appropriate for each case. This is particularly relevant for diagnostic techniques that aim to determine the paternity of a gestating fetus from genetic data available from the mixture of fetal and maternal DNA present in the free floating DNA found in maternal plasma. The maximum likelihood estimation method may use the allelic distributions associated with each hypothesis to estimate the likelihood of the data conditioned on each hypothesis. These conditional probabilities can then be converted to a hypothesis call and confidence. Similarly, maximum a posteriori estimation method uses the same conditional probabilities as the maximum likelihood estimate, but also incorporates population priors when choosing the best hypothesis and determining confidence.

Therefore, the use of a maximum likelihood estimate (MLE) technique, or the closely related maximum a posteriori (MAP) technique give two advantages, first it increases the chance of a correct call, and it also allows a confidence to be calculated for each call. In an embodiment, selecting the paternity call corresponding to the hypothesis with the greatest probability is carried out using maximum likelihood estimates or maximum a posteriori estimates. In an embodiment, a method is disclosed for determining the paternity of a gestating fetus that involves taking any method currently known in the art that uses a single hypothesis rejection technique and reformulating it such that it uses a MLE or MAP technique A Method for Paternity Determination The ffDNA is typically present at low fraction in a mixture with maternal DNA. In one embodiments, the mother has known genotype or the maternal genotype can be measured or inferred. Typically, the fraction of fetal DNA found in maternal plasma is between 2 and 20%, although in different conditions this percentage can range from about 0.01% to about 50%. In an embodiment, a microarray or other technique that gives intensity data on a per allele basis can be used to measure the maternal plasma. In an embodiment, sequencing can be used to measure the DNA contained in the maternal plasma. In these cases the allele intensity measurement or sequence read count at a particular allele is a sum of the maternal and fetal signals. Assuming that the mixture ratio of child to mother DNA is r to 1, the relative number of alleles at a locus consists of 2 alleles from the mother and 2r alleles from the child. In some embodiment, the loci comprise single nucleotide polymorphisms. Table 1 shows the relative number of each allele in the mixture for a selection of informative parent contexts.

TABLE 1

| Number of alleles by context | | |
|---|---|---|
| parent context | A in mixture | B in mixture |
| AA\|AA | 2 + 2r | 0 |
| AA\|BB | 2 + r | r |
| AB\|AA | 1 + 2r | 1 |
| AA\|AB | 2 + 2r or 2 + r | 0 or r |
| BB\|AA | r | 2 + r |
| BB\|BB | 0 | 2 + 2r |

Note that the choice of the above four contexts as being informative is not meant to be inclusive of all contexts that may be informative. Any combination of contexts may be used, and there is a significant amount of information that may be found in the genotypic measurements of any context.

Even in the presence of significant allele dropout rate from the child, there may be a clear distinction between signal where an allele is present and signal where an allele is not present. For example, consider the A allele measurements from SNPs in context pairs BB|BB and BB|AA and the B allele measurements from SNPs in from context pairs AA|AA and AA|BB. In each case, there should be no signal present in the first context and there should be signal present in the second context, wherever the child's alleles have not dropped out. However, if the alleged father is incorrect, there will sometimes be signal present in both contexts. Thus, the distribution of SNP measurements should be different, depending on whether the alleged father is correct or not.

The difference will typically be more observable at the high-signal end of the distribution, because these will be the SNPs where there is higher likelihood of having DNA contributions from the child. This difference can be observed by comparing high percentile values of the distributions of SNP measurements. Examples of possible percentile methods are nearest rank, linear interpolation between closest ranks, and weighted percentile.

For example, define $X_1$ as the set of A allele SNP measurements in context BB|BB and $X_2$ as the set of A allele measurements in context BB|AA, from all chromosomes. If the alleged father is correct, then the $99^{th}$ percentile value of $X_1$ will be significantly less than the $99^{th}$ percentile value of $X_2$. If the alleged father is incorrect, the $99^{th}$ percentile values of the two distributions will be closer together. Note than any percentile may be used equally well, for example, $95^{th}$ percentile, $90^{th}$ percentile, $85^{th}$ percentile or $80^{th}$ percentile. In an embodiment, for a particular measurement channel, X1 can be defined as the measurements from the context with no signal and X2 can be defined as the measurements from the context where the mother and father are both homozygous, and only the father alleles provide a signal (inherited through the child).

Define $p_1$ as the 99th (or $95^{th}$, $90^{th}$ etc.) percentile of the $X_1$ data and $p_2$ as the $99^{th}$ (or $95^{th}$, $90^{th}$ etc.) percentile of the $X_2$ data. Define the test statistic t as $p_1/p_2$. Note that other functions of $p_1$ and $p_2$ that demonstrate the difference in values may be used equally well. The value of t will vary depending on the amount of child DNA present in the sample, which is not known. Therefore, classification thresholds for t can not be calculated a priori.

The test statistic t for a single sample can be compared to a distribution generated from the genotypes of many individuals who are known not to be the father, using the following procedure. Assume that the genotypes from a large set of unrelated individuals are available.

1. For each unrelated individual, assume that it is the father and calculate the value of the test statistic t.
2. Let $T_u$ be the set of t measurements from the unrelated males. Fit a distribution to $T_u$. This is the distribution of t for the particular sample, under the null hypothesis. The null hypothesis is "genotypes do not come from father of child present in sample". The distribution Pu(t) could be a maximum likelihood fit or method of moments fit to a known distribution e.g. a Gaussian distribution, a kernel density fit using a kernel function e.g. Gaussian, box, triangle etc, or any other appropriate distribution fitting method.
3. Consider the genotypes of the alleged father and calculate the corresponding test statistic $t_c$.
4. The true father is expected to result in a smaller value of t than an unrelated individual. The probability of an unrelated father producing $t_c$ or a more outlying value is the cumulative density function of $P_u$ evaluated at $t_c$. Thus, the p-value p for rejecting the null hypothesis is given by the following:

$p = \int_0^{t_c} P_u(t) dt$

If p falls below a significance threshold a then the hypothesis that the father alleged is an unrelated individual can be rejected with significance a. If p is greater than a then the null hypothesis cannot be rejected, and the alleged father may be unrelated to the child present in the sample. The significance threshold a defines the probability that an unrelated individual could be classified as the correct father. For example, with a threshold of a equal to 0.01, one percent of unrelated individuals could be identified as the correct father.

Various methods can be considered for combination of data from the A and B allele channels. For example, two simple methods are to require that the p-value from all channels be below a threshold, or to require that the p-value from any channel be below the threshold.

In some embodiments, the paternity testing method assumes that child DNA is present at sufficient concentration to distinguish between SNPs that have or do not have signal from the child. In the absence of sufficient child DNA concentration, this method may report "incorrect father" because expected paternally inherited alleles are not measured in the maternal plasma. In an embodiment, a method is described that can confirm the presence of sufficient child DNA before applying the paternity test. The child presence confirmation is based on calculation of a test statistic that is proportional to the child DNA concentration, but does not require father genotypes. If the test statistic is above the required threshold, then the concentration of child DNA is sufficient to perform the paternity test.

Consider the set of SNPs (from all chromosomes combined) where the mother genotype is AA and the B channel is measured. A signal is expected only on the subset of SNPs where the child genotype contains a B, but these SNPs cannot be identified a priori without the father genotypes, which are not available. Instead, consider the SNP populations frequencies $\{f_i\}$ where $f_i$ is the sample mean number of Bs in the genotype of SNP i, based on a large sample population. Note that most SNPs where the mother genotype is AA will have $f_i$ less than 0.5, but the distribution of $f_i$ on these SNPs extends almost to one. Consider two sets of SNPs, $S_1$ and $S_2$, where $S_1 = \{i: f_i < T_L\}$ and $S_2 = \{i: f_i > T_H\}$. The thresholds $T_L$ and $T_H$ are set so that very few SNPs in $S_1$ are expected to have a B and many SNPs in $S_2$ are expected to have a B, and each set has sufficient population. In one embodiment, the algorithm uses $T_L = 0.05$ and $T_H = 0.7$, while other values for TL and TH might work equally well or better. Let $y_i$ be the B channel measurement from SNP i, $Y_1=\{y_i:i\in S_1\}$, and $Y_2=\{y_i:i\in S_2\}$. The distributions of $Y_1$ and $Y_2$ will be very similar because most SNPs in both distributions will have no signal. However, some non-trivial number of SNPs in $S_2$ are expected to have child signal and very few SNPs in $S_1$ are expected to have child signal. Therefore, the tail of $Y_2$ should extend to higher intensity than the tail of $Y_1$. Let $p_t$ be a percentile close to 1, for example, the 99th percentile. In the presence of sufficient child DNA, the pt percentile of $Y_2$ should be significantly higher than the pt percentile of $Y_1$. Thus, the test statistic s can be defined as follows.

$$s=\text{percentile}(Y_2;p_t)-\text{percentile}(Y_1;p_t)$$

In one embodiment, the test statistic may be normalized by a variety of methods to attempt to account for amplification differences between arrays. In one embodiment, the normalization could be done on a per chromosome basis. In one embodiment, the normalization could be done on a per array basis. In one embodiment, the normalization could be done on a per sequencing run basis.

The following calculation shows how the thresholds $T_L$ and $T_H$ are able to distinguish the effect of child DNA in particular maternal sample, based on approximate numbers of SNPs and dropout rates. Table 3 shows some data from In one embodiment, the method involves the following assumptions:
Population frequencies are calculated from a large population data set, for example, more than 500 individuals, more than 1,000 individuals, more than 5,000 individuals or more than 20,000 individuals, and the number of SNPs in each context comes from an example mother and father.
There are no SNPs where mother is AA and father is BB (in reality, these are approximately 8 percent of mother AA SNPs)
Half of SNPs where father has B result in child B.
Child dropout rate is 90 percent.
Measurements with child signal will be higher than measurements without child signal Table 3 shows some data from a particular paternity case using the disclosed method with the above parameters. The 98th percentile measurement from $S_1$ is not expected to include any SNPs with child signal present. The 98th percentile measurement from $S_2$ is expected to include about 50 SNPs with child signal present. The difference between the two should reflect the amount of child signal.

TABLE 3

Data pertaining to paternity determination

| set | definition | num SNPs in set | average $f_i$ in set | num SNPs father B | num SNPs child signal | fraction of set, child signal |
|---|---|---|---|---|---|---|
| $S_1$ | $f_i < 0.05$ | 13300 | 0.012 | 171 | 9 | 0.0007 |
| $S_2$ | $f_i > 0.7$ | 3000 | 0.79 | 2370 | 119 | 0.039 |

Figure 2:
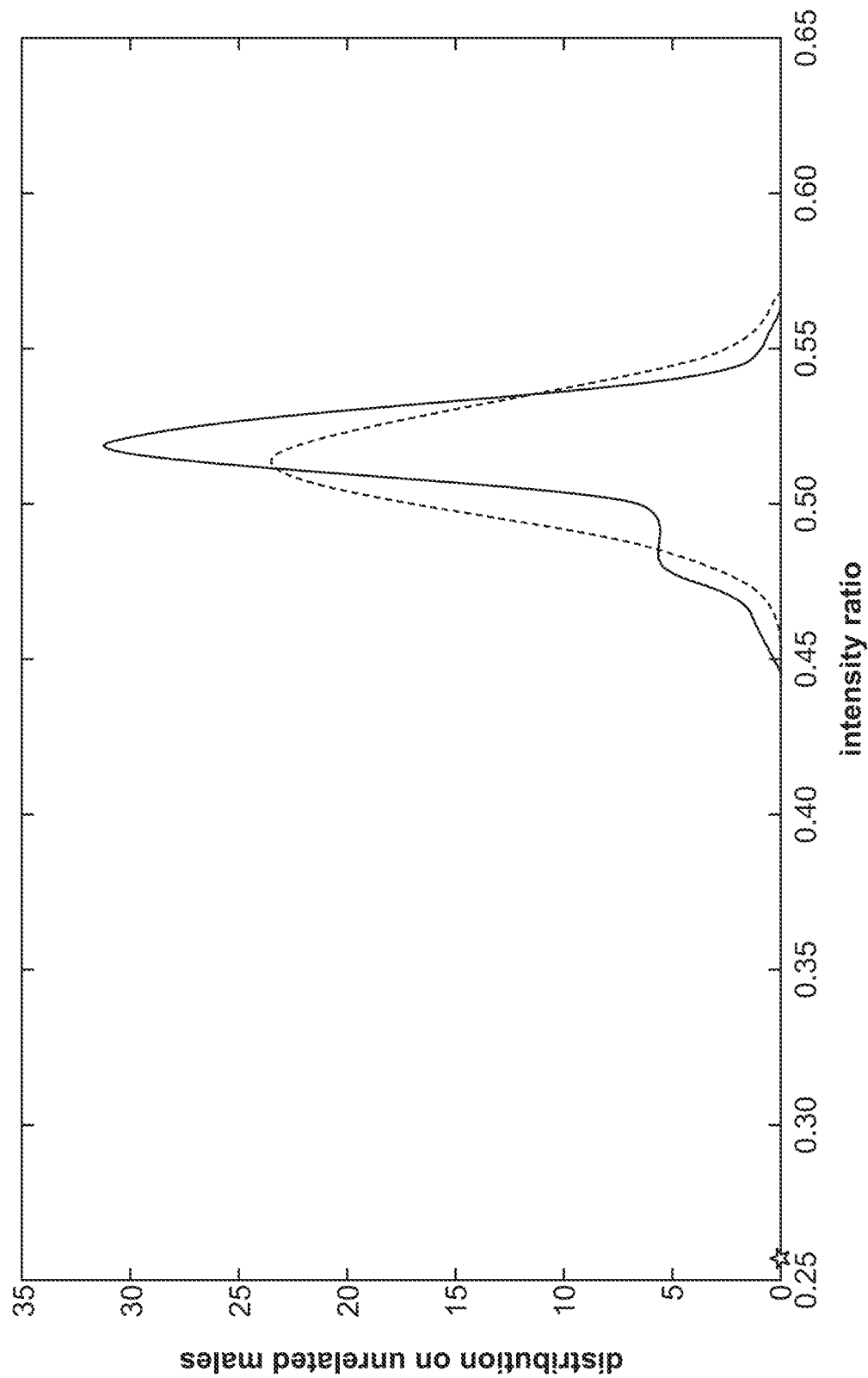
FIG. 2 shows the distribution of paternity related test statistic for 200 unrelated males and the biological father.

FIG. 1 shows the distribution of allele intensity data for contexts AA|AA and AA|BB from a maternal plasma sample collected at 38 weeks. The B allele is measured. Note that the AA|BB distribution extends significantly higher than the AA|AA distribution, showing that the B allele (which is only present in the child's genome) is present in the AA|BB context but not the AA|AA context. FIG. 2 comes from the same maternal plasma sample as FIG. 1, and shows the distribution of the test statistic t for allele B using the genotypes from 200 unrelated individuals. Two distributions are shown (the two curves): the maximum likelihood Gaussian fit and a kernel distribution. The value $t_c$ for the biological father is marked with a star. The p-value is less than $10^{-7}$ for the null hypothesis that the alleged father is unrelated to the child.

Table 4 presents results from 8 maternal blood samples at varying stages of pregnancy. A p-value is calculated based on the data measured from each channel (A allele and B allele) for the correct father. If both channel p-values are required to be below 0.01, then two samples are classified incorrectly. If only one channel is required to pass the threshold, then all samples are correctly classified. Any number of metrics and thresholds may be used for confirming or excluding parentage. For example, one could use a cut off p-value of 0.02, 0.005, 0.001, or 0.00001; similarly, one could demand that one or both channel p-values are below a given threshold, or one could have two different thresholds for the different channel p-values.

TABLE 4

P-values for two channels for eight paternity determinations.

| Weeks pregnancy | p-value (Y) | p-value (X) |
|---|---|---|
| 11 | $2.3 \times 10^{-7}$ | $<10^{-7}$ |
| 16 | 0.013 | $<10^{-7}$ |
| 17 | $<10^{-7}$ | $<10^{-7}$ |
| 17 | $<10^{-7}$ | 0.0002 |
| 20 | $<10^{-7}$ | $<10^{-7}$ |
| 28 | 0.14 | 0.0048 |
| 38 | $<10^{-7}$ | $<10^{-7}$ |
| 38 | $<10^{-7}$ | $<10^{-7}$ |

Figure 3:
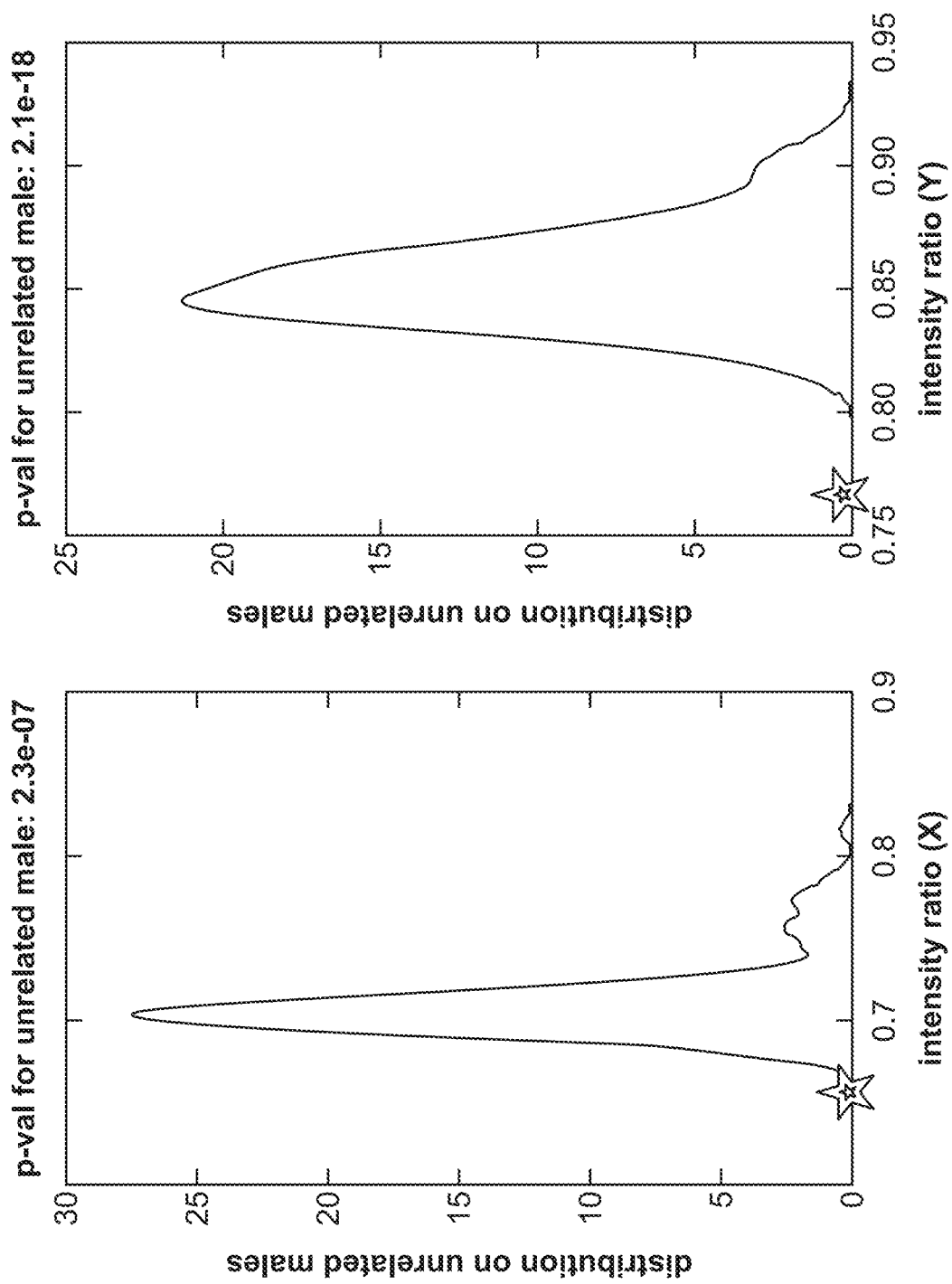
FIG. 3 shows two distributions of intensity ratios for 200 unrelated males and the biological father. Each graph correspond to a different input channels.

Table 4 shows the P-values for the null hypothesis that the correct father is an unrelated individual. Each row corresponds to a different maternal blood sample, and the corresponding paternal genetic sample. Genetic measurements made on 200 unrelated males were used as a control. The curve in FIG. 3 shows the distribution of intensity ratios for 200 unrelated males, and the star represents the intensity ratio for the biological father. This data is taken from a case where the blood was drawn from a mother who was 11 weeks pregnant.

Figure 4:
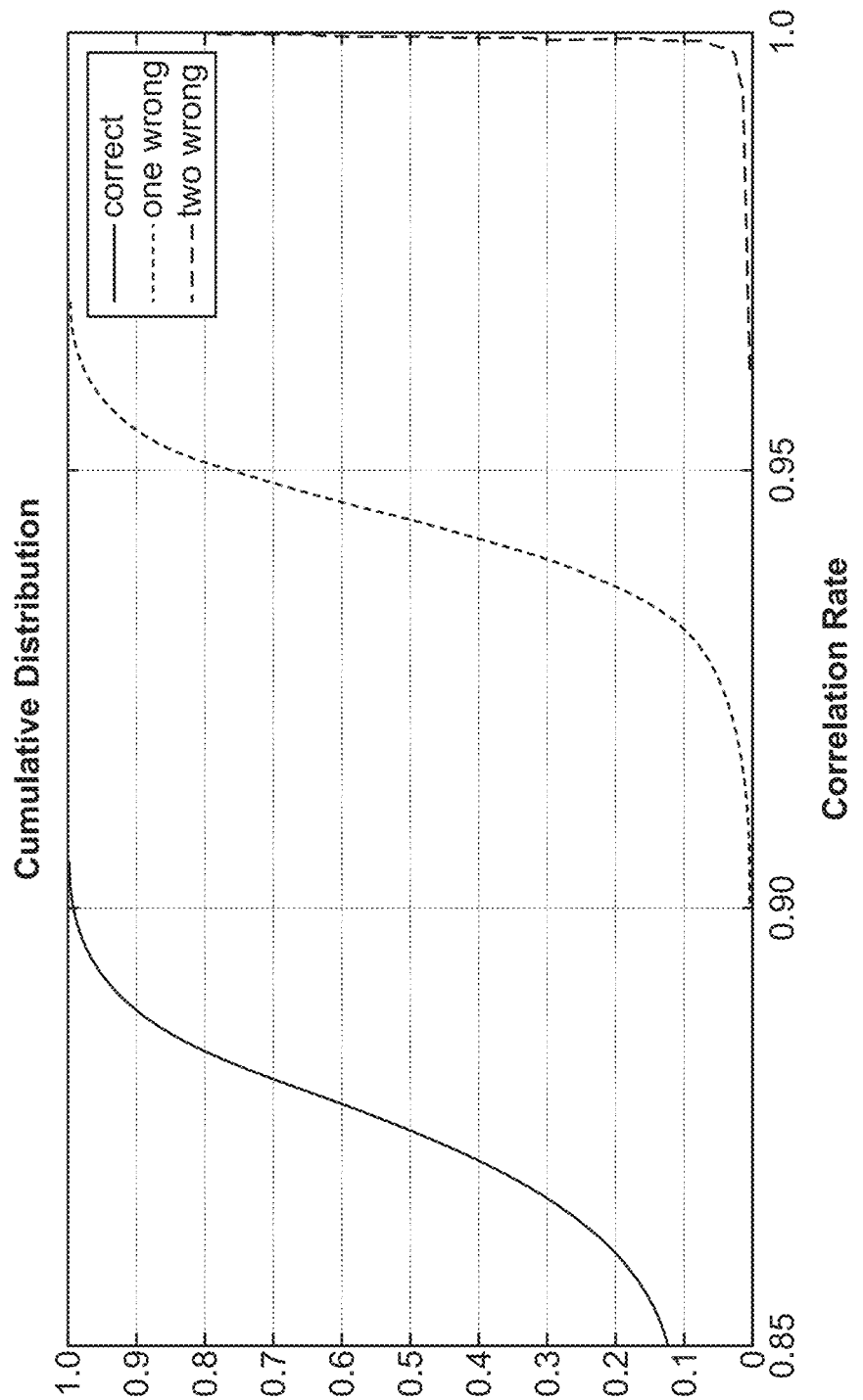
FIG. 4 shows the cumulative distribution frequency (cdf) curves for the correlation ratio between the fetal genotypic measurements and the parental genotypic measurements for three cases.
Figure 5:
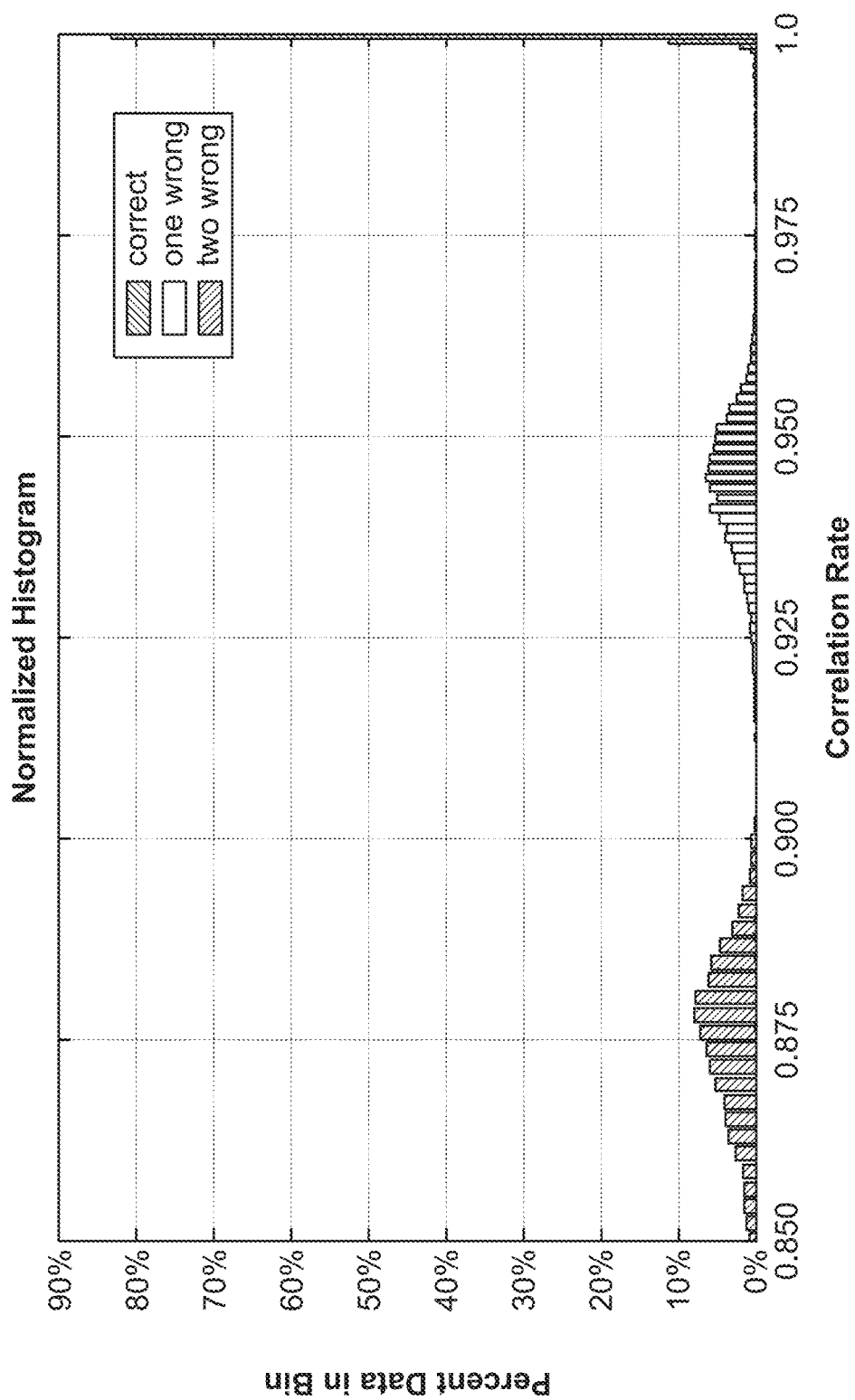
FIG. 5 shows histograms of the correlation ratio between the fetal genotypic measurements and the parental genotypic measurements for three cases.

FIG. 4 shows the cumulative distribution frequency (cdf) curves for the correlation ratio between the fetal genotypic measurements and the parental genotypic measurements for three cases: (1) where both the pregnant mother and the alleged father are the biological parents of the fetus ("correct", rightmost curve), (2) where the pregnant mother is the biological mother of the fetus, but the alleged father is not the biological father of the fetus ("one wrong", middle curve) and (3) where neither the pregnant mother nor the alleged father are the biological parents of the fetus ("two wrong", leftmost curve). The cdf curves are the correlation ratio between genotypic data of the embryo, calculated from data measured on a single cell, and the genotypic data of the assumed parents when zero, one or two of the assumed parents are actually the genetic parents of the fetus. Note that the labels for "correct" and "two wrong" are reversed. FIG. 5 shows histograms for the same three cases. Note that this histogram is made up of more than 1000 cases where one or both parents are incorrect. The histogram of correlation rate measured between the genotypic data of the fetus, as measured on a single cell, and the genotypic data of the assumed parents when zero, one or two of the assumed parents are actually the genetic parents of the fetus.

Figure 6:
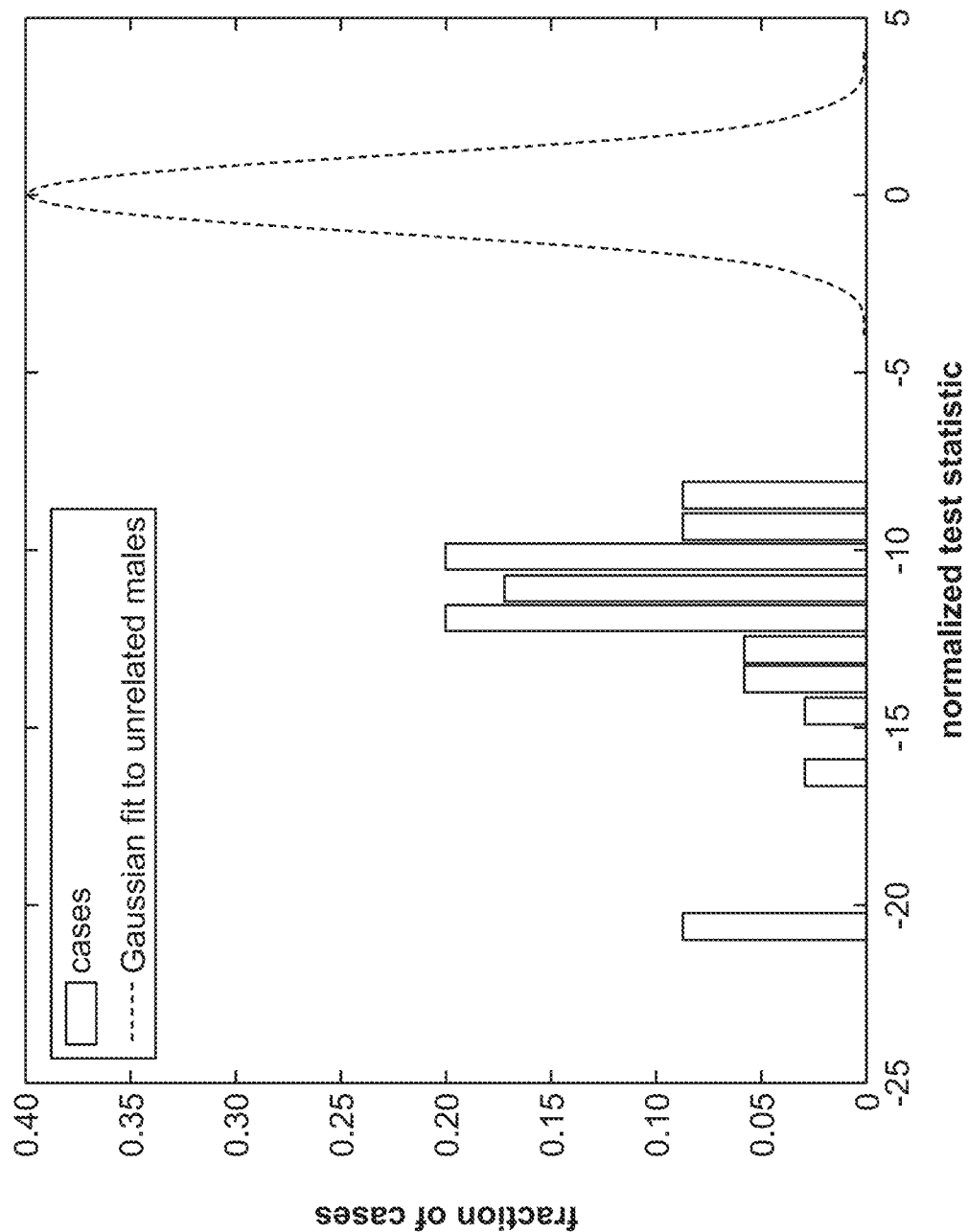
FIG. 6 shows a histogram of the paternity test statistic for 35 samples as compared to an idealized Gaussian distribution of test statistics for 800 unrelated males.

Thirty five paternity results are shown in FIG. 6 using the instant method for paternity testing. They were run on samples collected from pregnant women with gestational ages ranging from 9 to 40 weeks. The red curve on the right represents a normalized Gaussian distribution of the paternity testing statistic for 800 unrelated males. The distribution of unrelated males is different for each case; a normalized distribution is used here for visualization purposes.

The blue bars represent the normalized test statistic for the correct (suspected) father. It is clear that the correct fathers are clearly separated from the unrelated males. Note that the normalized test statistic crudely approximates standard deviations, therefore, "−5" on the graph below is about 5 standard deviations from the mean. Thus all assumed correct fathers in this cohort have been confirmed as the correct fathers with a significance of at least 99.9999%.

In one embodiment of the invention, the knowledge of the parental haplotypes could be used to increase the accuracy of the test. For example, if the two haplotypes of the father are known for a given segment of a chromosome, then the knowledge of which SNPs are present for cases where there is no drop out can be used to determine which SNPs should be expected for those cases where there may be dropout. For example, imagine a set of three SNPs that are linked, that is, they are located close together on the same chromosome, and where the contexts of the mother and the alleged father are: AA|AB, AA|AB, AA|BA. Note that when the genotype of a parent is phased, then AB BA, since the first of the two letters represents the alleles on the first haplotype, and the second letter represents the alleles on the second haplotype. Now imagine that for those three SNPs, a significant level of the B allele is measured for all three; in this case, the chance that the alleged father is the correct father is low, because the two father haplotypes are A, A, B and B, B, A, while the measured fetal genotype is positive for B at all three SNPs, and the mother could only have contributed an A. If the father genotype was not phased, it would not be possible to rule out this alleged father given this set of measurements. In one embodiment, that determination of the father haplotypes may be determined given the diploid genomic DNA measurements along with haploid genetic measurements made on one or more sperm. The use of more than one sperm can allow the determination of the haplotypes with more accuracy, as well as how many cross overs may have occurred, for each of the chromosomes, along with their locations, during the meiosis that formed the sperm. A method to accomplish this paternal phasing may be found in greater detail in the four Rabinowitz patent applications referenced elsewhere in this document.

In an embodiment, the paternity determination is done exclusively using SNP measurements, and no data from single tandem repeats is used. In an embodiment, the paternity determination is done exclusively using both SNP and STR measurements. The SNP data may be measured using SNP microarrays, or it may be measured by sequencing. The sequencing may be untargeted, or it may be targeted, for example by using circularizing probes that are targeted to a set of polymorphic loci, or it may be use targeted by using capture by hybridization techniques. In some embodiments, the genetic data may be measured by a combination of methods; for example, the parental genetic data may be measured on a SNP microarray while the DNA isolated from maternal serum may be measured using targeted sequencing where capture hybridization probes are used to target the same SNPs as are found on the SNP microarray. In one embodiment a combination of the following types of data may be used to determine whether or not the alleged father is the biological father of the fetus: SNP data, STR data, crossover data, microdeletion data, insertion data, translocation data, or other genetic data.

Figure 7:
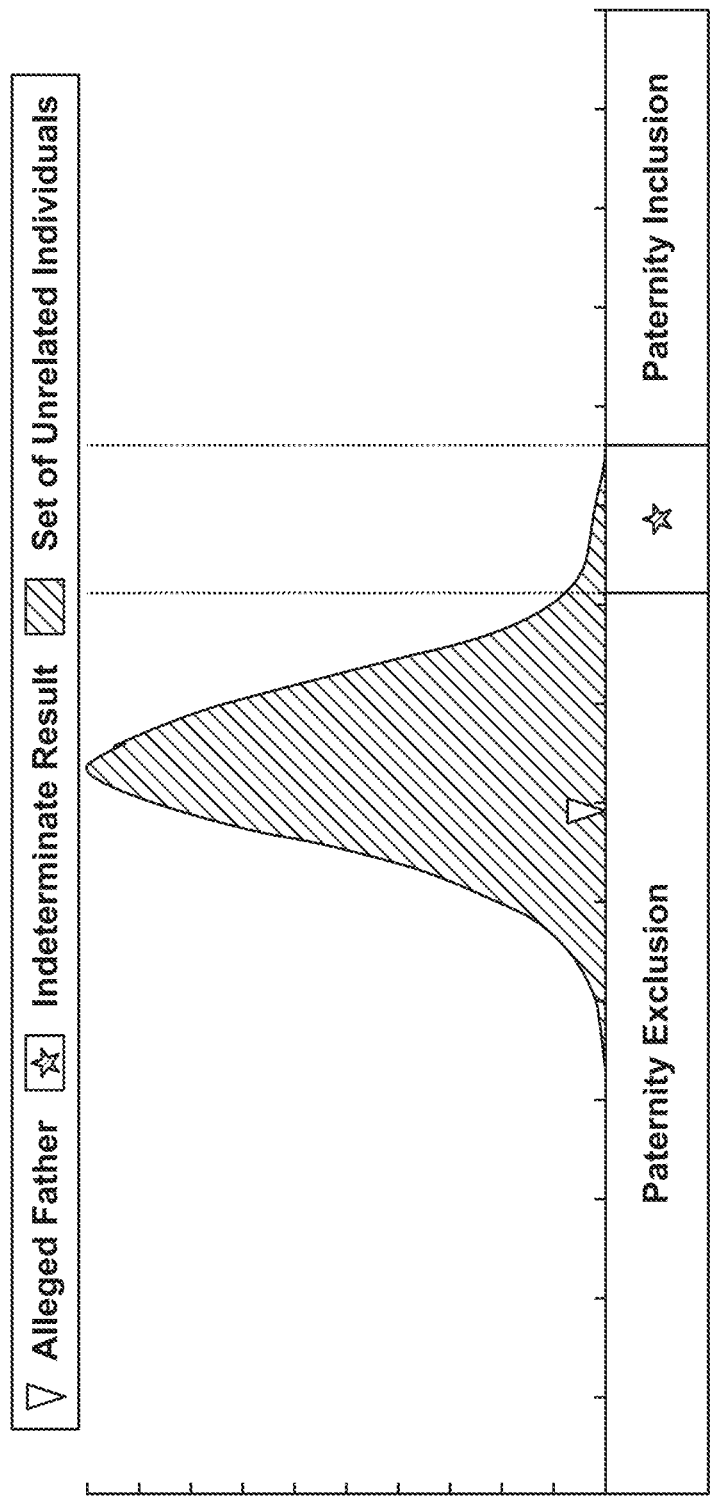
FIG. 7 shows an example of a report disclosing a paternity exclusion.
Figure 8:
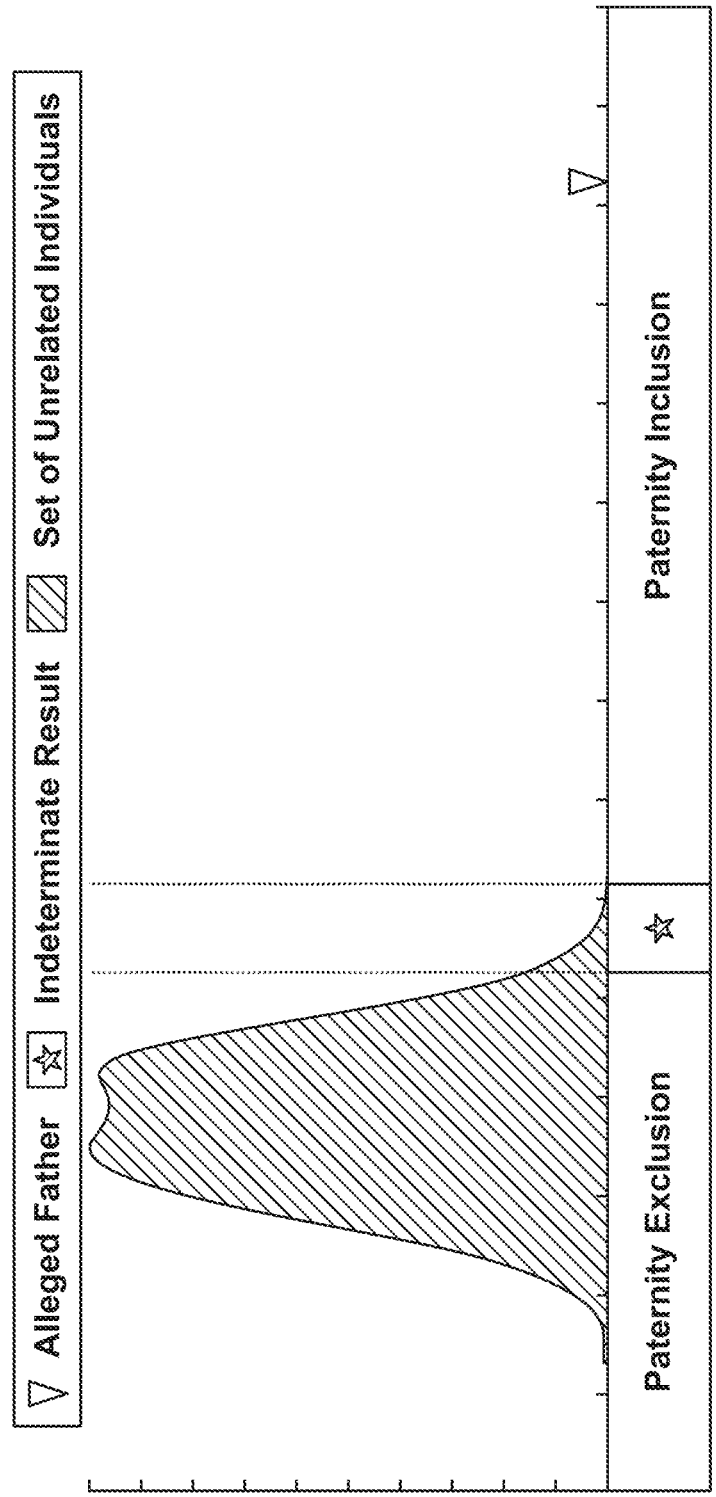
FIG. 8 shows an example of a report disclosing a paternity inclusion.
Figure 9:
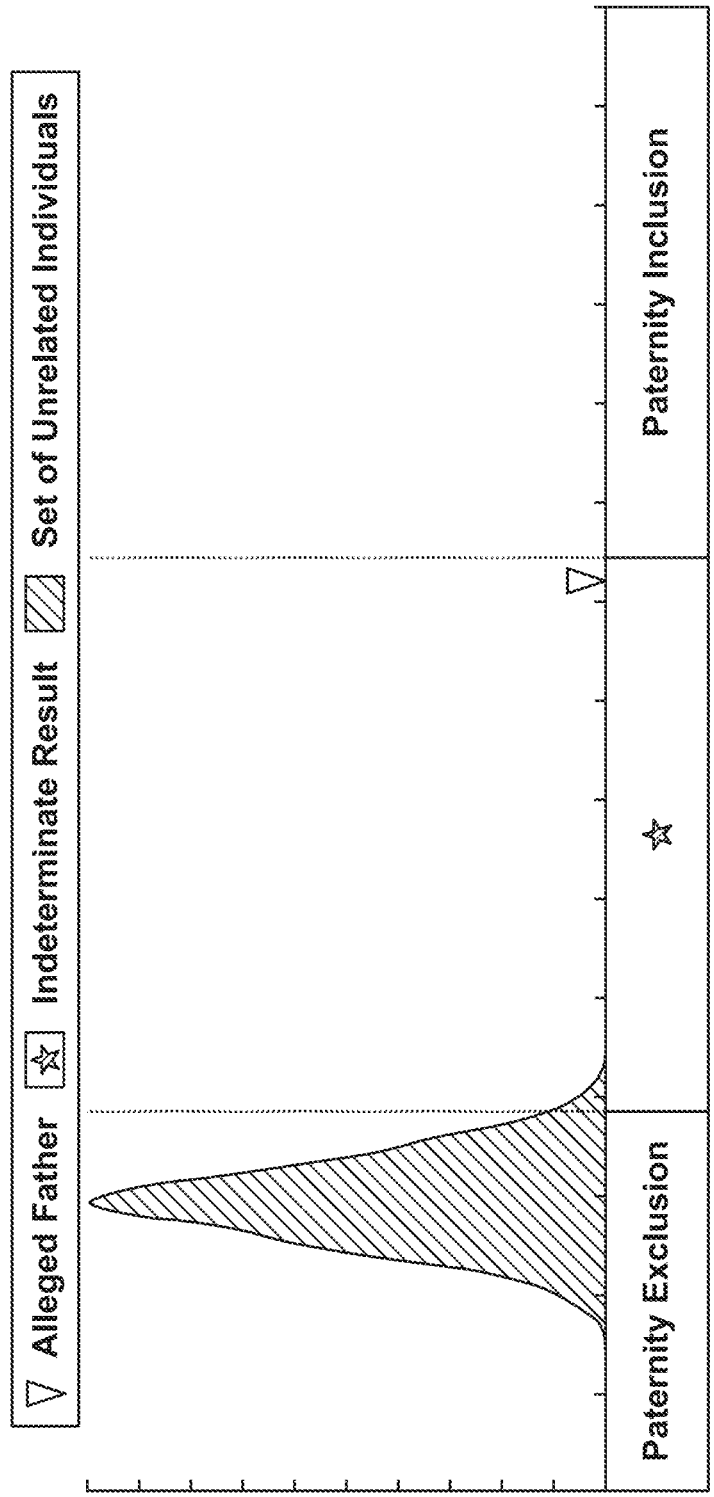
FIG. 9 shows an example of a report disclosing an indeterminate result.

In an embodiment, the method may comprise the generation of a report disclosing the established paternity of the fetus, or other target individual. In an embodiment, the report may be generated for the purpose of communicating the paternity determination. In an embodiment, the report may comprise a probability that the alleged father is the biological father of the fetus. Some examples of such a report are shown within; FIG. 7 is an example of a report disclosing a paternity exclusion, FIG. 8 is an example of a report disclosing a paternity inclusion and FIG. 9 is an example of a report indicating an indeterminate result. In one embodiment the report may comprise a graph containing a distribution of a paternity related metric for a plurality of unrelated individuals with respect to a given fetus and mother (shown as a grey curve), and an indication of the metric for the alleged father (shown as a triangle). The distribution of unrelated males is different for each case; in these three reports, an actual distribution of the test statistic for the fetus and unrelated males is used here. In an embodiment, the report may also contain an indication that the alleged father is more likely to be part of the distribution of unrelated individuals (e.g. FIG. 7), and therefore the alleged father is established to not be the biological father of the fetus; the fact that the triangle is in the paternity exclusion region of the graph indicates that this is a paternity exclusion. In an embodiment, the report may also contain an indication that the alleged father is more likely to not be part of the distribution of the paternity metric for unrelated individuals (e.g. FIG. 8), and the alleged father is established to be the biological father of the fetus; the fact that the triangle is in the paternity inclusion region of the graph indicates that this is a paternity inclusion. In an embodiment, the report may also contain an indication that the measurements are indeterminate (e.g. FIG. 9); the fact that the triangle is in the "indeterminate result" region of the graph indicates that no conclusion was made with respect to establishing the paternity of the fetus.

In one embodiment of the invention, the determination of whether or not the alleged father is the biological father of the fetus is done without using single tandem repeats (STRs). In one embodiment of the invention, the accuracy of the paternity determination is increased by phasing the parental genotypes. In one embodiment of the invention, the genotypes of one or more of the parents are phased with the use of genetic material from one or more individual related that parent. In one embodiment, the individual related to the parent is the parents father, mother, sibling, son, daughter, brother, sister, aunt, uncle, twin, clone, a gamete from the parent, and combinations thereof.

Another Method for Paternity Determination

In an embodiment, the maternal plasma and optionally the other genetic material may be measured by sequencing, for example using high throughput sequencers such as the HISEQ or MISEQ by ILLUMINA, or the ION TORRENT by LIFE TECHNOLOGIES.

Non-invasive paternity testing can be performed on a maternal blood sample if there is a sufficient concentration of free-floating fetal DNA. In general, the fraction of fetal DNA in most cases, the maternal plasma will be about between 2 percent to 20 percent, though it may be as low as 0.01%, or as high as 40%, partly depending on the gestational age. It has already been demonstrated that this range of fetal fraction is sufficient for paternity testing by a single-hypothesis rejection method using SNP microarrays.

High throughput sequencing is a far more precise platform which allows mathematical modeling of the expected measurement response at each SNP, for combinations of mother and child genotypes. In an embodiment, the maternal plasma and optionally the other genetic material may be measured by sequencing, for example using high throughput sequencers such as the HISEQ or MISEQ by ILLUMINA, or the ION TORRENT by LIFE TECHNOLOGIES. Confidences on paternity inclusions or exclusions may then be calculated by using probability and/or estimation theories.

In an embodiment, the method for paternity testing may include the following. For an alleged father, one may calculate the probability of the sequencing data, derived from the plasma, with respect to the two different hypotheses: (1) the alleged father is the correct (biological) father (Hc) and (2) the alleged father is not the correct (biological) father (Hw). The hypothesis that has the higher likelihood or a posteriori is then chosen. In an embodiment, this approach may be combined with a platform model which relates the allele ratio in the plasma to the observed number of sequenced A and B alleles. With the platform model available, it is possible to derive probabilistic likelihoods of the sequenced A and B alleles for each SNP location for each hypothesis.

One complication is that the amount of fetal fraction in the maternal plasma may vary between individuals and over time. In an embodiment, the method may account for this variability. There are several ways to address this type of variability. In an embodiment, the method may explicitly estimate the fetal fraction; in another embodiment, the method may put a prior on the unknown quantity and integrates over all possible values. An embodiment uses a prior that is it as a uniform distribution from 0 to some threshold, e.g. 40%. Any prior may work in theory. An embodiment, calculates likelihoods of various child fractions, either in continuous space or on a finite partition and integrates or sums over the range, respectively.

Consider maternal plasma with fetal fraction, f, and a single SNP where the expected allele ratio present in the plasma is r (based on the maternal and fetal genotypes). In an embodiment, the expected allele ratio is defined as the expected fraction of A alleles in the combined maternal and fetal DNA. For maternal genotype $g_m$ and child genotype $g_c$, the expected allele ratio is given by equation 1, assuming that the genotypes are represented as allele ratios as well.

$$r = fg_c + (1-f)g_m \quad (1)$$

The observation at the SNP comprises the number of mapped reads with each allele present, $n_a$ and $n_b$, which sum to the depth of read d. Assume that quality control measures have been applied to the mapping probabilities such that the mappings and allele observations can be considered correct. A simple model for the observation likelihood is a binomial distribution which assumes that each of the d reads is drawn independently from a large pool that has allele ratio r. Equation 2 describes this model.

$$P(n_a, n_b \mid r) = p_{bino}(n_a; n_a + n_b, r) = \binom{n_a + n_b}{n_a} r^{n_a}(1-r)^{n_b} \quad (2)$$

When the maternal and fetal genotypes are either all A or all B, the expected allele ratio in plasma will be 0 or 1, and $p_{bino}$ will not be well-defined. Additionally, this is not desirable because unexpected alleles are sometimes observed in practice. The binomial model can be extended in a number of ways. In an embodiment, it is possible to use a corrected allele ratio $r=1/(n_a+n_b)$ to allow a small amount of the unexpected allele to be accounted for. In an embodiment, it is possible to use training data to model the rate of the unexpected allele appearing on each SNP, and use this model to correct the expected allele ratio. When the expected allele ratio is not 0 or 1, the observed allele ratio may not converge to the expected allele ratio due to amplification bias or other phenomena. The allele ratio can then be modeled as a beta distribution centered at the expected allele ratio, leading to a beta-binomial distribution for $P(n_a, n_b \mid r)$ which has higher variance than the binomial.

A general platform model for the response at a single SNP may be defined as $F(a, b, g_c, g_m, f)$ (3), or the probability of observing $n_a=a$ and $n_b=b$ given the maternal and fetal genotypes, which also depends on the fetal fraction through equation 1.

$$F(a,b,g_c,g_m,f) = P(n_a=a, n_b=b \mid g_c, g_m, f) \quad (3)$$

Note that it may be feasible to simplify formula (3) by conditioning on a function of $g_c$, $g_m$ and f e.g. by using r as defined in (1) and the binomial example in (2). The equation for F could then be written $$F(a,b,g_c,g_m,f) = P(n_a=a, n_b=b \mid g_c, g_m, f) = P(n_a=a, n_b=b \mid r(g_c,g_m,f)) \quad (4)$$

In general the functional form of F may be a binomial distribution, beta-binomial distribution, multivariate Pólya distribution, an empirical distribution estimated from training data, or similar functions as discussed above. In an embodiment, the functional form of F takes different forms depending on the hypothesis for copy number on the chromosome in question.

A Method for the Calculation of the Fetal Fraction

Determining the fraction of fetal DNA that is present in the mixed fraction of DNA may be an integral part of any method for non-invasive prenatal paternity determination, ploidy calling, or allele calling. In some embodiments, the fetal fraction of the mixed sample may be determined using the genotypic data of the mother, the genotypic data of the father, and the measured genotypic data from the mixed sample that contains both maternal and fetal DNA. In the context of paternity testing, and also to a lesser extent in the case of ploidy calling, the identity of the father is not known, and therefore genotypic data of the biological father of a fetus may not be available. In these cases, it is important to have a method for fetal fraction determination that does not require the genotype of the biological father of the fetus. Described herein are several method by which to accomplish the fetal fraction estimate. These methods are described in a general way such that they are appropriate when the genotype of the biological father is available, and when it is not.

For a particular chromosome, suppose we are looking at N SNPs, for which we have the following data:

A set of NR plasma sequence measurements $S=(S_1, \ldots, S_{NR})$. In an embodiment, where we have (A,B) counts for alleles A and B for each SNP, s can be written as $s=((a_1, b_1), \ldots, (a_N, b_N))$, where $a_i$ is the a count on SNP i, $b_i$ is the b count on SNP i, and $\Sigma_{i=1:N}(a_i+b_i)=NR$ Parent data consisting of:
Genotype information: mother $G_m=(G_{m1}, \ldots, G_{mN})$, father $G_f=(G_{f1}, \ldots, G_{fN})$, where $G_{mi}$, $G_{fi} \in$ AA, AB, BB); and/or Sequence data measurements: NRM mother measurements $s_m=(s_{m1}, \ldots, s_{mnr})$, NRF father measurements $S_f=(S_{f1}, \ldots, S_{fnr})$. Similar to above simplification, if we have (A, B) counts on each SNP $s_m = ((a_{m1}, b_{m1}), \ldots, (a_{mN}, b_{mN}))$, $S_f = ((a_{f1}, b_{f1}), \ldots, (a_{fN}, b_{fN}))$
Collectively, mother, father child data may be denoted as $D = (G_m, G_f, S_m, S_f, S)$. In an embodiment, genotypic data from both parents are available; in an embodiment, genotypic data from only the mother is available; in an embodiment, genotypic data from only the father is available; in an embodiment, genotypic data from neither parent is available. In some embodiment, the maternal genotypic data may be inferred from the genotypic data measured in the mixed sample. Note that in general, parent data is desirable and increases the accuracy of the algorithm, but is not required.

Child fraction estimate $\hat{f}$ is the expected child fraction given the data:

$$\hat{f} = E(cfr|D) = \int f * P(f|D) df$$

In an embodiment, one may partition the interval of possible child fractions to a set C of finely spaced points and perform the calculations at each point which reduce the above equation to:

$$\hat{f} = E(f|D) = \sum_{f \in C} f * P(f|D)$$

P(f|D) is the likelihood of particular child fraction f given the data D. One may further derive using Bayes rule:

$$P(f|D) \sim P(D|f) * P(f)$$

where P(f) is the prior weight of particular child fraction. In an embodiment, this may be derived from uninformed prior(uniform) and may be proportional to the spacing between candidate child fractions in set C.

P(D|cfr) is the likelihood of given data given the particular child fraction, derived under the particular copy number assumptions on the relevant chromosomes. In an embodiment, one may we assume disomy on the chromosomes used. Likelihood of the data on all SNPs is the product of likelihood of data on individual SNPs.

$$P(D|f) = P(D|f, H) = \prod_i P(D|f, H, i)$$

Where i denotes a particular SNP, for SNP i we have:

$$P(D|f, H, i) = \sum_{g_m, g_f, g_c} P(D|g_m, g_f, g_c, f, H, i) * P(g_c|g_m, g_f, H) * P(g_m|i) * P(g_f|i)$$

where $g_m$ are possible true mother genotypes, $g_f$ are possible true father genotypes, $g_c$ are possible child genotypes, and $g_m, g_f, g_c \in \{AA, AB, BB\}$.

$P(g_m|i)$ is the general prior probability of mother genotype $g_m$ on SNP i, based on the known population frequency at SNP i, denoted $pA_i$. In particular:

$$p(AA|pA_i) = (pA_i)^2, p(AB|pA_i) = 2(pA_i)*(1-pA_i), p(BB|pA_i) = (1-pA_i)^2$$

Same for p(f|i), father genotype probability.

Let $P(g_c|g_m, g_f, H)$ denote is the probability of getting true child genotype=c, given parents m, f, and assuming hypothesis H, which we can easily calculate. For example, for a disomy:

| parents | | P(c\|m, f, disomy) | | |
|---|---|---|---|---|
| m | f | AA | AB | BB |
| AA | AA | 1 | 0 | 0 |
| AB | AA | 0.5 | 0.5 | 0 |
| BB | AA | 0 | 1 | 0 |
| AA | AB | 0.5 | 0.5 | 0 |
| AB | AB | 0.25 | 0.5 | 0.25 |
| BB | AB | 0 | 0.5 | 0.5 |
| AA | BB | 0 | 1 | 0 |
| AB | BB | 0 | 0.5 | 0.5 |
| BB | BB | 0 | 0 | 1 |

Let $P(D|g_m, g_f, g_c, H, i, f)$ be the probability of given data D on SNP i, given true mother genotype m, true father genotype f, true child genotype c, hypothesis H for the copy number and child fraction f. It can be broken down into probability of mother, father and child data as follows:

$$P(D|g_m, g_f, g_c, H, f, i) = P(s_m|g_m, i) P(G_m|g_m, i) P(s_f|g_f, i) P(G_f|g_f, i) P(s|g_m, g_c, H, f, i)$$

The probability of mother illumina genotype data $g_{mi}$ at SNP i compared to true genotype $g_m$, assuming illumina genotypes are correct, is simply:

$$P(G_m|g_m, i) = \begin{cases} 1 & g_{mi} = g_m \\ 0 & g_{mi} \neq g_m \end{cases}$$

In an embodiment, the probability of mother sequence data at SNP i, in case of counts $S_{mi} = (am_i, bm_i)$, with no extra noise or bias involved, is the binomial probability defined as: $P(S_m|, i) = P_{X|m}(am_i)$ where $X|m \sim \text{Binom}(p_m(A), am_i + bm_i)$ with $p_m(A)$ defined as:

| | m | | | | |
|---|---|---|---|---|---|
| | AA | AB | BB | A | B | nocall |
| p(A) | 1 | 0.5 | 0 | 1 | 0 | 0.5 |

A similar equation applies for father probabilities.

Note that it is possible to get an answer without the parent data, especially without the father data. For example if no father genotype data F is available, one can use $P(G_f|g_f, i) = 1$. If no father sequence data $S_f$ is available, one can use $P(S_f|g_f, i) = 1$. In an embodiment, information from different chromosomes is aggregated using averages, weighted average or a similar function.

Another Method for the Calculation of the Fetal Fraction

Another method for determining the fraction of fetal DNA in a mixture of DNA is described here. In one embodiment, a version of a maximum likelihood estimate of the fetal fraction f for a paternity test, ploidy test, or other purpose, may be derived without the use of paternal information. Define $S_0$ as the set of SNPs with maternal genotype 0 (AA), $S_{0.5}$ as the set of SNPs with maternal genotype 0.5 (AB) and $S_1$ as the set of SNPs with maternal genotype 1 (BB). The possible fetal genotypes on $S_0$ are 0 and 0.5, resulting in a set of possible allele ratios $$R_0(f) = \left\{0, \frac{f}{2}\right\}.$$

Similarly, $R_{0.5} = \{0.5-f, 0.5, 0.5+f\}$ and $$R_1(f) = \left\{1 - \frac{f}{2}, 1\right\}.$$

All or any subset of the sets $S_0$, $S_{0.5}$ and $S_1$ can be used to derive a child fraction estimate.

Define $N_{a0}$ and $N_{b0}$ as the vectors formed by sequence counts for SNPs in $S_0$, $N_{a0.5}$ and $N_{b0.5}$ similarly for $S_{0.5}$, and $N_{a1}$ and $N_{b1}$ similarly for $S_1$. The maximum likelihood estimate $\hat{f}$ of f, using all maternal genotype sets, is defined by equation 4.

$$\hat{f} = \arg\max_f P(N_{a0}, N_{b0}|f) P(N_{a0.5}, N_{b0.5}|f) P(N_{a1}, N_{b1}|f) \quad (4)$$

Assuming that the allele counts at each SNP are independent conditioned on the SNP's plasma allele ratio, the probabilities can be expressed as products over the SNPs in each set:

$$P(N_{a0}, N_{b0}|f) = \Pi_{s \in S_0} P(n_{as}, n_{bs}|f)$$

$$P(N_{a1}, N_{b1}|f) = \Pi_{s \in S_1} P(n_{as}, n_{bs}|f) \quad (5)$$

where $n_{as}$, $n_{bs}$ are the counts on SNPs s.

The dependence on f is through the sets of possible allele ratios $R_0(f)$, $R_{0.5}(f)$ and $R_1(f)$. The SNP probability $P(n_{as}, n_{bs}|f)$ can be approximated by assuming the maximum likelihood genotype conditioned on f. At reasonably high fetal fraction and depth of read, the selection of the maximum likelihood genotype will be high confidence. For example, at fetal fraction of 10 percent and depth of read of 1,000, consider a SNP where the mother has genotype 0. The expected allele ratios are 0 and 5 percent, which will be easily distinguishable at sufficiently high depth of read. Substitution of the estimated child genotype into equation 5 results in the complete equation (6) for the fetal fraction estimate.

$$\hat{f} = \arg\max_f \begin{bmatrix} \Pi_{s \in S_0} \left(\max_{r_s \in R_0(f)} P(n_{as}, n_{bs} | r_s)\right) \\ \Pi_{s \in S_{0.5}} \left(\max_{r_s \in R_{0.5}(f)} P(n_{as}, n_{bs} | r_s)\right) \\ \Pi_{s \in S_1} \left(\max_{r_s \in R_1(f)} P(n_{as}, n_{bs} | r_s)\right) \end{bmatrix}$$

The fetal fraction must be in the range [0, 1] and so the optimization can be easily implemented by a constrained one-dimensional search.

Another method would be to sum over the possible genotypes at each SNP, resulting in the following expression (7) for $P(n_a, n_b|f)$ for a SNP in $S_0$. The prior probability $P(r)$ could be assumed uniform over $R_0(f)$, or could be based on population frequencies. The extension to groups $S_{0.5}$ and $S_1$ is trivial.

$$P(n_a, n_b|f) = \Sigma_{r \in R_0(f)} P(n_a, n_b|r) P(r) \quad (7)$$

Derivation of Probabilities

A confidence can be calculated from the data likelihoods of the two hypotheses $H_{tf}$ i.e. the alleged father is the biological father and $H_{wf}$ i.e. the alleged father is not the biological father. The objective is to calculate P(H|D) i.e. probability of hypothesis given data, for each hypothesis and infer which hypothesis is more likely. In one embodiment, this may be done using Bayes rule: P(H|D)~P(D|H)*P(H) where P(H) is the prior weight of the hypothesis, and where P(D|H) is the likelihood of data given the hypothesis.

Consider P(D|H, f) i.e. the likelihood of data given hypothesis for a particular child fraction. If a distribution on child fraction is available, it is possible to derive $$P(D|H) = \int P(D, f|H) df$$

and further, $$P(D|H) = \int P(D|H, f) P(f|H) df$$

Note that P(f|H) is independent of the hypothesis i.e. P(f|H)=P(f) since the child fraction is the same regardless of whether the alleged father is the biological father or not, and any reasonable prior P(f) could be chosen e.g. a uniform prior from 0 to 50% child fraction. In an embodiment, it is possible to use only one child fraction, $\hat{f}$. In this case, $$P(D|H) = P(D|H, \hat{f})$$

Consider the likelihood P(D|H, f). The likelihood of each hypothesis is derived based on the response model, the estimated fetal fraction, the mother genotypes, the alleged father genotypes, allele population frequencies, the plasma allele counts and SNPs. Let D represent the data as defined before.

In an embodiment, it is assumed that the observation at each SNP is independent conditioned on the plasma allele ratio, thus the likelihood of a paternity hypothesis is the product of the likelihoods on the SNPs:

$$P(D | H, f) = \prod_{SNPs\ i} P(D | H, f, i)$$

The following equations describe how one may derive the likelihood for a single SNP i and a single child fraction f. Equation 8 is a general expression for the likelihood of any hypothesis H, which will then be broken down into the specific cases of $H_{tf}$ and $H_{wf}$. Note that genotypes, $g_m$, $g_{tf}$, $g_{df}$, and $g_c$, take values in {AA, AB, BB} which translates to {0, 0.5, 1} where AA=0, AB=0.5, BB=1. Also, $g_{tf}$ denote the genotypes of the true father and $g_{df}$ denote the genotypes represented by the data provided for the father. In case of $H_{tf}$, $g_{tf}$ and $g_{df}$ are equivalent.

$$P(D|f, H, i)^* = \Sigma_{g_m, g_{tf}, g_{df}, g_c \in \{0, 0.5, 1\}}$$
$$P(D|g_m, g_{df}, g_c, f, H, i)^* P(g_c|g_m, g_{tf}, H)^* P(g_m|i)^* P(g_{tf}|i)^* P(g_{df}|i) \quad (8)$$

In the case of the hypothesis $H_{tf}$, the alleged father is the biological father and the fetal genotypes are inherited from the maternal genotypes and alleged father genotypes. The equation above simplifies to:

$$P(D | f, H = H_{tf}, i) = \sum_{g_m, g_{tf}, g_c \in \{0, 0.5, 1\}} P(D | g_m, g_{tf}, g_c, f, H = H_{tf}, i) *$$
$$P(g_c | g_m, g_{tf}, H = H_{tf}) * P(g_m | i) * P(g_{tf} | i)$$

Further, $$P(g_c|g_m, g_{tf}, H = H_{tf}) = P(g_c|g_m, g_{tf})$$

and $$P(D|g_m, g_{tf}, g_c, f, H = H_{tf}, i) = P(s_m|g_m, i) P(G_m|g_m, i)$$
$$P(s_f|g_{tf}, i) P(G_f|g_{tf}, i) P(s|g_m, g_c, f, i) \quad (9)$$

In the case of $H_{wf}$, the alleged father is not the biological father. One estimate of the true father genotypes may be generated using the population frequencies at each SNP. Thus, the probabilities of child genotypes may be determined by the known mother genotypes and the population frequencies, i.e. the data do not provide additional information on the genotypes of the biological father. In this case, the equation above does not further simplify and stays as:

$$P(D \mid f, H = H_{wf}, i) =$$
$$\sum_{g_m, g_{tf}, g_{df}, g_c \in \{0, 0.5, 1\}} P(D \mid g_m, g_{df}, g_c, f, H = H_{wf}, i) *$$
$$P(g_c \mid g_m, g_{tf}, H = H_{wf}) * P(g_m \mid i) * P(g_{tf} \mid i) * P(g_{df} \mid i)$$

Further, $$P(g_c \mid g_m, g_{tf}, H = H_{wf}) = P(g_c \mid g_m, g_{tf})$$

where the only information on $g_{tf}$ are the population priors and:

$$P(D \mid g_m, g_{tf}, g_c, f, H = H_{wf}, i) = P(s_m \mid g_m, i) P(G_m \mid g_m, i)$$
$$P(s_f \mid g_{df}, i) P(G_f \mid g_{df}, i) P(s \mid g_m, g_c, f, i) \quad (10)$$

In both expressions of the likelihoods, P(D|f, H, i), i.e. for both hypotheses, the response model, $P(s \mid g_m, g_{df}, g_c, f, H)$ is generalized. Specific examples are mentioned elsewhere in the document in discussions on general platform models. Some examples for the response model include the binomial distribution, beta-binomial distribution, multivariate Pólya distribution, an empirical distribution estimated from training data, or similar functions as discussed above.

In some embodiments, the confidence $C_p$ on correct paternity can be calculated from the likelihoods $P(D|H_{tf})$ and $P(D|H_{wf})$. In an embodiment this calculation may be calculated using Bayes rule as follows:

$$C_p = \frac{P(D \mid H_{tf}) P(H_{tf})}{P(D \mid H_{tf}) P(H_{tf}) + P(D \mid H_{wf}) P(H_{wf})}$$

or written for a more specific case as a product over SNPs of the two likelihoods:

$$C_p = \frac{\Pi_i P(D \mid H_{tf}, G_{ms}, G_{tf}, f)}{\Pi_s P(n_{as}, n_{bs} \mid H_t, G_{ms}, G_{tf}, f) + \Pi_s P(n_{as}, n_{bs} \mid H_f, G_{ms}, G_{tf}, f)}$$

In another embodiment the confidence may be calculated as follows:

$$C_p = \frac{P(D \mid H_{tf})}{P(D \mid H_{tf}) + P(D \mid H_{wf})}$$

Other reasonable functions of the likelihoods are also possible.

EXPERIMENTAL SECTION

Experiment 1

Twenty one pregnant women with confirmed paternity and gestational ages between 6 and 21 weeks were enrolled. Participants voluntarily donated blood as part of our IRB approved research program, and were drawn from IVF centers, OB offices, and the general population in different locations in the U.S. Cell free DNA (ffDNA) isolated from maternal plasma, along with DNA from the mother and alleged father, were amplified and measured using a SNP array. An informatics method disclosed herein was used to exclude or include paternity for 21 correct fathers and 36,400 incorrect fathers by comparing each alleged father against a reference distribution generated from a set of over 5,000 unrelated individuals. 20 out of 21 samples had sufficient fetal DNA to return results. Twenty of twenty (100%) of paternity inclusions were correct. 36,382 of 36,382 paternity exclusions were correct (100%), with 18 "no calls" due to intermediate genetic similarity. There were no miscalls.

The population was made up of couples who donated their blood for prenatal research. The women had to have singleton pregnancies, be in the first or second trimester, and have confirmed paternity. Blood samples were collected from women using CELL-FREE blood tubes (STRECK) containing white blood cell preservative, and genetic samples were collected from the father, either as a blood (EDTA) or buccal sample. Written informed consent was obtained from all participants, and the genetic samples were collected from patients enrolled in an IRB approved study.

Mother blood was centrifuged to isolate the buffy coat and the serum. The genomic DNA in the maternal and alleged paternal buffy coat and the DNA in the maternal serum were prepared for analysis and run on ILLUMINA INFINIUM CYTO12 SNP arrays using standard protocols. Briefly, serum DNA was isolated using QIAGEN CIRCULATING NUCLEIC ACID kit and eluted in 45 ul buffer according to manufacturer's instructions. Twenty microliter eluate was used in a blunt ending reaction in 1×NEB 4 buffer, 0.42 mM dNTP and 2.5 U T4 DNA Polymerase (NEW ENGLAND BIOLABS), incubated at 20 C for 30 min, then 75 C for 15 min. Three microliter ligation mixture (0.5 ul 10×NEB 4, 1 ul 10 mM ATP, 1 ul T4 PNK (NEW ENGLAND BIOLABS), 0.5 ul T4 DNA Ligase (NEW ENGLAND BIOLABS)) was added and samples incubated at 16 C for 24 hours, then 75 C for 15 min. The sample was transferred to the standard ILLUMINA INFINIUM assay along with the maternal and alleged paternal genomic DNA. In short, 24 ul DNA was whole genome amplified at 37 C for 20-24 hours followed by fragmentation and precipitation. The precipitate was then resuspended in hybridization buffer, heat denatured and transferred to Cyto12 SNP arrays using a TECAN EVO. The arrays were incubated at 48 C for at least 16 hours, X-Stained (INFINIUM II CHEMISTRY) and washed in the TECAN EVO, and finally scanned. Array intensities were extracted using BEADSTIDUO (ILLUMINA).

The disclosed informatics method generated a test statistic that measured the degree of genetic similarity between the fetus and another individual. This test statistic was calculated for both the alleged father and a set of over 5,000 unrelated individuals. A single hypothesis rejection test then determined whether the statistic calculated for the alleged father could be excluded from the distribution formed by the unrelated reference individuals. If the alleged father could be rejected from the unrelated set, then a paternity inclusion resulted; otherwise, paternity was excluded. For the 20 samples with sufficient DNA, the paternity test was run against 20 correct fathers, and for 1,820 randomly selected incorrect fathers.

A paternity inclusion was called when the p-value of the alleged father's test statistic on the distribution of unrelated individuals was less than $10^{-4}$. This means that, in theory, no more than one out of 10,000 unrelated individuals are expected to show as much genetic similarity to the fetus. A "no call" was called where the p-value is between $10^{-4}$ and 0.02. An "insufficient fetal DNA" call was made when the fetal DNA made up less than 2% of the plasma DNA. The set of unrelated individuals used to generate the expected distribution was composed of individuals from a wide variety of racial backgrounds, and the paternity inclusion or exclusion determination was recalculated for sets of unrelated individuals of different races, including the race indicated for the alleged father. The inclusion and exclusion results were automatically generated by the algorithm, and no human intervention was necessary.

In conclusion, twenty one samples of maternal blood with known paternity were tested. Twenty out of 21 samples returned results, while one had insufficient fetal DNA for analysis; this sample was drawn from a woman at 8 weeks gestational age. Twenty of twenty (100%) results had the correct paternity confirmed, each with a p-value of $<10^{-4}$. Each of the 20 samples with sufficient fetal fraction was tested against a random set of 1,820 incorrect fathers, for a total of 36,400 individual paternity tests. 36,382 of these analyses returned a result; 36,382 of 36,382 (100%) correctly had the paternity excluded with a p-value of greater than $10^{-4}$, and 18 of 36,400 (0.05%) were called "no call", with a p-value between $10^{-4}$ and 0.02. There were no incorrect paternity exclusions or inclusions.

Nine of 21 samples had confirmed paternity due to control of fertilization during IVF with correct paternity confirmed after fertilization through pre-implantation genetic diagnosis. Twelve samples had paternity confirmed by independent paternity testing of fetal/child genomic DNA, conducted by DNA Diagnostic Center, Fairfield, Ohio.

Experiment 2

In one experiment, four maternal plasma samples were prepared and amplified using a hemi-nested 9,600-plex protocol. The samples were prepared in the following way: between 15 and 40 mL of maternal blood were centrifuged to isolate the buffy coat and the plasma. The genomic DNA in the maternal and was prepared from the buffy coat and paternal DNA was prepared from a blood sample or saliva sample. Cell-free DNA in the maternal plasma was isolated using the QIAGEN CIRCULATING NUCLEIC ACID kit and eluted in 45 uL TE buffer according to manufacturer's instructions. Universal ligation adapters were appended to the end of each molecule of 35 uL of purified plasma DNA and libraries were amplified for 7 cycles using adaptor specific primers. Libraries were purified with AGENCOURT AMPURE beads and eluted in 50 ul water.

3 ul of the DNA was amplified with 15 cycles of STA (95° C. for 10 min for initial polymerase activation, then 15 cycles of 95° C. for 30 s; 72° C. for 10 s; 65° C. for 1 min; 60° C. for 8 min; 65° C. for 3 min and 72° C. for 30 s; and a final extension at 72° C. for 2 min) using 14.5 nM primer concentration of 9600 target-specific tagged reverse primers and one library adaptor specific forward primer at 500 nM.

The hemi-nested PCR protocol involved a second amplification of a dilution of the first STAs product for 15 cycles of STA (95° C. for 10 min for initial polymerase activation, then 15 cycles of 95° C. for 30 s; 65° C. for 1 min; 60° C. for 5 min; 65° C. for 5 min and 72° C. for 30 s; and a final extension at 72° C. for 2 min. using reverse tag concentration of 1000 nM, and a concentration of 16.6 u nM for each of 9600 target-specific forward primers.

An aliquot of the STA products was then amplified by standard PCR for 10 cycles with 1 uM of tag-specific forward and barcoded reverse primers to generate barcoded sequencing libraries. An aliquot of each library was mixed with libraries of different barcodes and purified using a spin column.

In this way, 9,600 primers were used in the single-well reactions; the primers were designed to target SNPs found on chromosomes 1, 2, 13, 18, 21, X and Y. The amplicons were then sequenced using an ILLUMINA GAIIX sequencer. Per sample, approximately 3.9 million reads were generated by the sequencer, with 3.7 million reads mapping to the genome (94%), and of those, 2.9 million reads (74%) mapped to targeted SNPs with an average depth of read of 344 and a median depth of read of 255. The fetal fraction for the four samples was found to be 9.9%, 18.9%, 16.3%, and 21.2% Relevant maternal and paternal genomic DNA samples amplified using a semi-nested 9600-plex protocol and sequenced. The semi-nested protocol is different in that it applies 9,600 outer forward primers and tagged reverse primers at 7.3 nM in the first STA. Thermocycling conditions and composition of the second STA, and the barcoding PCR were the same as for the hemi-nested protocol.

The sequencing data was analyzed using informatics methods disclosed herein and each of a set of ten unrelated males from a reference set were determined to not be the biological father of each of the gestating fetuses.

Experiment 3

In one experiment 45 sets of cells were amplified using a 1,200-plex semi-nested protocol, sequenced, and ploidy determinations were made at three chromosomes. Note that this experiment is meant to simulate the conditions of performing paternity testing on single fetal cells obtained from maternal blood, or on forensic samples where a small amount of DNA from the child is present. 15 individual single cells and 30 sets of three cells were placed in 45 individual reaction tubes for a total of 45 reactions where each reaction contained cells from only one cell line, but the different reactions contained cells from different cell lines. The cells were prepared into 5 ul washing buffer and lysed the by adding 5 ul ARCTURUS PICOPURE lysis buffer (APPLIED BIOSYSTEMS) and incubating at 56° C. for 20 min, 95° C. for 10 min.

The DNA of the single/three cells was amplified with 25 cycles of STA (95° C. for 10 min for initial polymerase activation, then 25 cycles of 95° C. for 30 s; 72° C. for 10 s; 65° C. for 1 min; 60° C. for 8 min; 65° C. for 3 min and 72° C. for 30 s; and a final extension at 72° C. for 2 min) using 50 nM primer concentration of 1200 target-specific forward and tagged reverse primers.

The semi-nested PCR protocol involved three parallel second amplification of a dilution of the first STAs product for 20 cycles of STA (95° C. for 10 min for initial polymerase activation, then 15 cycles of 95° C. for 30 s; 65° C. for 1 min; 60° C. for 5 min; 65° C. for 5 min and 72° C. for 30 s; and a final extension at 72° C. for 2 min) using reverse tag specific primer concentration of 1000 nM, and a concentration of 60 nM for each of 400 target-specific nested forward primers. In the three parallel 400-plex reactions the total of 1200 targets amplified in the first STA were thus amplified.

An aliquot of the STA products was then amplified by standard PCR for 15 cycles with 1 uM of tag-specific forward and barcoded reverse primers to generate barcoded sequencing libraries. An aliquot of each library was mixed with libraries of different barcodes and purified using a spin column.

In this way, 1,200 primers were used in the single cell reactions; the primers were designed to target SNPs found on chromosomes 1, 21 and X. The amplicons were then sequenced using an ILLUMINA GAIIX sequencer. Per sample, approximately 3.9 million reads were generated by the sequencer, with 500,000 to 800,000 million reads mapping to the genome (74% to 94% of all reads per sample).

Relevant maternal and paternal genomic DNA samples from cell lines were analyzed using the same semi-nested 1200-plex assay pool with a similar protocol with fewer cycles and 1200-plex second STA, and sequenced.

The sequencing data was analyzed using informatics methods disclosed herein and each of a set of ten unrelated males from a reference set were determined to not be the biological father of the target individual for each of the 45 cells.

DNA from Children from Previous Pregnancies in Maternal Blood

One difficulty to non-invasive prenatal paternity testing is differentiating fetal cells from the current pregnancy from fetal cells from previous pregnancies. Some believe that genetic matter from prior pregnancies will go away after some time, but conclusive evidence has not been shown. In an embodiment of the present disclosure, it is possible to determine fetal DNA present in the maternal blood of paternal origin (that is, DNA that the fetus inherited from the father) using the PARENTAL SUPPORT™ (PS) method, and the knowledge of the paternal genome. This method may utilize phased parental genetic information. It is possible to phase the parental genotype from unphased genotypic information using grandparental genetic data (such as measured genetic data from a sperm from the grandfather), or genetic data from other born children, or a sample of a miscarriage. One could also phase unphased genetic information by way of a HapMap-based phasing, or a haplotyping of paternal cells. Successful haplotyping has been demonstrated by arresting cells at phase of mitosis when chromosomes are tight bundles and using microfluidics to put separate chromosomes in separate wells. In another embodiment it is possible to use the phased parental haplotypic data to detect the presence of more than one homolog from the father, implying that the genetic material from more than one child is present in the blood. By focusing on chromosomes that are expected to be euploid in a fetus, one could rule out the possibility that the fetus was afflicted with a trisomy. Also, it is possible to determine if the fetal DNA is not from the current father, in which case one could use other methods such as the triple test to predict genetic abnormalities.

There may be other sources of fetal genetic material available via methods other than a blood draw. In the case of the fetal genetic material available in maternal blood, there are two main categories: (1) whole fetal cells, for example, nucleated fetal red blood cells or erythroblats, and (2) free floating fetal DNA. In the case of whole fetal cells, there is some evidence that fetal cells can persist in maternal blood for an extended period of time such that it is possible to isolate a cell from a pregnant woman that contains the DNA from a child or fetus from a prior pregnancy. There is also evidence that the free floating fetal DNA is cleared from the system in a matter of weeks. One challenge is how to determine the identity of the individual whose genetic material is contained in the cell, namely to ensure that the measured genetic material is not from a fetus from a prior pregnancy. In an embodiment of the present disclosure, the knowledge of the maternal genetic material can be used to ensure that the genetic material in question is not maternal genetic material. There are a number of methods to accomplish this end, including informatics based methods such as PARENTAL SUPPORT™, as described in this document or any of the patents referenced in this document.

In an embodiment of the present disclosure, the blood drawn from the pregnant mother may be separated into a fraction comprising free floating fetal DNA, and a fraction comprising nucleated red blood cells. The free floating DNA may optionally be enriched, and the genotypic information of the DNA may be measured. From the measured genotypic information from the free floating DNA, the knowledge of the maternal genotype may be used to determine aspects of the fetal genotype. These aspects may refer to ploidy state, and/or a set of allele identities. Then, individual nucleated cells that are presumably or possible fetal in origin may be genotyped using methods described elsewhere in this document, and other referent patents, especially those mentioned in this document. The knowledge of the maternal genome would allow one to determine whether or not any given single blood cell is genetically maternal. And the aspects of the fetal genotype that were determined as described above would allow one to determine if the single blood cell is genetically derived from the fetus that is currently gestating. In essence, this aspect of the present disclosure allows one to use the genetic knowledge of the mother, and possibly the genetic information from other related individuals, such as the father, along with the measured genetic information from the free floating DNA found in maternal blood to determine whether an isolated nucleated cell found in maternal blood is either (a) genetically maternal, (b) genetically from the fetus currently gestating, or (c) genetically from a fetus from a prior pregnancy.

All patents, patent applications, and published references cited herein are hereby incorporated by reference in their entirety. It will be appreciated that several of the above-disclosed and other features and functions, or alternatives thereof, may be desirably combined into many other different systems or applications. Various presently unforeseen or unanticipated alternatives, modifications, variations, or improvements therein may be subsequently made by those skilled in the art which are also intended to be encompassed by the following claims.

What is claimed is:

1. A method of amplifying target loci in a nucleic acid sample, the method comprising:
   (a) performing multiplex PCR on a nucleic acid sample comprising target loci to simultaneously amplify at least 1,000 distinct target loci using either (i) at least 1,000 different primer pairs or (ii) at least 1,000 target-specific primers and a universal or tag-specific primer, wherein the multiplex PCR is performed in a single reaction volume to produce amplified products comprising target amplicons and
   (b) sequencing the amplified products using high-throughput sequencing;
   wherein the concentration of each primer in the primer pairs or each target-specific primer is less than 20 nM; and wherein the length of an annealing step of the multiplex PCR amplification is greater than 10 minutes.

2. The method of claim 1, comprising obtaining primers for use in step (a) by empirically or in silico identifying one or more primers that form a primer dimer with another primer in a library of potential primers with the greatest frequency, eliminating the one or more identified primers from the library of potential primers, and using the primers remaining in the library in step (a).

3. The method of claim 1, comprising performing universal amplification on nucleic acids in the sample prior to step (a), wherein the universal amplification optionally comprises universal PCR, whole genome amplification, ligation-mediated PCR, degenerate oligonucleotide primer PCR, or multiple displacement amplification.

4. The method of claim 1, wherein the multiplex PCR comprises fully nested, semi-nested, or hemi-nested PCR; or wherein each primer pair comprises a forward and a reverse primer in which the 3' ends of the forward and reverse primers are designed to hybridize to a region of DNA separated from a polymorphic site in a target locus by a small number of bases, wherein the small number is from 1 to 20 bases.

5. The method of claim 4, wherein each primer pair comprises an inner forward primer in which the 3' end of the inner forward primer is designed to hybridize to a region of DNA separated from a polymorphic site in a target locus by a small number of bases, wherein the small number is from 2 to 60 bases.

6. The method of claim 1, wherein each primer pair comprises a forward and a reverse primer in which the 3' end of the forward and reverse primer is designed to hybridize to a region of DNA separated from a polymorphic site in a target locus by a small number of bases, wherein the small number is from 2 to 20 bases.

7. The method of claim 1, comprising simultaneously amplifying at least 5,000 distinct target loci.

8. The method of claim 1, wherein at least 90% of the amplified products map to the target loci.

9. The method of claim 1, wherein the multiplex PCR amplification comprises 20 cycles of PCR, and the average degree of allelic bias between the sample and the target amplicons is no more than a factor of 1.2.

10. The method of claim 1, wherein the nucleic acid sample is isolated from a blood, plasma, or serum sample.

11. The method of claim 10, wherein the nucleic acid sample comprises DNA from a fetus.

12. The method of claim 10, wherein the nucleic acid sample comprises DNA from a transplant.

13. The method of claim 1, wherein the target loci are present in the human genome.

14. The method of claim 1, wherein the target loci comprise human single nucleotide polymorphisms.

15. The method of claim 1, wherein the length of the target amplicons is less than 100 nucleotides.

16. The method of claim 1, wherein the nucleic acid sample comprises DNA molecules with an average length of less than 200 base pairs, and wherein the target amplicons are less than 100 nucleotides in length.

* * * * *